US009855348B2

(12) United States Patent
Devoogdt et al.

(10) Patent No.: US 9,855,348 B2
(45) Date of Patent: Jan. 2, 2018

(54) RADIO-LABELLED ANTIBODY FRAGMENTS FOR USE IN THE PREVENTION AND/OR TREATMENT OF CANCER

(71) Applicant: VRIJE UNIVERSITEIT BRUSSEL, Brussels (BE)

(72) Inventors: Nick Devoogdt, Eppegem-Zemst (BE); Jens De Vos, Strombeek-Bever (BE); Matthias D'Huyvetter, Wilrijk (BE); Tony Lahoutte, Ganshoren (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 89 days.

(21) Appl. No.: 14/802,077

(22) Filed: Jul. 17, 2015

(65) Prior Publication Data

US 2016/0030606 A1 Feb. 4, 2016

(30) Foreign Application Priority Data

Jul. 29, 2014 (EP) .................................... 14178943

(51) Int. Cl.
| | | |
|---|---|---|
| A61K 39/395 | (2006.01) | |
| A61K 51/10 | (2006.01) | |
| C07K 16/32 | (2006.01) | |
| A61K 9/00 | (2006.01) | |

(52) U.S. Cl.
CPC ........ *A61K 51/1045* (2013.01); *A61K 9/0019* (2013.01); *A61K 51/1051* (2013.01); *A61K 51/1069* (2013.01); *A61K 51/1072* (2013.01); *A61K 51/1078* (2013.01); *A61K 51/1096* (2013.01); *C07K 16/32* (2013.01); *C07K 2317/56* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2009/0304590 A1* 12/2009 Gill .................... C07K 16/2863
424/9.1

FOREIGN PATENT DOCUMENTS

| WO | 1996/008565 A2 | 3/1996 |
| WO | 2003/055527 A2 | 7/2003 |
| WO | 2010/004432 A1 | 1/2010 |
| WO | 2010/042815 A2 | 4/2010 |
| WO | 2011/051327 A2 | 5/2011 |

OTHER PUBLICATIONS

MacCallum et al, J. Mol. Biol., 262, 732-745, 1996.*
Granziero et al, Eur. J. Immunol. 1999, 29:1127-1138.*
Byers, T, CA Journal, vol. 49, No. 6, Nov./Dec. 1999.*
Pruszynski et al, Nuclear Med Biol, 40:52-59, 2013.*
Xavier et al. (Sep. 20, 2014) "Anti-HER2 Nanobodies: Novel Theranostic Tools," In; The Abstracts of 7th World Molecular Imaging Congress, 2014. Scientific Session 08: SS 46. Seoul, South Korea.
International Search Report with Written Opinion corresponding to International Patent Application No. PCT/EP2015/066430, dated Nov. 10, 2015.
International Preliminary Report on Patentability corresponding to International Patent Application No. PCT/EP2015/066430, completed Jun. 22, 2016.
D'Huyvetter et al. (Apr. 25, 2014) "Targeted Radionuclide Therapy with a 177Lu-labeled Anti-HER2 Nanobody," Theranostics. 4(7):708-720.
D'Huyvetter et al. (Mar. 30, 2012) "Development of 177Lu-nanobodies for radioimmunotherapy of HER2-positive breast cancer: evaluation of different bifunctional chelators," Contrast Media and Molecular Imaging. 7:254-264.
D'Huyvetter et al. (Sep. 1-3, 2013) "Nanobody-based Targeted Radiotherapy for Cancer Treatment," In; The European Cooperation in the field of Science and Technology Meeting 2013: Theragnostics Imaging and Therapy: An Action to Develop Novel Nanosized Systems for Imaging-Guided Drug Delivery. Action TD1004. Athens, Greece—Meeting abstract only.
Gibbs (2005) "Nanobodies," Scientific American. 293(2):67-71.
Massa (2011) "Site-specific coupling of Nanobodies® directed against the membrane protein HER2 for non-invasive, multi-modal imaging in pre-clinical cancer models," Master's Thesis for the fulfillment of the degree of Master of Bioscience Engineering : Cell and Gene Biotechnology—Medical Biotechnology. Vrije Universiteit Brussel. Brussels, Belgium.—with English machine translation.
Oliveira et al. (Dec. 28, 2013) "Targeting tumors with nanobodies for cancer imaging and therapy," Journal of Controlled Release. 172(3):607-617.
Pruszynski et al. (Feb. 27, 2014) "Improved Tumor Targeting of Anti-HER2 Nanobody Through N-Succinimidyl 4-Guanidinomethyl-3-Iodobenzoate Radiolabeling," The Journal of Nuclear Medicine. 55(4):650-656.
Schoonooghe et al. (Dec. 2012) "Novel applications of nanobodies for in vivo bio-imaging of inflamed tissues in inflammatory diseases and cancer," Immunobiology. 217(12):1266-1272.
Siontorou (Nov. 2013) "Nanobodies as novel agents for disease diagnosis and therapy," International Journal of Nanomedicine. 8:4215-4227.

(Continued)

*Primary Examiner* — Mark Halvorson
(74) *Attorney, Agent, or Firm* — Lathrop Gage LLP; James H. Velema, Esq.

(57) ABSTRACT

The application provides polypeptides comprising or essentially consisting of at least one heavy chain variable domain of a heavy chain antibody ($V_{HH}$) or functional fragments thereof, wherein said $V_{HH}$ or functional fragment thereof specifically binds to a target protein that is present on and/or specific for a solid tumor or cancer cell, e.g., HER2. The application further provides nucleic acids encoding such polypeptides; methods for preparing such polypeptides; host cells expressing or capable of expressing such polypeptides; compositions, and in particular to pharmaceutical compositions that comprise such polypeptides, nucleic acids and/or host cells. The application further provides such polypeptides, nucleic acids, host cells and/or compositions, for use in methods for the prevention and/or treatment of cancer.

19 Claims, 26 Drawing Sheets

(56) References Cited

OTHER PUBLICATIONS

Szpakowska (2010) "Selection of HER2-Specific Internalising Nanobodies," Master's Thesis for the partial fulfillment of the degree of Master of Biomolecular Sciences. Vrije Universiteit Brussel. Brussels, Belgium.
Tijink et al. (2008) "Improved tumor targeting of anti-epidermal growth factor receptor Nanobodies through albumin binding: taking advantage of modular Nanobody technology," Molecular Cancer Therapeutics. 7(8):2288-2297.
Van Gassen (2009) "Characterization of anti-HER2 Nanobodies for non-invasive imaging of HER2 Positive Tumors," Master's Thesis for the fulfillment of the degree of Master of Biology: Genetics, Cellular and Developmental Biology. Vrije Universiteit Brussel. Brussels, Belgium.—with English machine translation.
Vosjan et al. (Feb. 7, 2012) "Nanobodies Targeting the Hepatocyte Growth Factor: Potential New Drugs for Molecular Cancer Therapy," Molecular Cancer Therapeutics. 11(4):1017-1025.
Search Report with Search Opinion corresponding to European Patent Application No. 14178943.8, dated Apr. 28, 2015.
D'Huyvetter (Sep. 7, 2012) "Evaluation of bivalent antiHER2 Nanobody constructs for improved cellular retention and in vivo tumor targeting," Abstract for Poster Presentation No. P529 Presented in; The World Molecular Imaging Congress, 2012, Dublin, Ireland. 2 pgs.
D'Huyvetter (Sep. 7, 2012) "Evaluation of bivalent antiHER2 Nanobody constructs for improved cellular retention and in vivo tumor targeting," Poster for Poster Presentation No. P529 Presented in; The World Molecular Imaging Congress, 2012, Dublin, Ireland. 1 pg.

\* cited by examiner

|  | Naïve | | | 5T33MM | | | 5T2MM | | |
|---|---|---|---|---|---|---|---|---|---|
| cAbBCII10 | Mean | SEM | N | Mean | SEM | N | Mean | SEM | N |
| Heart | 0.43 | 0.00 | 3 | 0.28 | 0.01 | 3 | 0.47 | 0.03 | 6 |
| Lungs | 1.02 | 0.15 | 3 | 1.16 | 0.14 | 3 | 1.14 | 0.10 | 6 |
| Liver | 0.60 | 0.07 | 3 | 0.77 | 0.08 | 3 | 1.03 | 0.09 | 6 |
| Spleen | 0.42 | 0.06 | 3 | 0.30 | 0.03 | 3 | 0.36 | 0.02 | 6 |
| Left kidney | 215.73 | 6.69 | 3 | 190.02 | 3.94 | 3 | 208.19 | 8.32 | 6 |
| Right kidney | 218.92 | 3.41 | 3 | 201.92 | 6.32 | 3 | 215.18 | 8.46 | 6 |
| Muscle | 0.20 | 0.02 | 3 | 0.19 | 0.04 | 3 | 0.24 | 0.02 | 6 |
| Bone | 0.29 | 0.11 | 3 | 0.24 | 0.01 | 3 | 0.29 | 0.03 | 6 |
| Luymph nodes | 0.31 | 0.05 | 3 | 0.24 | 0.01 | 3 | 0.33 | 0.04 | 6 |
| Blood | 0.89 | 0.03 | 3 | 0.64 | 0.01 | 3 | 1.03 | 0.04 | 6 |

| | Naive | | | 5T33MM | | | 5T2MM | | |
|---|---|---|---|---|---|---|---|---|---|
| R3B23 | Mean | SEM | N | Mean | SEM | N | Mean | SEM | N |
| Heart | 0.22 | 0.01 | 3 | 0.26 | 0.06 | 3 | 8.92 | 1.37 | 3 |
| Lungs | 0.48 | 0.03 | 3 | 0.54 | 0.08 | 3 | 11.64 | 2.35 | 3 |
| Liver | 0.60 | 0.01 | 3 | 0.40 | 0.05 | 3 | 8.21 | 0.90 | 3 |
| Spleen | 0.30 | 0.03 | 3 | 0.20 | 0.01 | 3 | 7.03 | 0.96 | 3 |
| Left kidney | 162.71 | 4.03 | 3 | 114.44 | 11.71 | 3 | 7.18 | 0.74 | 3 |
| Right kidney | 159.94 | 7.43 | 3 | 126.10 | 18.30 | 3 | 8.14 | 0.94 | 3 |
| Muscle | 0.26 | 0.10 | 3 | 0.12 | 0.03 | 3 | 0.91 | 0.12 | 3 |
| Bone | 0.14 | 0.02 | 3 | 0.23 | 0.06 | 3 | 2.14 | 0.04 | 3 |
| Luymph nodes | 0.20 | 0.03 | 3 | 0.27 | 0.09 | 3 | 2.83 | 1.25 | 3 |
| Blood | 0.40 | 0.02 | 3 | 0.67 | 0.15 | 3 | 44.56 | 2.54 | 3 |

Figure 5A
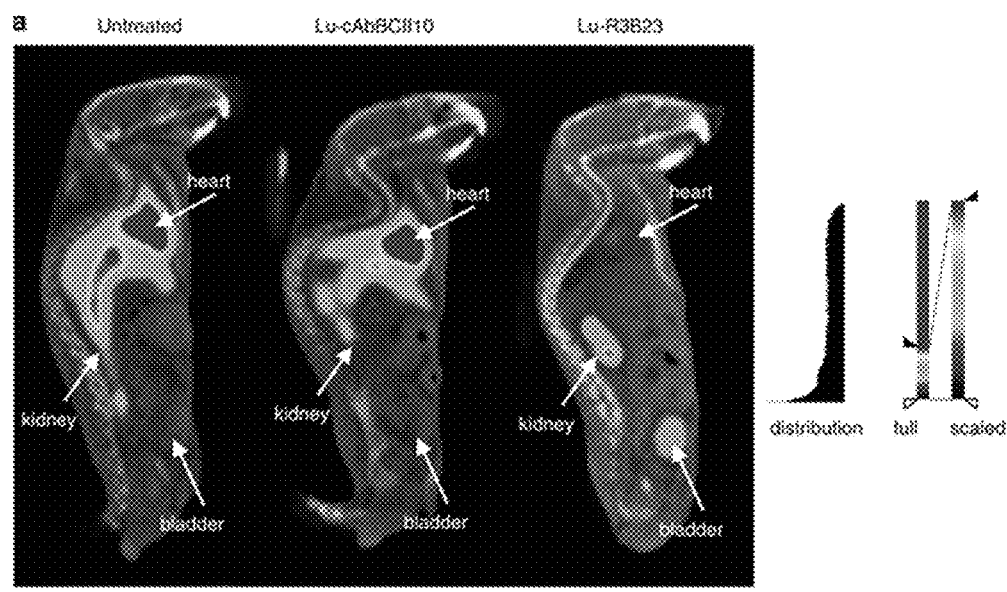
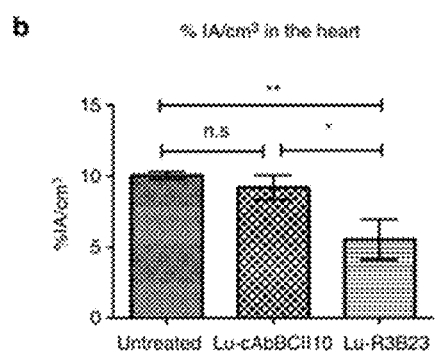
Figure 5B
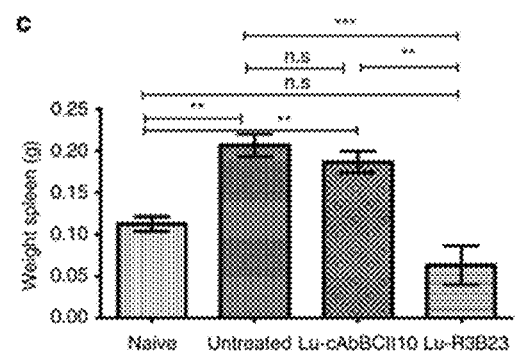
Figure 5C

RADIO-LABELLED ANTIBODY FRAGMENTS FOR USE IN THE PREVENTION AND/OR TREATMENT OF CANCER

RELATED APPLICATIONS

This application claims the benefit of priority to European Patent Application No.: 14178943.8, filed Jul. 29, 2014, entitled RADIO-LABELLED ANTIBODY FRAGMENTS FOR USE IN THE PREVENTION AND/OR TREATMENT OF CANCER. The contents of the aforementioned application are incorporated herein by reference in their entirety.

FIELD OF THE INVENTION

The present disclosure relates to the field of radio-labelled antibody fragments and uses thereof for prophylactic and/or therapeutic purposes. In particular, the present disclosure relates to radiolabelled antibody fragments for use in the prevention and/or treatment of cancer.

BACKGROUND

In contrast to the overwhelming success of radiolabeled antibodies in treating hematologic malignancies, only modest success has been achieved in the radioimmunotherapy of solid tumors. One of the limitations in successful application of radioimmunotherapy is the large molecular size of the intact immunoglobulin that results in prolonged serum half-life and poor tumor penetration and uptake. With the advent of antibody engineering, small molecular weight antibody fragments exhibiting improved pharmacokinetics and tumor penetration have been generated. However, their clinical application has been limited by suboptimal tumor uptake and short tumor residence time. Optimization of the molecular size of the antibodies alone is therefore not sufficient for clinical success of radioimmunotherapy.

Indeed, apart from their large size, radiolabeled antibodies encounter other impediments before reaching their target antigens expressed on the cell surface of solid tumors. Some of these barriers include poor blood flow in large tumors, permeability of vascular endothelium, elevated interstitial fluid pressure of tumor stroma, and heterogeneous antigen expression.

New optimization strategies involve the use of biological modifiers to modulate the impediments posed by solid tumors. In combination with radiolabeled antibodies, various agents are being used to improve the tumor blood flow, enhance vascular permeability, lower tumor interstitial fluid pressure by modulating stromal cells and extracellular matrix components, up-regulate the expression of target antigens, and improve the penetration and retention of the radiopharmaceuticals.

Nevertheless, the clinical success of radioimmunotherapy for solid tumors still seems to be a distant dream because only a very small amount of administered antibody (as low as 0.001-0.01%) localizes in the tumor and administration of higher amounts of radiolabeled mAbs causes myelotoxicity. To be clinically successful, radioimmunotherapy for solid tumors needs to be optimized so as to enhance the tumor uptake and retention of radiolabeled antibodies in the tumor and minimizing the exposure of non-target tissues.

Pruszynski et al. (2014) showed improved tumor targeting of a HER2-targeting $V_{HH}$ through labeling with $^{131}I$ using N-succinimidyl-4-guanidinomethyl 3-$^{125-131}I$-iodobenzoate, when compared to radioiodination with $N^{\epsilon}$-(3-*I-iodobenzoyl)-Lys$^5$-$N^{\alpha}$-maleimido-Gly$^1$-GEEEK and direct radioiodination of the $V_{HH}$ using IODO-GEN. Tumor uptake for the *I-SGMIB-$V_{HH}$ was significantly reduced with Trastuzumab blocking, indicating competition between the $V_{HH}$ and Trastuzumab for HER2 binding. The $V_{HH}$ disclosed in Pruszynski et al. contains a carboxy-terminal cysteine-containing tail, resulting in an equilibrium mixture of monomeric and dimeric forms. Pruszynski et al. failed to show any therapeutic effect of the radiolabeled $V_{HH}$s.

SUMMARY OF THE INVENTION

The present inventors have identified novel and improved antibody fragments which specifically bind to a target protein that is present on and/or specific for a solid tumor or for a cancer cell for use in the treatment of cancer.

In particular, through the radiolabelling of a specific type of antibody fragments, i.e. the heavy chain variable domains derived from heavy chain antibodies (hereinafter referred to as $V_{HH}$'s), which specifically interact with solid tumors or with a cancer cell, the present inventors have developed an improved and effective radioimmunotherapy strategy, that is characterized by high tumor uptake or cancer cell uptake values, low healthy tissue uptake values, low overall biodistribution and fast clearance from the blood.

The radiolabelled antibody fragments as disclosed herein thus, in some embodiments, show several advantages over the traditional (immunoglobulin and non-immunoglobulin) binding agents known in the art, including a higher potency, lower toxicity and a higher stability leading to (1) a potential for a higher maximally tolerated dosage (MTD) in medical applications, allowing repeated and continued administration of a high treatment dosage, so as to effectively counteract tumor or cancer cell growth while still remaining below the dose-limiting toxicity (DLT) side-effects on normal healthy tissue (being particularly relevant in radioimmunotherapy); and (2) a broader choice of administration routes, comprising oral, subcutaneous, intraperitoneal routes and slow-release formulations in addition to the intravenous route. Also, because of their small size, the antibody fragments as disclosed herein have the ability to penetrate into physiological compartments, tissues and organs not accessible to other, larger polypeptides and proteins.

Surprisingly, in some embodiments, the radiolabelled antibody fragments as disclosed herein are used in a monovalent format, and were not modified for extending the life-time. Indeed, while whole antibodies have an exceptionally long half-life, small antibody fragments often suffer from rapid elimination from the circulation. Therefore, in vivo applications of $V_{HH}$'s typically rely on $V_{HH}$'s that have been modified, for example, by coupling to an anti-serum albumin $V_{HH}$ or by pegylation, to extend the plasma half-life (Siontorou 2013 International Journal of Nanomedicine 8:4215-4227; Tijink et al. 2008 Mol Cancer Ther 7:2288-2297) Also, multimerization of $V_{HH}$'s can prolong in vivo retention and increases affinity (Siontorou 2013). The present inventors demonstrated therapeutic efficacy of monovalent, non-lifetime extended $V_{HH}$'s.

The present disclosure provides such radio-labelled antibody fragments, as well as polypeptides that comprise or essentially consist of one or more such radio-labelled antibody fragments and the uses of such radio-labelled antibody fragments or polypeptides for prophylactic and/or therapeutic purposes, in particular for radioimmunotherapy.

In particular embodiments, the radio-labelled antibody fragments, as well as polypeptides that comprise or essentially consist of one or more such radio-labelled antibody fragments, can be used for the prevention or prophylaxis of cancer, such as for example but not limited to the prevention of cancer disease recurrence, i.e. to avoid or prevent the return of one or more signs, symptoms, or disease after a remission.

In some aspects, the disclosure relates to a method for one or both of the prevention and treatment of cancer, the method comprising administering to a subject in need thereof an effective amount of a radiolabelled, untagged monovalent heavy chain variable domain derived from a heavy chain antibody ($V_{HH}$), or a functional fragment thereof, which specifically binds to a target protein that is present on a cancer cell or solid tumor.

In some embodiments of any one of the methods as described herein, the radiolabelled, untagged monovalent $V_{HH}$ or functional fragment thereof is labeled with a halogen radio-isotope.

In some embodiments of any one of the methods as described herein, the radiolabelled, untagged monovalent $V_{HH}$ or functional fragment thereof is labeled with 131-Iodine.

In some embodiments of any one of the methods as described herein, the radiolabelled, untagged monovalent $V_{HH}$ or functional fragment thereof is labeled with 131-Iodine using N-succinimidyl-4-guanidinomethyl-3-[I-131]iodobenzbate ([I-131]SGMIB) or a suitable derivative or variant thereof.

In some embodiments of any one of the methods as described herein, the radiolabelled, untagged monovalent $V_{HH}$ or functional fragment thereof is labeled with a radio-isotope chosen from the group consisting of α-emitting radioisotopes and β-emitting radioisotopes. In some embodiments, the radiolabelled, untagged monovalent $V_{HH}$ or functional fragment thereof is labeled with a radio-isotope chosen from the group consisting of Actinium-225, Astatine-211, Bismuth-212, Bismuth-213, Caesium-137, Chromium-51, Cobalt-60, Dysprosium-165, Erbium-169, Fermium-255, Gold-198, Holium-166, Iodine-125, Iodine-131, Iridium-192, Iron-59, Lead-212, Lutetium-177, Molydenum-99, Palladium-103, Phosphorus-32, Potassium-42, Rhenium-186, Rhenium-188, Samarium-153, Technitium-99m, Radium-223, Ruthenium-106, Sodium-24, Strontium-89, Terbium-149, Thorium-227, Xenon-133, Ytterbium-169, Ytterbium-177 and Yttrium-90.

In some embodiments of any one of the methods as described herein, the radiolabelled, untagged monovalent $V_{HH}$ or functional fragment thereof specifically binds to HER2.

In some embodiments of any one of the methods as described herein, the radiolabelled, untagged monovalent $V_{HH}$ or functional fragment thereof specifically binds to HER2 and is labeled with a halogen radio-isotope.

In some embodiments of any one of the methods as described herein, the radiolabelled, untagged monovalent $V_{HH}$ or functional fragment thereof specifically binds to HER2 and is labeled with 131-Iodine.

In some embodiments of any one of the methods as described herein, the radiolabelled, untagged monovalent $V_{HH}$ or functional fragment thereof specifically binds to HER2 and is labeled with 131-Iodine using N-succinimidyl-4-guanidinomethyl-3-[I-131]iodobenzbate ([I-131]SGMIB) or a suitable derivative or variant thereof.

In some embodiments of any one of the methods as described herein, the radiolabelled, untagged monovalent $V_{HH}$ or functional fragment thereof does not compete with the monoclonal antibody Herceptin® (Trastuzumab) or the monoclonal antibody Pertuzumab (Perjeta®) for binding to HER2, as determined using a competition assay.

In some embodiments of any one of the methods as described herein, the radiolabelled, untagged monovalent $V_{HH}$ or functional fragment thereof is administered to the subject in a calculated mean effective dose of between 0.002 and 0.1 mSv/MBq in said subject.

In some embodiments of any one of the methods as described herein, the radiolabelled, untagged monovalent $V_{HH}$ or functional fragment thereof is administered to the subject at an administration interval of between once a day and once a month or between once a month and once a year.

In some embodiments of any one of the methods as described herein, the radiolabelled, untagged monovalent $V_{HH}$ or functional fragment thereof binds to HER2 present on a solid tumor or cancer cell with an affinity of less than 5 nM.

In some embodiments of any one of the methods as described herein, the radiolabelled, untagged monovalent $V_{HH}$, or functional fragment thereof, comprises one of the CDR combinations chosen from the group comprising:
  a CDR1 region having SEQ ID NO:1, a CDR2 region having SEQ ID NO:2, and a CDR3 region having SEQ ID NO:3, and
  a CDR1 region having SEQ ID NO:4, a CDR2 region having SEQ ID NO:5, and a CDR3 region having SEQ ID NO:6.

In some embodiments of any one of the methods as described herein, the radiolabelled, untagged monovalent $V_{HH}$, or functional fragment thereof, has at least 80% amino acid identity with at least one of the amino acid sequences of SEQ ID NOs:7 and 8.

In some embodiments of any one of the methods as described herein, the radiolabelled, untagged monovalent $V_{HH}$, or functional fragment thereof, is identical with at least one of the amino acid sequences of SEQ ID NOs:7 and 8.

In some embodiments of any one of the methods as described herein, the radiolabelled, untagged monovalent $V_{HH}$, or functional fragment thereof, comprises
  one of the CDR combinations chosen from the group comprising:
  a CDR1 region having SEQ ID NO:1, a CDR2 region having SEQ ID NO:2, and a CDR3 region having SEQ ID NO:3, and
  a CDR1 region having SEQ ID NO:4, a CDR2 region having SEQ ID NO:5, and a CDR3 region having SEQ ID NO:6; and
  is labeled with 131-Iodine using N-succinimidyl-4-guanidinomethyl-3-[I-131]iodobenzbate ([I-131]SGMIB) or a suitable derivative or variant thereof.

In some embodiments of any one of the methods as described herein, the radiolabelled, untagged monovalent $V_{HH}$, or functional fragment thereof, has at least 80% amino acid identity with at least one of the amino acid sequences of SEQ ID NOs:7 and 8 and is labeled with 131-Iodine using N-succinimidyl-4-guanidinomethyl-3-[I-131]iodobenzbate ([I-131]SGMIB) or a suitable derivative or variant thereof.

In some embodiments of any one of the methods as described herein, the radiolabelled, untagged monovalent $V_{HH}$, or functional fragment thereof, is identical with at least one of the amino acid sequences of SEQ ID NOs:7 and 8 and is labeled with 131-Iodine using N-succinimidyl-4-guanidinomethyl-3-[I-131]iodobenzbate ([I-131]SGMIB) or a suitable derivative or variant thereof.

In some embodiments of any one of the methods as described herein, the cancer is breast cancer.

In some embodiments of any one of the methods as described herein, the method further comprises performing immunotherapy on the subject.

In some embodiments of any one of the methods as described herein, the radiolabelled, monovalent $V_{HH}$ or functional fragment thereof is administered to the subject intravenously, intraperitoneally, or intrathecally.

In some embodiments of any one of the methods as described herein, the radiolabelled, monovalent $V_{HH}$ or functional fragment thereof is non-lifetime extended.

In some embodiments of any one of the methods as described herein, the radiolabelled, monovalent $V_{HH}$ or functional fragment thereof is devoid of a carboxy-terminal polypeptide tag.

Other aspects of the disclosure relate to a radiolabelled, untagged monovalent heavy chain variable domain derived from a heavy chain antibody ($V_{HH}$), or a functional fragment thereof, which specifically binds to a target protein that is present on a cancer cell or a solid tumor. In some embodiments, the radiolabelled, untagged monovalent $V_{HH}$ or functional fragment thereof specifically binds to HER2. In some embodiments, the radiolabelled, untagged monovalent $V_{HH}$ or functional fragment thereof is labeled with 131-Iodine using N-succinimidyl-4-guanidinomethyl-3-[I-131]iodobenzbate ([I-131]SGMIB) or a suitable derivative or variant thereof. In some embodiments, the radiolabelled, untagged monovalent $V_{HH}$ or functional fragment thereof specifically binds to HER2 and is labeled with 131-Iodine using N-succinimidyl-4-guanidinomethyl-3-[I-131]iodobenzbate ([I-131]SGMIB) or a suitable derivative or variant thereof.

In some embodiments of any one of the radiolabelled, untagged monovalent $V_{HH}$s or functional fragments thereof described herein, the $V_{HH}$ or functional fragment thereof does not compete with the monoclonal antibody Herceptin® (Trastuzumab) or the monoclonal antibody Pertuzumab (Perjeta®) for binding to HER2, as determined using a competition assay.

In some embodiments of any one of the radiolabelled, untagged monovalent $V_{HH}$s or functional fragments thereof described herein, the radiolabelled, monovalent $V_{HH}$ or functional fragment thereof binds to HER2 present on a solid tumor or cancer cell with an affinity of less than 5 nM.

In some embodiments of any one of the radiolabelled, untagged monovalent $V_{HH}$s or functional fragments thereof described herein, the radiolabelled, monovalent $V_{HH}$ or functional fragment thereof comprises one of the CDR combinations chosen from the group comprising:
  a CDR1 region having SEQ ID NO:1, a CDR2 region having SEQ ID NO:2, and a CDR3 region having SEQ ID NO:3, and
  a CDR1 region having SEQ ID NO:4, a CDR2 region having SEQ ID NO:5, and a CDR3 region having SEQ ID NO:6.

In some embodiments of any one of the radiolabelled, untagged monovalent $V_{HH}$s or functional fragments thereof described herein, the radiolabelled, monovalent $V_{HH}$ or a functional fragment thereof has at least 80% amino acid identity with at least one of the amino acid sequences of SEQ ID NOs:7 and 8.

In some embodiments of any one of the radiolabelled, untagged monovalent $V_{HH}$s or functional fragments thereof described herein, the radiolabelled, monovalent $V_{HH}$ or a functional fragment thereof is identical with at least one of the amino acid sequences of SEQ ID NOs:7 and 8.

In some embodiments of any one of the radiolabelled, untagged monovalent $V_{HH}$s or functional fragments thereof described herein, the radiolabelled, monovalent $V_{HH}$ or functional fragment thereof comprises
  one of the CDR combinations chosen from the group comprising:
  a CDR1 region having SEQ ID NO:1, a CDR2 region having SEQ ID NO:2, and a CDR3 region having SEQ ID NO:3, and
  a CDR1 region having SEQ ID NO:4, a CDR2 region having SEQ ID NO:5, and a CDR3 region having SEQ ID NO:6; and
  is labeled with 131-Iodine using N-succinimidyl-4-guanidinomethyl-3-[I-131]iodobenzbate ([I-131]SGMIB) or a suitable derivative or variant thereof.

In some embodiments of any one of the radiolabelled, untagged monovalent $V_{HH}$s or functional fragments thereof described herein, the radiolabelled, monovalent $V_{HH}$ or a functional fragment thereof has at least 80% amino acid identity with at least one of the amino acid sequences of SEQ ID NOs:7 and 8 and is labeled with 131-Iodine using N-succinimidyl-4-guanidinomethyl-3-[I-131]iodobenzbate ([I-131]SGMIB) or a suitable derivative or variant thereof.

In some embodiments of any one of the radiolabelled, untagged monovalent $V_{HH}$s or functional fragments thereof described herein, the radiolabelled, monovalent $V_{HH}$ or a functional fragment thereof is identical with at least one of the amino acid sequences of SEQ ID NOs:7 and 8 and is labeled with 131-Iodine using N-succinimidyl-4-guanidinomethyl-3-[I-131]iodobenzbate ([I-131]SGMIB) or a suitable derivative or variant thereof.

In some embodiments of any one of the radiolabelled, untagged monovalent $V_{HH}$s or functional fragments thereof described herein, the radiolabelled, monovalent $V_{HH}$ or functional fragment thereof is non-lifetime extended.

In some embodiments of any one of the radiolabelled, untagged monovalent $V_{HH}$s or functional fragments thereof described herein, the radiolabelled, monovalent $V_{HH}$ or functional fragment thereof is devoid of a carboxy-terminal polypeptide tag.

Yet other aspects of the disclosure relate to a pharmaceutical composition comprising any one of the radiolabelled, untagged monovalent $V_{HH}$s or functional fragments thereof as described herein. In some embodiments of the pharmaceutical composition, the radiolabelled, untagged monovalent $V_{HH}$ or functional fragment thereof specifically binds to a target protein that is present on a cancer cell or a solid tumor. In some embodiments of the pharmaceutical composition, the radiolabelled, untagged monovalent $V_{HH}$ or functional fragment thereof specifically binds to HER2. In some embodiments of the pharmaceutical composition, the radiolabelled, untagged monovalent $V_{HH}$ or functional fragment thereof is labeled with 131-Iodine using N-succinimidyl-4-guanidinomethyl-3-[I-131]iodobenzbate ([I-131]SGMIB) or a suitable derivative or variant thereof. In some embodiments of the pharmaceutical composition, the radiolabelled, untagged monovalent $V_{HH}$ or functional fragment thereof specifically binds to HER2 and is labeled with 131-Iodine using N-succinimidyl-4-guanidinomethyl-3-[I-131]iodobenzbate ([I-131]SGMIB) or a suitable derivative or variant thereof.

In some embodiments of the pharmaceutical composition, the $V_{HH}$ or functional fragment thereof does not compete with the monoclonal antibody Trastuzumab (Herceptin®) or the monoclonal antibody Pertuzumab (Perjeta®) for binding to HER2, as determined using a competition assay.

In some embodiments of the pharmaceutical composition, the radiolabelled, monovalent $V_{HH}$ or functional fragment thereof binds to HER2 present on a solid tumor or cancer cell with an affinity of less than 5 nM.

In some embodiments of the pharmaceutical composition, the radiolabelled, monovalent $V_{HH}$ or functional fragment thereof comprises one of the CDR combinations chosen from the group comprising:
- a CDR1 region having SEQ ID NO:1, a CDR2 region having SEQ ID NO:2, and a CDR3 region having SEQ ID NO:3, and
- a CDR1 region having SEQ ID NO:4, a CDR2 region having SEQ ID NO:5, and a CDR3 region having SEQ ID NO:6.

In some embodiments of the pharmaceutical composition, the radiolabelled, monovalent $V_{HH}$ or a functional fragment thereof has at least 80% amino acid identity with at least one of the amino acid sequences of SEQ ID NOs:7 and 8.

In some embodiments of the pharmaceutical composition, the radiolabelled, monovalent $V_{HH}$ or a functional fragment thereof is identical with at least one of the amino acid sequences of SEQ ID NOs:7 and 8.

In some embodiments of the pharmaceutical composition, the radiolabelled, monovalent $V_{HH}$ or functional fragment thereof comprises one of the CDR combinations chosen from the group comprising:
- a CDR1 region having SEQ ID NO:1, a CDR2 region having SEQ ID NO:2, and a CDR3 region having SEQ ID NO:3, and
- a CDR1 region having SEQ ID NO:4, a CDR2 region having SEQ ID NO:5, and a CDR3 region having SEQ ID NO:6; and
- is labeled with 131-Iodine using N-succinimidyl-4-guanidinomethyl-3-[I-131]iodobenzbate ([I-131]SGMIB) or a suitable derivative or variant thereof.

In some embodiments of the pharmaceutical composition, the radiolabelled, monovalent $V_{HH}$ or a functional fragment thereof has at least 80% amino acid identity with at least one of the amino acid sequences of SEQ ID NOs:7 and 8 and is labeled with 131-Iodine using N-succinimidyl-4-guanidinomethyl-3-[I-131]iodobenzbate ([I-131]SGMIB) or a suitable derivative or variant thereof.

In some embodiments of the pharmaceutical composition, the radiolabelled, monovalent $V_{HH}$ or a functional fragment thereof is identical with at least one of the amino acid sequences of SEQ ID NOs:7 and 8 and is labeled with 131-Iodine using N-succinimidyl-4-guanidinomethyl-3-[I-131]iodobenzbate ([I-131]SGMIB) or a suitable derivative or variant thereof.

In some embodiments of the pharmaceutical composition, the radiolabelled, monovalent $V_{HH}$ or functional fragment thereof is non-lifetime extended.

In some embodiments of the pharmaceutical composition, the radiolabelled, monovalent $V_{HH}$ or functional fragment thereof is devoid of a carboxy-terminal polypeptide tag.

In some aspects, the disclosure provides a radiolabelled heavy chain variable domain derived from a heavy chain antibody ($V_{HH}$), or a functional fragment thereof, which specifically binds to a target protein that is present on a cancer cell for use in a method for the prevention and/or treatment of cancer.

In other aspects, the disclosure provides a radiolabelled heavy chain variable domain derived from a heavy chain antibody ($V_{HH}$), or a functional fragment thereof, which specifically binds to a target protein that is present on a solid tumor for use in a method for the prevention and/or treatment of cancer.

In some aspects, the disclosure provides a pharmaceutical composition comprising at least one radiolabelled $V_{HH}$ or a functional fragment thereof, which $V_{HH}$ or fragment specifically binds to a target protein present on and/or specific for a cancer cell, for use in a method for the prevention and/or treatment of cancer.

In other aspects, the disclosure provides a pharmaceutical composition comprising at least one radiolabelled $V_{HH}$ or a functional fragment thereof, which $V_{HH}$ or fragment specifically binds to a target protein present on and/or specific for a solid tumor, for use in a method for the prevention and/or treatment of cancer.

In some embodiments of any one of the radiolabelled $V_{HH}$ or functional fragments thereof or pharmaceutical composition for use as described herein, said $V_{HH}$ or functional fragment thereof specifically binds to HER2.

In some embodiments of any one of the radiolabelled $V_{HH}$ or functional fragments thereof or pharmaceutical composition for use as described herein, said $V_{HH}$ or functional fragment thereof does not compete with the monoclonal antibody Trastuzumab (Herceptin®) or the monoclonal antibody Pertuzumab (Perjeta®) for binding to HER2, as determined using a suitable competition assay.

In some embodiments of any one of the radiolabelled $V_{HH}$ or functional fragments thereof or pharmaceutical composition for use as described herein, said radiolabelled $V_{HH}$ or functional fragment thereof is administered to a subject in need thereof having a calculated mean effective dose of between 0.002 and 0.1 mSv/MBq in said subject.

In some embodiments of any one of the radiolabelled $V_{HH}$ or functional fragments thereof or pharmaceutical composition for use as described herein, said radiolabelled $V_{HH}$ or functional fragment thereof is administered to a subject in need thereof at an administration interval of between once a day and once a month or between once a month and once a year.

In some embodiments of any one of the radiolabelled $V_{HH}$ or functional fragments thereof or pharmaceutical composition for use as described herein, said radiolabelled $V_{HH}$ or functional fragment thereof binds to said target protein that is present on and/or specific for a solid tumor or cancer cell with an affinity of less than 5 nM.

In some embodiments of any one of the radiolabelled $V_{HH}$ or functional fragments thereof or pharmaceutical composition for use as described herein, said radiolabelled $V_{HH}$ or functional fragment thereof is labelled with a radio-isotope chosen from the group consisting of α-emitting radioisotopes and β-emitting radioisotopes.

In some embodiments of any one of the radiolabelled $V_{HH}$ or functional fragments thereof or pharmaceutical composition for use as described herein, said radiolabelled $V_{HH}$ or functional fragment thereof is labelled with a radio-isotope chosen from the group consisting of Actinium-225, Astatine-211, Bismuth-212, Bismuth-213, Caesium-137, Chromium-51, Cobalt-60, Dysprosium-165, Erbium-169, Fermium-255, Gold-198, Holium-166, Iodine-125, Iodine-131, Iridium-192, Iron-59, Lead-212, Lutetium-177, Molydenum-99, Palladium-103, Phosphorus-32, Potassium-42, Rhenium-186, Rhenium-188, Samarium-153, Technitium-99m, Radium-223, Ruthenium-106, Sodium-24, Strontium-89, Terbium-149, Thorium-227, Xenon-133, Ytterbium-169, Ytterbium-177, Yttrium-90.

In some embodiments of any one of the radiolabelled $V_{HH}$ or functional fragments thereof or pharmaceutical composition for use as described herein, said radiolabelled $V_{HH}$ or functional fragment thereof is labelled with 131-Iodine.

In some embodiments of any one of the radiolabelled $V_{HH}$ or functional fragments thereof or pharmaceutical composition for use as described herein, said radiolabelled $V_{HH}$ or functional fragment thereof is labelled with 131-Iodine using N-succinimidyl-4-guanidinomethyl-3-[I-131]iodobenzbate ([I-131]SGMIB) or a suitable derivative or variant thereof.

In some embodiments of any one of the radiolabelled $V_{HH}$ or functional fragments thereof or pharmaceutical composition for use as described herein, said $V_{HH}$ comprises one of the CDR combinations chosen from the group comprising:
  a CDR1 region having SEQ ID NO:1, a CDR2 region having SEQ ID NO:2, and a CDR3 region having SEQ ID NO:3, and/or
  a CDR1 region having SEQ ID NO:4, a CDR2 region having SEQ ID NO:5, and a CDR3 region having SEQ ID NO:6.

In some embodiments of any one of the radiolabelled $V_{HH}$ or functional fragments thereof or pharmaceutical composition for use as described herein, said $V_{HH}$ has at least 80% amino acid identity with at least one of the amino acid sequences of SEQ ID NO's:7 or 8 or a functional fragment thereof.

In some embodiments of any one of the radiolabelled $V_{HH}$ or functional fragments thereof or pharmaceutical composition for use as described herein, said $V_{HH}$ is identical with at least one of the amino acid sequences of SEQ ID NO's: 7 or 8 or a functional fragment thereof.

In some embodiments of any one of the radiolabelled $V_{HH}$ or functional fragments thereof or pharmaceutical composition for use as described herein, said cancer is breast cancer.

In some embodiments of any one of the radiolabelled $V_{HH}$ or functional fragments thereof or pharmaceutical composition for use as described herein, said prevention and/or treatment of cancer is performed in combination with immunotherapy.

In some embodiments of any one of the radiolabelled $V_{HH}$ or functional fragments thereof or pharmaceutical composition for use as described herein, said radiolabelled $V_{HH}$ or functional fragment thereof is administered to a subject in need thereof intravenously, intrathecally or intraperitoneally.

In some embodiments of any one of the radiolabelled $V_{HH}$ or functional fragments thereof or pharmaceutical composition for use as described herein, said $V_{HH}$ is present in a monovalent format.

In some embodiments of any one of the radiolabelled $V_{HH}$ or functional fragments thereof or pharmaceutical composition for use as described herein, said $V_{HH}$ or said functional fragment thereof is devoid of a cysteine-containing tag, preferably a GGC-tag.

In some embodiments of any one of the radiolabelled $V_{HH}$ or functional fragments thereof or pharmaceutical composition for use as described herein, said $V_{HH}$ or said functional fragment thereof is non-lifetime extended.

In some embodiments of any one of the radiolabelled $V_{HH}$ or functional fragments thereof or pharmaceutical composition for use as described herein, said VHH or said functional fragment thereof is devoid of a carboxy-terminal polypeptide tag, preferably wherein said VHH or said functional fragment thereof is untagged.

In one aspect, the present disclosure provides radiolabelled heavy chain variable domains derived from heavy chain antibodies ($V_{HH}$'s) or functional fragments thereof, which specifically bind to a target protein that is present on and/or specific for a solid tumor (also referred to herein as a tumor-specific antigen) for use in a method for the prevention and/or treatment of cancer.

In another aspect, the present disclosure provides radiolabelled heavy chain variable domains derived from heavy chain antibodies ($V_{HH}$'s) or functional fragments thereof, which specifically bind to a target protein that is present on and/or specific for a cancer cell (also referred to herein as a cancer cell-specific antigen) for use in a method for the prevention and/or treatment of cancer.

In certain embodiments, the present disclosure provides a radiolabelled $V_{HH}$ or functional fragments thereof as disclosed herein for use in the prevention and/or treatment of cancer by administering to a subject in need thereof the radiolabelled $V_{HH}$ or functional fragments thereof at a dose of between 10 µg and 1000 µg of $V_{HH}$.

In certain other embodiments, prevention and treatment of cancer is achieved by administering a radiolabelled $V_{HH}$ or functional fragments thereof as disclosed herein to a subject in need thereof, characterized in that the $V_{HH}$ or functional fragments thereof has a calculated mean effective dose of between 0.002 and 0.1 mSv/MBq in a subject.

In particular embodiments, the present disclosure provides a radiolabelled $V_{HH}$ or functional fragments thereof as disclosed herein for use in the prevention and/or treatment of cancer by administering to a subject in need thereof, the radiolabelled $V_{HH}$ or functional fragments thereof at an administration interval of between once a day and once a month or between once a month and once a year.

In particular embodiments, the $V_{HH}$'s or functional fragments thereof as disclosed herein specifically bind to a target protein that is present on and/or specific for a solid tumor, such as a tumor-specific antigen. In further particular embodiments, the $V_{HH}$'s or functional fragments thereof as disclosed herein specifically bind to a target protein that is present on and/or specific for a solid tumor with an affinity of less than 5 nM, such as between 1 and 5 nM, preferably between 2 and 3 nM.

In further particular embodiments, the $V_{HH}$'s or functional fragments thereof as disclosed herein specifically bind to a target protein that is present on and/or specific for a cancer cell, such as a cancer cell-specific antigen. In further particular embodiments, the $V_{HH}$'s or functional fragments thereof as disclosed herein specifically bind to a target protein that is present on and/or specific for a cancer cell with an affinity of less than 5 nM, such as between 1 and 5 nM, preferably between 2 and 3 nM.

In further particular embodiments, the $V_{HH}$'s or functional fragments thereof as disclosed herein specifically bind to HER2. In further particular embodiments, the $V_{HH}$'s or functional fragments thereof as disclosed herein specifically bind to HER2 with an affinity of less than 5 nM, such as between 1 and 5 nM, preferably between 2 and 3 nM.

In certain embodiments, the HER2 targeting $V_{HH}$'s or functional fragments thereof as disclosed herein do not compete with Trastuzumab and Pertuzumab for binding to HER2, as determined using a suitable competition assay. This advantageously allows to use the HER2 targeting $V_{HH}$'s or functional fragments thereof as disclosed herein in combination with Trastuzumab (Herceptin®) and/or Pertuzumab (Perjeta®) in a method for the prevention and/or treatment of cancer, more particularly a HER2-positive cancer such as HER2-positive breast cancer.

In particular embodiments, the radio-labelled HER2 targeting $V_{HH}$'s or functional fragments thereof as disclosed herein are specifically directed against a binding site on HER2, which is different from (i.e. is not) domain IV of HER2, more particularly the C-terminus of domain IV of HER2. In particular embodiments, the radio-labelled HER2 targeting $V_{HH}$'s or functional fragments thereof as disclosed herein are specifically directed against a binding site on HER2, which is different from (i.e. is not) domain II of HER2. In particular embodiments, the radio-labelled $V_{HH}$'s or functional fragments thereof as disclosed herein are specifically directed against a binding site on HER2, which is different from (i.e. is not) domain IV of HER2, more particularly the C-terminus of domain IV of HER2, and domain II of HER2.

In further specific embodiments, the radiolabelled $V_{HH}$'s or functional fragments thereof as disclosed herein are labelled with a radio-isotope chosen from the group consisting of α-emitting radioisotopes and β-emitting radioisotopes, including but not limited to a radioisotope chosen from the group consisting of Actinium-225, Astatine-211, Bismuth-212, Bismuth-213, Caesium-137, Chromium-51, Cobalt-60, Dysprosium-165, Erbium-169, Fermium-255, Gold-198, Holium-166, Iodine-125, Iodine-131, Iridium-192, Iron-59, Lead-212, Lutetium-177, Molydenum-99, Palladium-103, Phosphorus-32, Potassium-42, Rhenium-186, Rhenium-188, Samarium-153, Technitium-99m, Radium-223, Ruthenium-106, Sodium-24, Strontium-89, Terbium-149, Thorium-227, Xenon-133, Ytterbium-169, Ytterbium-177, Yttrium-90. In still further particular embodiments, the radiolabelled $V_{HH}$'s or functional fragments thereof as disclosed herein are labelled with Iodine-131.

In certain specific embodiments, the disclosure provides radiolabelled $V_{HH}$'s or functional fragments thereof specifically binding to a tumor cell-specific antigen or to a cancer cell-specific antigen for use in the prevention and/or treatment of cancer, wherein said radiolabelled $V_{HH}$ or functional fragment thereof is labelled with 131-Iodine using N-succinimidyl-4-guanidinomethyl-3-[I-131]iodobenzbate ([I-131]SGMIB) or a suitable derivative or variant thereof.

In certain specific embodiments, the disclosure provides radiolabelled $V_{HH}$'s or functional fragments thereof specifically binding to a tumor cell-specific antigen or to a cancer cell-specific antigen for use in the prevention and/or treatment of cancer, wherein said radiolabelled $V_{HH}$ or functional fragment thereof is labelled with 211-Astatine using N-succinimidyl-4-guanidinomethyl-3-[211At]astatobenzoate ([211At]SGMAB) or a suitable derivative or variant thereof.

In specific embodiments, the amino acid sequence of the radio-labelled $V_{HH}$'s or functional fragments thereof as disclosed herein, which specifically interact with solid tumors, comprises one or more of the CDR combinations chosen from the group comprising:
  a CDR1 region having SEQ ID NO: 1, a CDR2 region having SEQ ID NO: 2, and a CDR3 region having SEQ ID NO: 3, and/or
  a CDR1 region having SEQ ID NO: 4, a CDR2 region having SEQ ID NO: 5, and a CDR3 region having SEQ ID NO: 6.

In further specific embodiments, the amino acid sequence of the radio-labelled $V_{HH}$'s as disclosed herein, which specifically interact with a solid tumor antigen, has at least 80% amino acid identity with at least one of the amino acid sequences of SEQ ID NO's: 7 or 8 or functional fragments thereof.

In yet further specific embodiments, the amino acid sequence of the radio-labelled $V_{HH}$'s as disclosed herein, which specifically interact with a tumor-specific antigen, is identical with at least one of the amino acid sequences of SEQ ID NO's: 7 or 8 or functional fragments thereof.

In further specific embodiments, the amino acid sequence of the radio-labelled $V_{HH}$'s as disclosed herein, which specifically interact with a cancer cell-specific antigen, has at least 80% amino acid identity with at least one of the amino acid sequences of SEQ ID NO's: 7 or 8 or functional fragments thereof.

In yet further specific embodiments, the amino acid sequence of the radio-labelled $V_{HH}$'s as disclosed herein, which specifically interact with a cancer cell-specific antigen, is identical with at least one of the amino acid sequences of SEQ ID NO's: 7 or 8 or functional fragments thereof.

In certain embodiments, the present disclosure provides a radiolabelled $V_{HH}$ or functional fragments thereof as disclosed herein for use in the prevention and/or treatment of cancer, wherein said cancer is breast cancer.

In certain other embodiments, the present disclosure provides a radiolabelled $V_{HH}$ or functional fragments thereof as disclosed herein for use in the prevention and/or treatment of cancer, wherein said prevention and/or treatment of cancer is performed in combination with immunotherapy.

In certain other embodiments, prevention and treatment of cancer is achieved by administering a radiolabelled $V_{HH}$ or functional fragments thereof as disclosed herein to a subject in need thereof intravenously, intraperitoneally or intrathecally.

In further specific embodiments, the amino acid sequence of the radio-labelled $V_{HH}$'s or functional fragments thereof as disclosed herein, which specifically interact with a solid tumor antigen or with a cancer cell-specific antigen are present in a monovalent format. In yet further embodiments, the $V_{HH}$'s or functional fragments thereof as disclosed herein are devoid of a tag that induces multimerization such as dimerization of the $V_{HH}$'s or the functional fragments, more particularly a cysteine-containing tag such as a GGC tag.

In certain embodiments, the radio-labelled $V_{HH}$'s or functional fragments thereof as disclosed herein, which specifically interact with a solid tumor antigen or with a cancer cell-specific antigen are present in a non-lifetime extended format.

In certain embodiments, the radio-labelled $V_{HH}$'s or functional fragments thereof as disclosed herein, which specifically interact with a solid tumor antigen or with a cancer cell-specific antigen are devoid of a carboxy-terminal polypeptide tag. $V_{HH}$'s without a carboxy-terminal polypeptide tag are advantageous over carboxy-terminal polypeptide tagged $V_{HH}$'s, such as His-tagged $V_{HH}$'s and Myc-His-tagged $V_{HH}$'s in that they are less retained in the kidneys.

In a further aspect, the present disclosure provides polypeptides comprising at least one radiolabelled $V_{HH}$ or at least one functional fragment thereof, which $V_{HH}$ or functional fragments thereof specifically binds to a target protein present on and/or specific for a solid tumor and/or specific for a cancer cell, for use in a method for the prevention and/or treatment of cancer.

In yet a further aspect, the present disclosure provides pharmaceutical compositions comprising at least one radiolabelled $V_{HH}$ or functional fragments thereof, which $V_{HH}$ or functional fragments thereof specifically binds to a target protein present on and/or specific for a solid tumor and/or specific for a cancer cell, for use in a method for the prevention and/or treatment of cancer. In further specific embodiments, the pharmaceutical compositions as disclosed herein further comprise a pharmaceutically acceptable carrier and/or one or more suitable adjuvants.

BRIEF DESCRIPTION OF THE DRAWINGS

The above disclosure will now be further described by means of the following non-limiting Figures, in which the figures show:

FIGS. 5A-5C: Prophylactic treatment of 5T2MM mice with $^{177}$Lutetium-conjugated R3B23 $V_{HH}$. (a) Sagittal view of the fused SPECT/micro-CT scan images of 5T2MM mice treated for 5 weeks with $^{177}$Lu-R3B23 (n=6), $^{177}$Lu-cAbBcII10 (n=6) or saline solution (untreated; n=3). For imaging purposes, all mice were injected with $^{99m}$Tc-R3B23 $V_{HH}$, and SPECT/micro-CT scan images were acquired 1 h post injection. The National Institutes Health color scale is used, and all images are equally scaled down to 20% relative to maximum activity in image. One representative image of each group is shown. (b) The relative amount of $^{99m}$Tc-R3B23 tracer uptake in the heart after 5 weeks of treatment with $^{177}$Lu-R3B23. (c) Weight of spleen after 7 weeks of treatment with $^{177}$Lu-R3B23. *P<0.05; P<0.005; *P<0.0005; n.s., not significant.

Ex vivo 5T2MM cells were incubated with control $V_{HH}$ cAbBcII10, anti-5T2MMid $V_{HH}$'s or anti-5T2MMid antibody. $V_{HH}$ binding was detected by anti-HA antibody and anti-IgG1 APC antibody. Anti-5T2MMid antibody was directly detected by anti-IgG APC. One representative profile for each $V_{HH}$ is shown (n=3). Membrane staining with anti-5T2MMid MoAb revealed that 66.8% of the total population was positive for the 5T2MMid. When compared to staining with anti-5T2MMid MoAb, $V_{HH}$'s R2A6, R2A57 and R3B41 were able to detect 85.2%, 28.7% and 24.1% (respectively) of the 5T2MMid positive population. $V_{HH}$ R3B23 detected 98.7% of the 5T2MMid positive population, whereas control $V_{HH}$ cAbBcII10 did not stain these cells.

Figure 10:
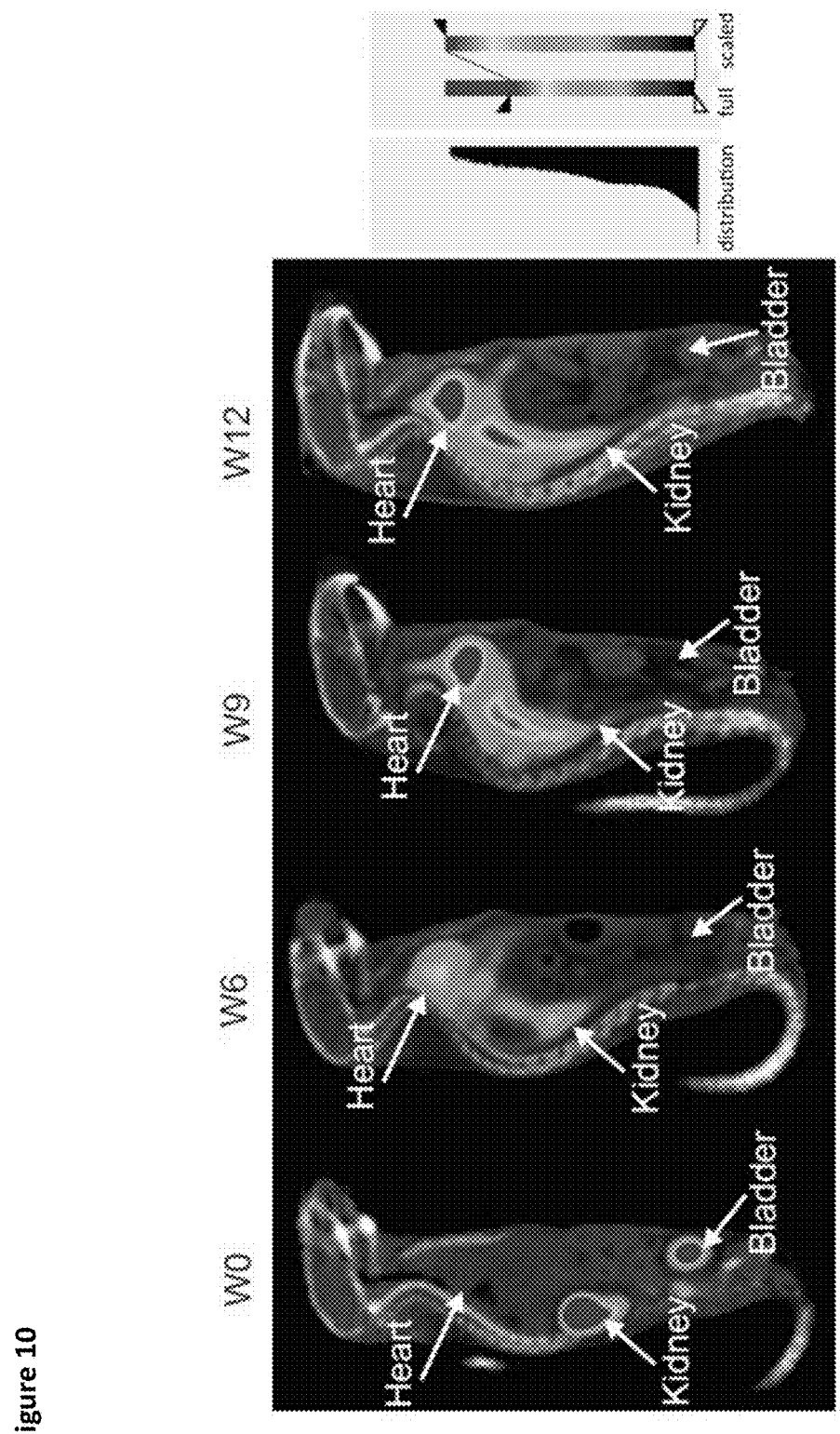

FIG. 10: Monitoring of disease progression using 99mTc-labeled R3B23 $V_{HH}$.

Sagittal views of fused SPECT/micro-CT scans of a mouse scanned 0, 6, 9 and 12 weeks after inoculation with 5T2MM tumor cells. As an indirect method to noninvasively measure tracer blood levels, we quantified the % IA/cm$^3$ in a ROI in the heart. NIH color scale is used and all images are equally scaled down to 75% relative to maximum activity in image, corrected for injected activity. Starting at week 6 after 5T2MM cell inoculation we were able to quantify tracer uptake in the blood (0.83±0.06%) and this value increased at week 9 (0.99±0.04%) and remained constant (0.99±0.02%) at week 12. Blood-pool levels were very low in naïve mice (0.0146±0.0004%). One representative follow-up study is shown (n=5).

FIGS. 11A-11E: (Radio-)chromatographic analyses of various untagged 2Rs15d conjugates. (A) unconjugated $V_{HH}$, (B) CHX-A"-DTPA-2Rs15d, (C) 1B4M-DTPA-2Rs15d, (D) $^{177}$Lu-DTPA-2Rs15d, (E) $^{111}$In-DTPA-2Rs15d;

(A-C) SEC on Superdex 10/30, (D) radio-SEC on Superdex 75 5/150GL; (E) radio-HPLC on PLRP-S. The R-times of the major peaks are shown in each graph.

FIGS. 12A-12E: Accumulation of radioactivity in kidneys in function of time after injection of various $^{111}$In-labeled 2Rs15d formats in healthy Wistar rats (n=3); (A-D) A selection of images are shown obtained by gamma camera dynamic scintigraphy; (A) 2Rs15d-Myc-His-tag, (B) 2Rs15d-His-tag, (C) untagged 2Rs15d, (D) untagged 2Rs15d coinfused with 80 mg/kg Gelofusin. (E) Time-activity curves of renal retention in rats (n=3 per condition). Lowest accumulation in kidneys was observed for the $^{111}$In-labeled untagged 2Rs15d that was coinfused with 150 mg/kg Gelofusin.

Figure 13:
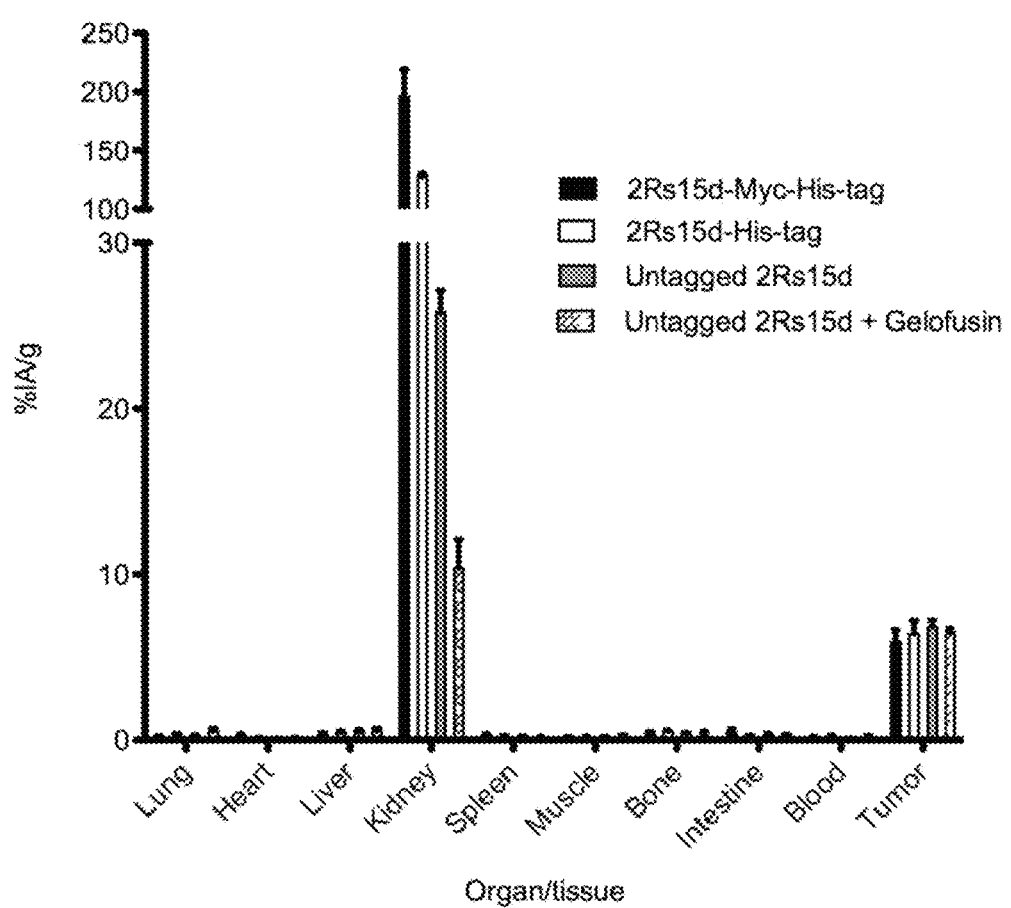

FIG. 13: Ex vivo biodistribution analyses of $^{177}$Lu-labeled 2Rs15d constructs in HER2$^{pos}$ tumor xenografted mice, at 1 h p.i. Animals were injected with 21.5 MBq (4 µg) radioconjugates. Columns, mean (n=3); bars, SD. Kidney accumulation decreased significantly by removing the C-terminal amino acid tag, and by a coinfusion with Gelofusin. Tumor targeting was not affected.

Figure 14A:
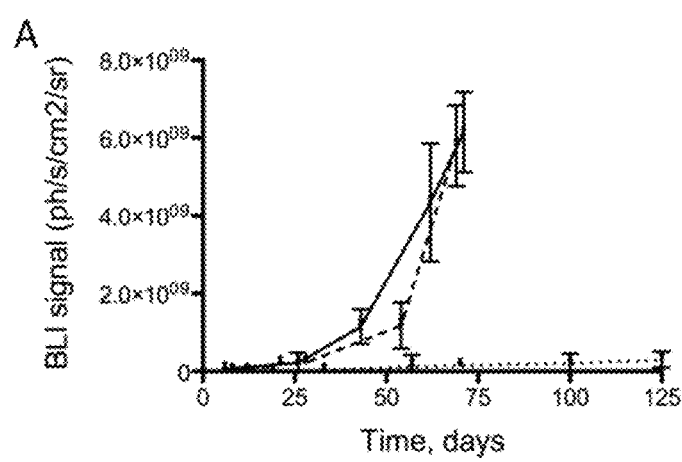
Figure 14B:
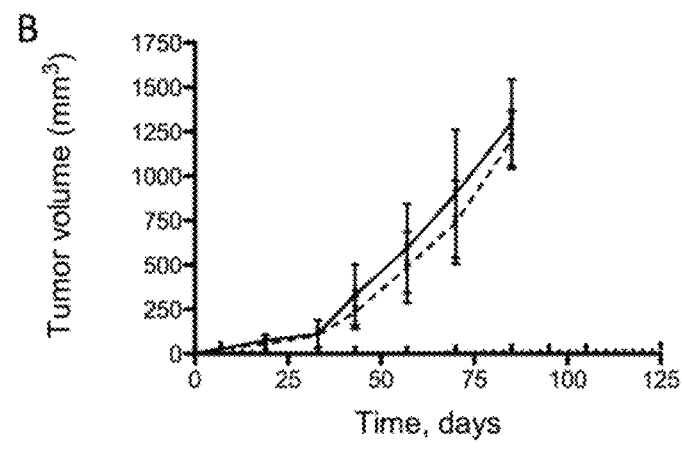

FIGS. 14A-B: Tumor growth monitoring during targeted radionuclide therapy. Tumor volumes were quantified using (A) bioluminescence imaging (ph/s/cm$^2$/sr) or (B) caliper measurements (mm$^3$), in function of time (days). Animals (n=8 per group) were treated with a weekly injection of untagged $^{177}$Lu-labeled 2Rs15d (20.7±0.4 MBq) and in the control groups with PBS or $^{177}$Lu-labeled BCII10 (19.3±0.8 MBq). All treatments occurred with a 150 mg/kg Gelofusin coinjection. In terms of tumor growth, important differences were observed between both control groups and the treated group, for both caliper and bioluminescence measurements.

Figure 15A:
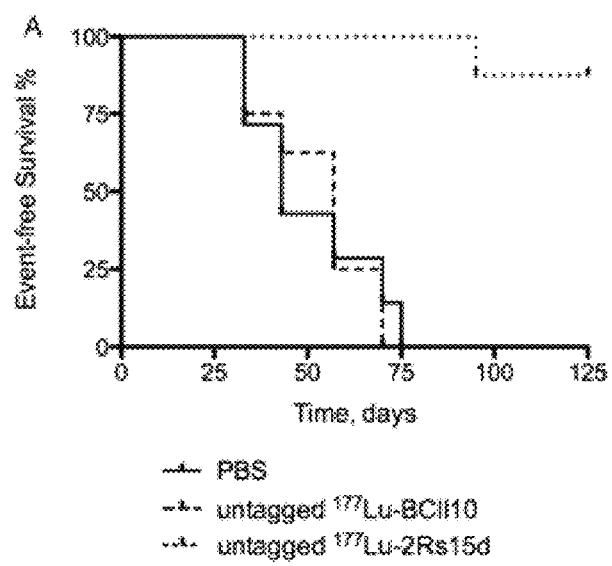
Figure 15B:
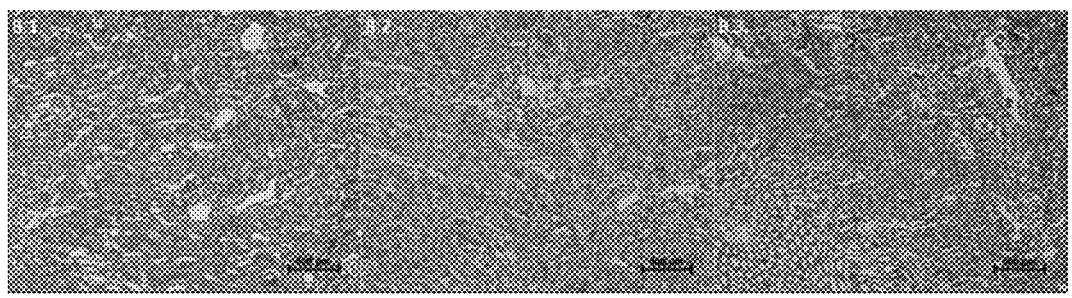

FIGS. 15A-15B: (A) Event-free survival during targeted radionuclide therapy. Events are defined as 1. Mortality; 2. >20% weight loss; 3. Ulcerating tumor tissue; 4. Tumor volume>250 mm$^3$. Animals (n=8 per group) were treated with a weekly injection of untagged $^{177}$Lu-labeled 2Rs15d (20.7±0.4 MBq) and in the control groups with PBS or $^{177}$Lu-labeled BCII10 (19.3±0.8 MBq). All treatments occurred with a 150 mg/kg Gelofusin coinjection. (B) Renal histopathology. Kidneys of $^{177}$Lu-dosed animal groups were compared to the PBS-treated animal group. Sections were H&E stained and examined for evidence of renal toxicity. No differences in renal histology were observed between the animal groups that received (B.1) PBS, (B.2) untagged $^{177}$Lu-labeled BCII10 or (B.3) untagged $^{177}$Lu-labeled 2Rs15d.

Figures 16A, 16B, 16C:
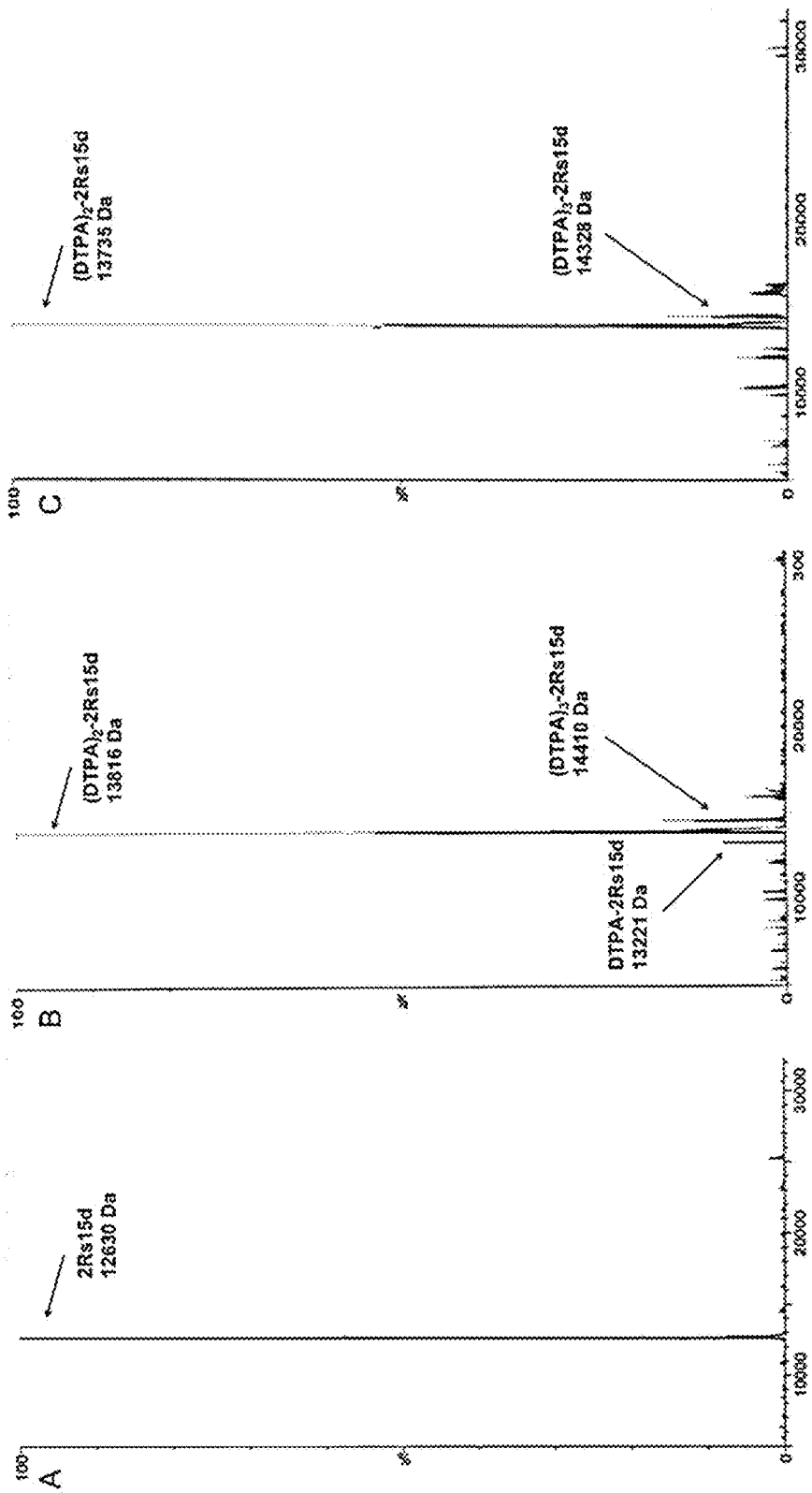

FIGS. 16A-16C: ESI-Q-ToF-MS analysis of (A) untagged 2Rs15d, (B) untagged CHX-A"-DTPA-2Rs15d and (C) untagged 1B4M-DTPA-2Rs15d. The reaction of CHX-A"-DTPA to untagged 2Rs15d revealed a mixture of 1, 2 and 3 DTPA conjugated to untagged 2Rs15d. Using 1B4M-DTPA, a mixture of 2 and 3 DTPA to 2Rs15d was observed. The dominant conjugation ratio (chelator:V$_{HH}$) for both 1B4M-DTPA and CHX-A"-DTPA to untagged 2Rs15d is 2:1.

Figure 17A:
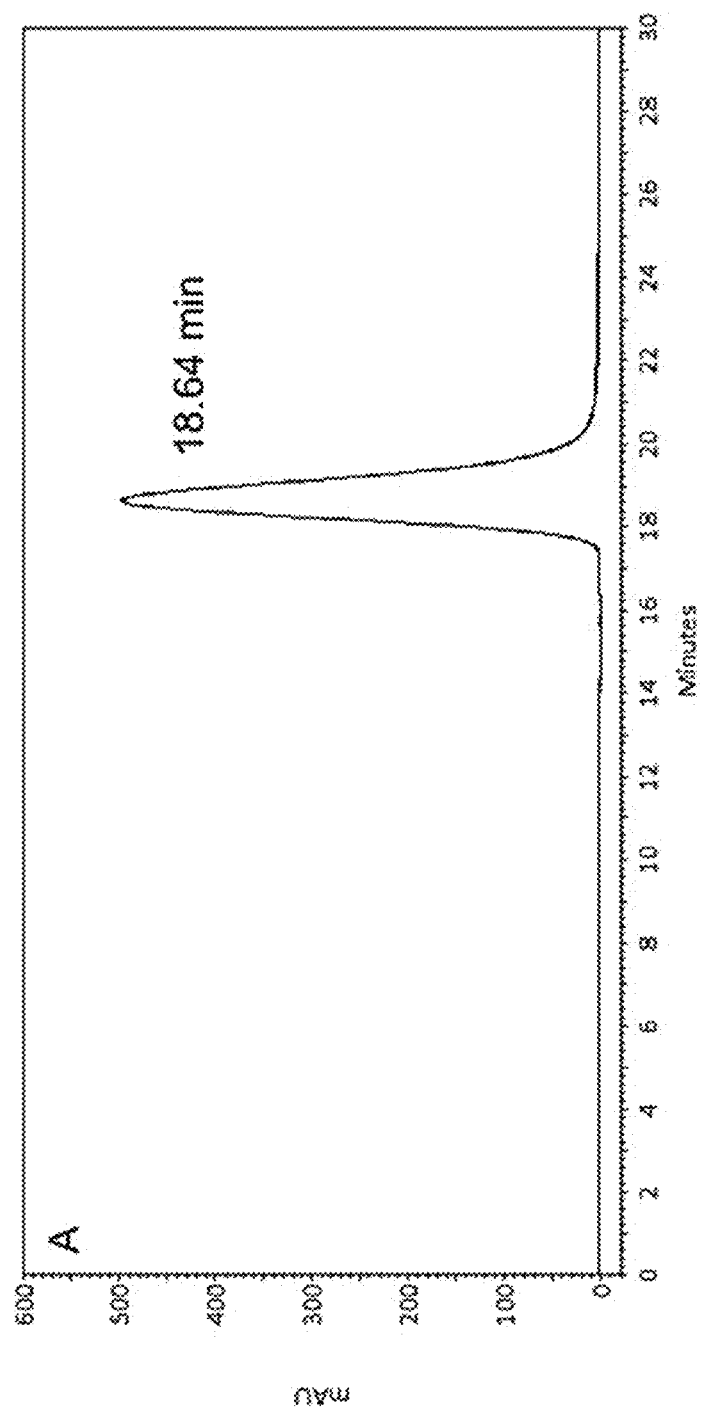
Figure 17B:
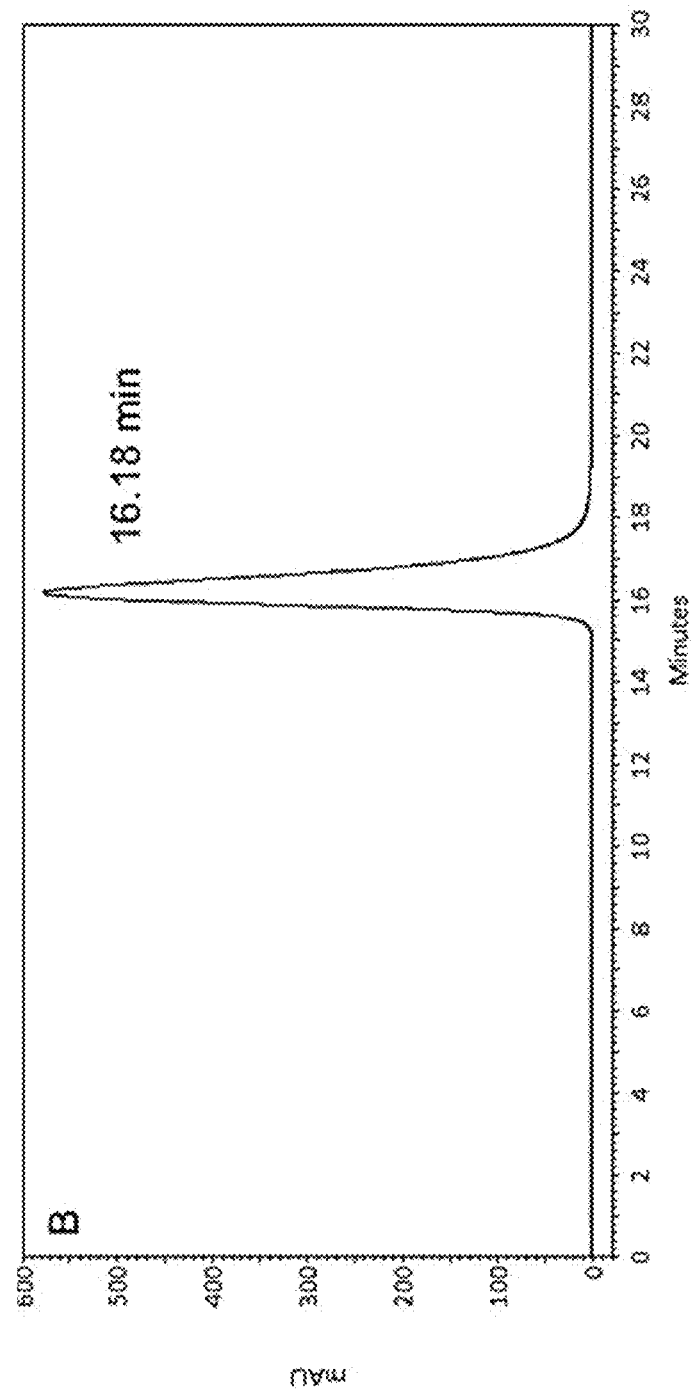
Figure 17C:
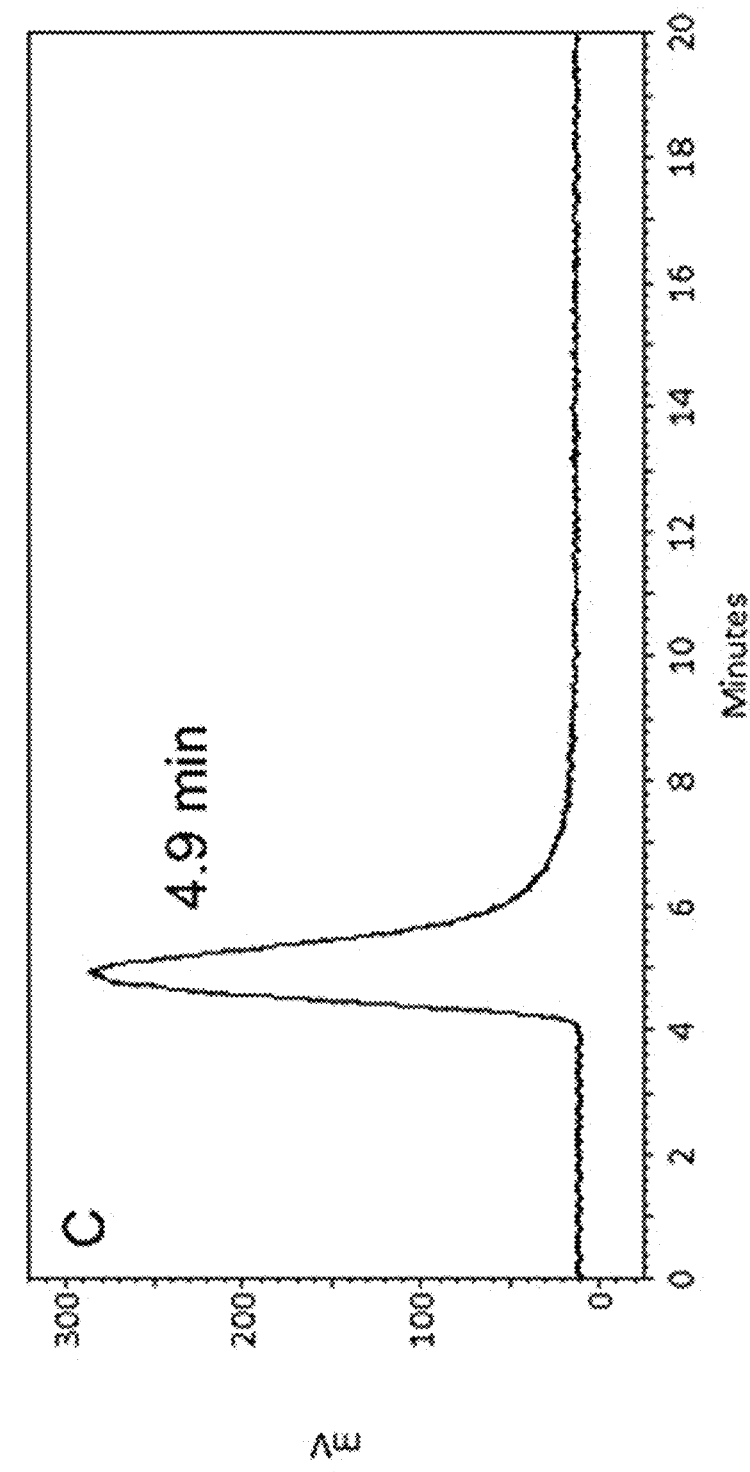

FIGS. 17A-17C: (Radio-)chromatographic analyses of Trastuzumab conjugates. (A) unconjugated Trastuzumab, (B) 1B4M-DTPA-Trastuzumab, (C)$^{177}$Lu-DTPA-Trastuzumab; (A,B) SEC on Superdex 75 10/30, (B) radio-SEC on Superdex 75 5/150GL; The R-times of the major peaks are shown in each graph.

Figure 18A:
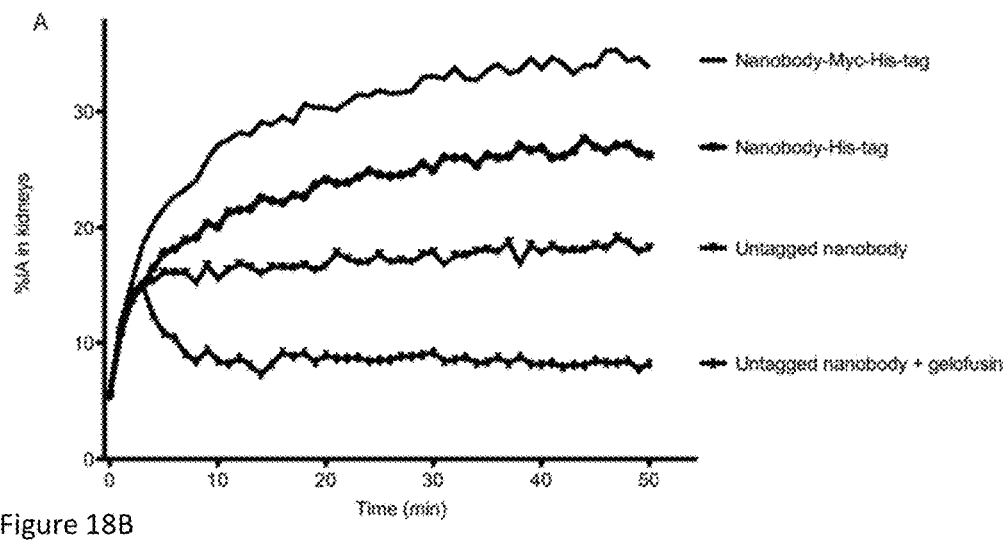
Figure 18B:
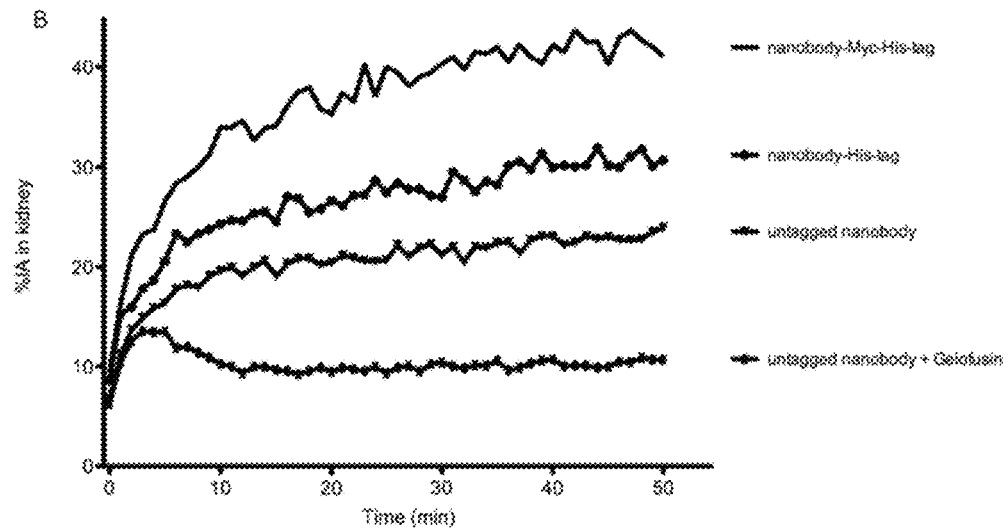

FIGS. 18A-18B: Accumulation of radioactivity in kidneys in healthy Wistar rats (n=3 per condition) in function of time, after injecting $^{111}$In-labeled anti-HER2 V$_{HH}$'s and gamma camera dynamic scintigraphy. (A) V$_{HH}$ 2 Rb17c, (B) V$_{HH}$ 1 R136d.

Figure 19:
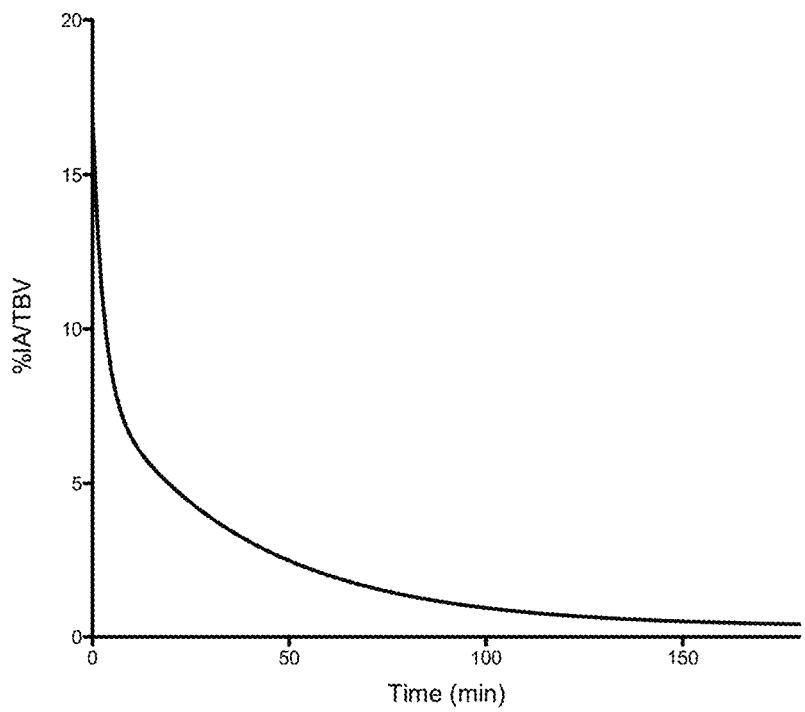

FIG. 19: Blood clearance of untagged monovalent [131I] SGMIB-labeled anti-HER2 VHH 2Rs15d in male C57bl/6 mice. Values ware expressed as % injected Activity/Total Blood Volume (% IA/TBV).

Figure 20:
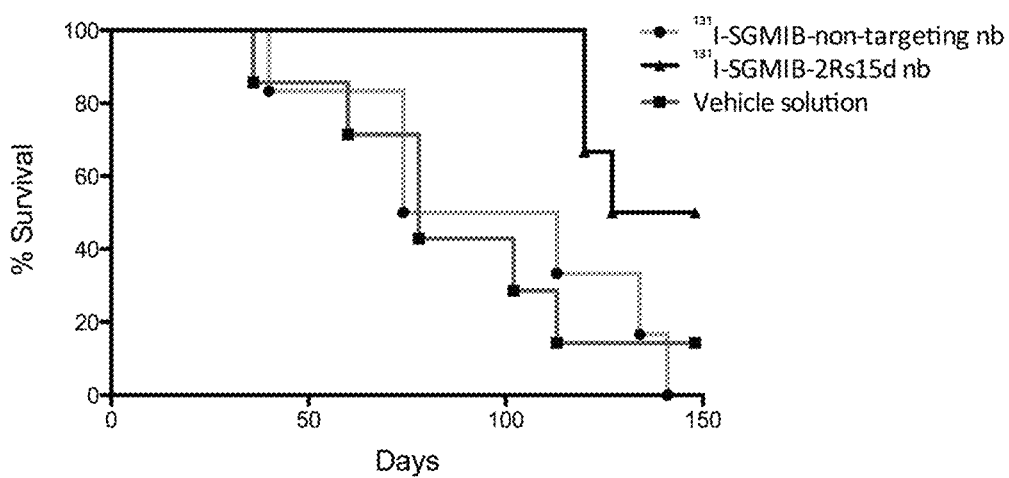

FIG. 20: Therapeutic effect of untagged monovalent [$^{131}$I] SGMIB-labeled anti-HER2 VHH 2Rs15d. Animals (n=6/7 per group) were treated with a weekly injection of untagged monovalent [$^{131}$I]SGMIB-labeled anti-HER2 VHH 2Rs15d ($^{131}$I-SGMIB-2Rs15d nb) and in the control groups with vehicle solution (vehicle solution) or untagged monovalent [$^{131}$I]SGMIB-labeled non-targeting control VHH ($^{131}$I-SGMIB-non-targeting nb). Animals were euthanized when more than 20% weight loss or a tumor volume of more than 1 cm$^3$ was reached. Survival of the animals in the different groups is shown.

DETAILED DESCRIPTION OF THE INVENTION

[Definitions]
[General Definitions]

The present invention will be described with respect to particular embodiments but the invention is not limited thereto but only by the claims. Any reference signs in the claims shall not be construed as limiting the scope. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2$^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

As used herein, the singular forms 'a', 'an', and 'the' include both singular and plural referents unless the context clearly dictates otherwise.

The terms 'comprising', 'comprises' and 'comprised of' as used herein are synonymous with 'including', 'includes' or 'containing', 'contains', and are inclusive or open-ended and do not exclude additional, non-recited members, elements or method steps.

The recitation of numerical ranges by endpoints includes all numbers and fractions subsumed within the respective ranges, as well as the recited endpoints.

The term 'about' as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier 'about' refers is itself also specifically, and preferably, disclosed.

As used herein, amino acid residues will be indicated either by their full name or according to the standard three-letter or one-letter amino acid code.

As used herein, the terms 'polypeptide', 'protein', 'peptide', and 'amino acid sequence' are used interchangeably, and refer to a polymeric form of amino acids of any length, which can include coded and non-coded amino acids, chemically or biochemically modified or derivatized amino acids, and polypeptides having modified peptide backbones.

As used herein, the terms 'nucleic acid molecule', 'polynucleotide', 'polynucleic acid', 'nucleic acid' are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term 'homology' denotes at least secondary structural similarity between two macromolecules, particularly between two polypeptides or polynucleotides, from same or different taxons, wherein said similarity is due to shared ancestry. Hence, the term 'homologues' denotes so-related macromolecules having said secondary and optionally tertiary structural similarity. For comparing two or more nucleotide sequences, the '(percentage of) sequence identity' between a first nucleotide sequence and a second nucleotide sequence may be calculated using methods known by the person skilled in the art, e.g. by dividing the number of nucleotides in the first nucleotide sequence that are identical to the nucleotides at the corresponding positions in the second nucleotide sequence by the total number of nucleotides in the first nucleotide sequence and multiplying by 100% or by using a known computer algorithm for sequence alignment such as NCBI Blast. In determining the degree of sequence identity between two amino acid sequences, the skilled person may take into account so-called 'conservative' amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions will be clear to the person skilled in the art. Amino acid sequences and nucleic acid sequences are said to be 'exactly the same' if they have 100% sequence identity over their entire length.

The term 'affinity', as used herein, refers to the degree to which a polypeptide, in particular an immunoglobulin, such as an antibody, or an immunoglobulin fragment, such as a $V_{HH}$, binds to an antigen so as to shift the equilibrium of antigen and polypeptide toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the protein binding domain and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M, such as lower than $10^{-9}$ M.

The terms 'specifically bind' and 'specific binding', as used herein, generally refers to the ability of a polypeptide, in particular an immunoglobulin, such as an antibody, or an immunoglobulin fragment, such as a $V_{HH}$ or functional fragments thereof, to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold).

Accordingly, an amino acid sequence, in particular an antibody fragment, such as a $V_{HH}$ or functional fragments thereof, as disclosed herein is said to 'specifically bind to' a particular target when that amino acid sequence has affinity for, specificity for and/or is specifically directed against that target (or for at least one part or fragment thereof).

An amino acid sequence, in particular an antibody fragment, such as a $V_{HH}$ or functional fragments thereof, as disclosed herein is said to be 'specific for a first target antigen of interest as opposed to a second target antigen of interest' when it binds to the first target antigen of interest with an affinity that is at least 5 times, such as at least 10 times, such as at least 100 times, and preferably at least 1000 times higher than the affinity with which that amino acid sequence as disclosed herein binds to the second target antigen of interest. Accordingly, in certain embodiments, when an amino acid sequence as disclosed herein is said to be 'specific for' a first target antigen of interest as opposed to a second target antigen of interest, it may specifically bind to (as defined herein) the first target antigen of interest, but not to the second target antigen of interest.

The 'specificity' of an amino acid sequence, in particular an antibody fragment, such as a $V_{HH}$, or functional fragments thereof as disclosed herein can be determined based on affinity and/or avidity. The 'affinity' of an amino acid sequence as disclosed herein is represented by the equilibrium constant for the dissociation of the amino acid sequence as disclosed herein and the target protein of interest to which it binds. The lower the KD value, the stronger the binding strength between the amino acid sequence as disclosed herein and the target protein of interest to which it binds. Alternatively, the affinity can also be expressed in terms of the affinity constant (KA), which corresponds to 1/KD. The binding affinity of an amino acid sequence as disclosed herein can be determined in a manner known to the skilled person, depending on the specific target protein of interest. The 'avidity' of an amino acid sequence as disclosed herein is the measure of the strength of binding between the amino acid sequence as disclosed herein and the pertinent target protein of interest. Avidity is related to both the affinity between a binding site on the target protein of interest and a binding site on the amino acid sequence as disclosed herein and the number of pertinent binding sites present on the amino acid sequence as disclosed herein. Typically, the amino acid sequences as disclosed herein will bind to a target protein of interest with a dissociation constant (KD) of less than about 1 micromolar (1 μM), and preferably less than about 1 nanomolar (1 nM) [i.e., with an association constant (KA) of about 1,000,000 per molar ($10^6$ $M^{-1}$, 1E6/M) or more and preferably about 1,000,000,000 per molar ($10^9$ $M^{-1}$, 1E9/M) or more]. A KD value greater than about 1 millimolar is generally considered to indicate non-binding or non-specific binding. It is generally known in the art that the KD can also be expressed as the ratio of the dissociation rate constant of a complex, denoted as kOff (expressed in seconds$^{-1}$ or s$^{-1}$), to the rate constant of its association, denoted kOn (expressed in molar$^{-1}$ seconds$^{-1}$ or M$^{-1}$ s$^{-1}$). In particular, an amino acid sequence as disclosed herein will bind to the target protein of interest with a kOff ranging between 0.1 and 0.0001s$^{-1}$ and/or a kOn ranging between 1,000 and 1,000,000 M$^{-1}$ s$^{-1}$. Binding affinities, kOff and kOn rates may be determined by means of methods known to the person skilled in the art, for example ELISA methods, isothermal titration calorimetry, surface plasmon resonance, fluorescence-activated cell sorting analysis, and the more.

An amino acid sequence, in particular an antibody fragment, such as a $V_{HH}$, as disclosed herein is considered to be '(in) essentially isolated (form)' as used herein, when it has been extracted or purified from the host cell and/or medium in which it is produced.

In respect of the amino acid sequences, in particular antibody fragments, such as a $V_{HH}$'s or functional fragments thereof, as disclosed herein, the terms 'binding region', 'binding site' or 'interaction site' present on the amino acid sequences as disclosed herein shall herein have the meaning of a particular site, part, domain or stretch of amino acid residues present on the amino acid sequence as disclosed herein that is responsible for binding to a target molecule. Such binding region essentially consists of specific amino acid residues from the amino acid sequence as disclosed herein which are in contact with the target molecule.

The terms 'competing (with)', 'cross-blocking', 'cross-binding' and 'cross-inhibiting' as used interchangeably herein, generally refer to an amino acid sequence, in particular an antibody fragment, such as a $V_{HH}$, as disclosed herein that can interfere with the binding of other amino acid sequence as disclosed herein to a target protein of interest, as measured using a suitable in vitro, cellular or in vivo assay. Thus, more particularly, 'competing (with)', 'cross-blocking', 'cross-binding' and 'cross-inhibiting' using amino acid sequence as disclosed herein may mean interfering with or competing with the binding of another amino acid sequence as disclosed herein with a target protein of interest, thereby reducing that binding by at least 10% but preferably at least 20%, for example by at least 50%, at least 60%, at least 70%, at least 80%, at least 90%, at least 95% or more, as measured using a suitable in vitro, cellular or in vivo assay, compared to the binding of that other amino acid sequence as disclosed herein with the target protein of interest but without using the 'cross-blocking' amino acid sequence as disclosed herein.

An amino acid sequence, in particular an antibody fragment, such as a $V_{HH}$ or functional fragments thereof, as disclosed herein is said to show 'cross-reactivity' for two different target proteins of interest if it is specific for (as defined herein) both of these different target proteins of interest.

In cases where all of the two or more binding sites of amino acid sequence, in particular an antibody fragment, such as a $V_{HH}$ or functional fragments thereof, as disclosed herein are directed against or specifically bind to the same site, determinant, part, domain or stretch of amino acid residues of the target of interest, the amino acid sequence as disclosed herein is said to be 'bivalent' (in the case of two binding sites on the amino acid sequence) or multivalent (in the case of more than two binding sites on the amino acid sequence), such as for example trivalent.

As used herein, the term 'monovalent' when referring to an antibody fragment, such as a $V_{HH}$ or functional fragments thereof, denotes an antibody fragment in monomeric form. A monovalent antibody fragment contains only one binding site. In this context, the binding site of an antibody fragment, such as a $V_{HH}$ or functional fragments thereof, encompasses the one or more 'complementarity determining regions' or 'CDRs' of an antibody fragment that are directed against or specifically bind to a particular site, determinant, part, domain or stretch of amino acid residues of a target of interest.

As used herein, the term 'untagged' when referring to an antibody fragment, such as a $V_{HH}$ or functional fragments thereof, denotes an antibody fragment that contains no extraneous polypeptide sequences (e.g., contains only a $V_{HH}$ sequence, or a fragment thereof, labeled with a radioisotope as described herein). Exemplary extraneous polypeptide sequences include carboxy-terminal polypeptide tags, e.g., a His-tag, a cysteine-containing tag (e.g., a GGC-tag), and/or a Myc-tag.

The term 'bi-specific' when referring to an amino acid sequence, in particular an antibody fragment, such as a $V_{HH}$, as disclosed herein implies that either a) two or more of the binding sites of an amino acid sequence as disclosed herein are directed against or specifically bind to the same target of interest but not to the same (i.e. to a different) site, determinant, part, domain or stretch of amino acid residues of that target, the amino acid sequence as disclosed herein is said to be 'bi-specific' (in the case of two binding sites on the amino acid sequence) or multispecific (in the case of more than two binding sites on the amino acid sequence) or b) two or more binding sites of an amino acid sequence as disclosed herein are directed against or specifically bind to different target molecules of interest. The term 'multispecific' is used in the case that more than two binding sites are present on the amino acid sequence as disclosed herein.

Accordingly, a 'bispecific' amino acid sequence or antibody fragment, such as a bispecific' $V_{HH}$ or a 'multi-specific' amino acid sequence or antibody fragment, such as a 'multispecific' $V_{HH}$ as used herein, shall have the meaning of an amino acid sequence, in particular an antibody fragment, such as a $V_{HH}$, as disclosed herein comprising respectively two or at least two binding sites, wherein these two or more binding sites have a different binding specificity. Thus, an amino acid sequence, in particular an antibody fragment, such as a $V_{HH}$, as disclosed herein is considered 'bispecific' or 'multispecific' if respectively two or more than two different binding regions exist in the same, monomeric, amino acid sequence.

The 'half-life' of an amino acid sequence, in particular an antibody fragment, such as a $V_{HH}$ or functional fragments thereof, as disclosed herein can generally be defined as the time that is needed for the in vivo serum concentration of the amino acid sequence as disclosed herein to be reduced by 50%. The in vivo half-life of an amino acid sequence as disclosed herein can be determined in any manner known to the person skilled in the art, such as by pharmacokinetic analysis. As will be clear to the skilled person, the half-life can be expressed using parameters such as the t1/2-alpha, t1/2-beta and the area under the curve (AUC). An increased half-life in vivo is generally characterized by an increase in one or more and preferably in all three of the parameters t1/2-alpha, t1/2-beta and the area under the curve (AUC).

The term "lifetime extended" when referring to an antibody fragment, such as a $V_{HH}$ or functional fragments thereof as disclosed herein, is used to denote that the antibody fragment has been modified to extend the half-life of the antibody fragment. Strategies for extending the half-life of antibodies and antibody fragments are well-known in the art and include for example, but without limitation, linkage (chemically or otherwise) to one or more groups or moieties that extend the half-life, such as polyethylene glycol (PEG) or bovine serum albumin (BSA) or human serum albumin (HSA), antibody Fc fragments, or antigen-binding antibody fragments targeting serum proteins such as serum albumin.

As used herein, the terms 'inhibiting', 'reducing' and/or 'preventing' may refer to (the use of) an amino acid sequence, in particular an antibody fragment, such as a $V_{HH}$ or functional fragments thereof, as disclosed herein that specifically binds to a target antigen of interest and inhibits, reduces and/or prevents the interaction between that target antigen of interest, and its natural binding partner. The terms Inhibiting', 'reducing' and/or 'preventing' may also refer to (the use of) an amino acid sequence, in particular an antibody fragment, such as a $V_{HH}$ or functional fragments thereof, as disclosed herein that specifically binds to a target antigen of interest and inhibits, reduces and/or prevents a biological activity of that target antigen of interest, as measured using a suitable in vitro, cellular or in vivo assay. Accordingly, Inhibiting', 'reducing' and/or 'preventing' may also refer to (the use of) an amino acid sequence as disclosed herein that specifically binds to a target antigen of interest and inhibits, reduces and/or prevents one or more biological or physiological mechanisms, effects, responses, functions pathways or activities in which the target antigen of interest is involved. Such an action of the amino acid sequence as disclosed herein as an antagonist may be determined in any suitable manner and/or using any suitable (in vitro and usually cellular or in vivo) assay known in the art, depending on the target antigen of interest.

Thus, more particularly, 'inhibiting', 'reducing' and/or 'preventing' using amino acid sequence, in particular an antibody fragment, such as a $V_H$ or functional fragments thereof $_H$, as disclosed herein may mean either inhibiting, reducing and/or preventing the interaction between a target antigen of interest and its natural binding partner, or, inhibiting, reducing and/or preventing the activity of a target antigen of interest, or, inhibiting, reducing and/or preventing one or more biological or physiological mechanisms, effects, responses, functions pathways or activities in which the target antigen of interest is involved, such as by at least 10%, but preferably at least 20%, for example by at least 50%, at least 60%, at least 70%, at least 80%, at least 90%, at least 95% or more, as measured using a suitable in vitro, cellular or in vivo assay, compared to the activity of the target antigen of interest in the same assay under the same conditions but without using the amino acid sequence as disclosed herein. In addition, 'inhibiting', 'reducing' and/or 'preventing' may also mean inducing a decrease in affinity, avidity, specificity and/or selectivity of a target antigen of interest for one or more of its natural binding partners and/or inducing a decrease in the sensitivity of the target antigen of interest for one or more conditions in the medium or surroundings in which the target antigen of interest is present (such as pH, ion strength, the presence of co-factors, etc.), compared to the same conditions but without the presence of the amino acid sequence as disclosed herein. In the context of the present disclosure, 'inhibiting', 'reducing' and/or 'preventing' may also involve allosteric inhibition, reduction and/or prevention of the activity of a target antigen of interest.

As used herein, the terms 'enhancing', 'increasing' and/or 'activating' may refer to (the use of) an amino acid sequence, in particular an antibody fragment, such as a $V_{HH}$ or functional fragments thereof, as disclosed herein that specifically binds to a target protein of interest and enhances, increases and/or activates the interaction between that target protein of interest, and its natural binding partner. The terms 'enhancing', 'increasing' and/or 'activating' may also refer to (the use of) an amino acid sequence, in particular an antibody fragment, such as a $V_{HH}$ or functional fragments thereof, as disclosed herein that specifically binds to a target protein of interest and enhances, increases and/or activates a biological activity of that target protein of interest, as measured using a suitable in vitro, cellular or in vivo assay. Accordingly, 'enhancing', 'increasing' and/or 'activating' may also refer to (the use of) an amino acid sequence as disclosed herein that specifically binds to a target protein of interest and enhances, increases and/or activates one or more biological or physiological mechanisms, effects, responses, functions pathways or activities in which the target protein of interest is involved. Such an action of the amino acid sequence as disclosed herein as an agonist may be determined in any suitable manner and/or using any suitable (in vitro and usually cellular or in vivo) assay known in the art, depending on the target protein of interest.

The inhibiting or antagonizing activity or the enhancing or agonizing activity of an amino acid sequence, in particular an antibody fragment, such as a $V_{HH}$ or functional fragments thereof, as disclosed herein may be reversible or irreversible, but for pharmaceutical and pharmacological applications will typically occur reversibly.

An amino acid sequence, in particular an antibody fragment, such as a $V_{HH}$ or functional fragments thereof, as disclosed herein is considered to be '(in) essentially isolated (form)' as used herein, when it has been extracted or purified from the host cell and/or medium in which it is produced.

In respect of the amino acid sequences, in particular an antibody fragment, such as a $V_H$ or functional fragments thereof $_H$, as disclosed herein, the terms 'binding region', 'binding site' or 'interaction site' present on the amino acid sequences as disclosed herein shall herein have the meaning of a particular site, region, locus, part, or domain present on the target molecule, which particular site, region, locus, part, or domain is responsible for binding to that target molecule. Such binding region thus essentially consists of that particular site, region, locus, part, or domain of the target molecule, which is in contact with the amino acid sequence when bound to that target molecule.

As used herein, the term 'antibody' refers to polyclonal antibodies, monoclonal antibodies, humanized antibodies, single-chain antibodies, and fragments thereof such as Fab F(ab)2, Fv, and other fragments that retain the antigen binding function of the parent antibody. As such, an antibody may refer to an immunoglobulin or glycoprotein, or fragment or portion thereof, or to a construct comprising an antigen-binding portion comprised within a modified immunoglobulin-like framework, or to an antigen-binding portion comprised within a construct comprising a non-immunoglobulin-like framework or scaffold.

As used herein, the term 'monoclonal antibody' refers to an antibody composition having a homogeneous antibody population. The term is not limited regarding the species or source of the antibody, nor is it intended to be limited by the manner in which it is made. The term encompasses whole immunoglobulins as well as fragments and others that retain the antigen binding function of the antibody. Monoclonal antibodies of any mammalian species can be used in this disclosure. In practice, however, the antibodies will typically be of rat or murine origin because of the availability of rat or murine cell lines for use in making the required hybrid cell lines or hybridomas to produce monoclonal antibodies.

As used herein, the term 'polyclonal antibody' refers to an antibody composition having a heterogeneous antibody population. Polyclonal antibodies are often derived from the pooled serum from immunized animals or from selected humans.

'Heavy chain variable domain of an antibody or a functional fragment thereof', as used herein, means (i) the variable domain of the heavy chain of a heavy chain antibody, which is naturally devoid of light chains (also indicated hereafter as $V_{HH}$), including but not limited to the variable domain of the heavy chain of heavy chain antibodies of camelids or sharks or (ii) the variable domain of the heavy chain of a conventional four-chain antibody (also indicated hereafter as $V_H$), including but not limited to a camelized (as further defined herein) variable domain of the heavy chain of a conventional four-chain antibody (also indicated hereafter as camelized $V_H$) or any functional fragments thereof, such as but not limited to one or more stretches of amino acid residues (i.e. small peptides) that are particularly suited for binding to a tumor antigen or an antigen present on cancer cells and which are present in, and/or may be incorporated into, the $V_{HH}$'s as disclosed herein (or may be based on and/or derived from CDR sequences of the $V_{HH}$'s as disclosed herein).

As further described hereinbelow, the amino acid sequence and structure of a heavy chain variable domain of an antibody can be considered, without however being limited thereto, to be comprised of four framework regions or 'FR's', which are referred to in the art and hereinbelow as 'framework region 1' or 'FR1'; as 'framework region 2' or 'FR2'; as 'framework region 3' or 'FR3'; and as 'framework region 4' or 'FR4', respectively, which framework regions are interrupted by three complementary determining regions or 'CDR's', which are referred to in the art as 'complementarity determining region 1' or 'CDR1'; as 'complementarity determining region 2' or 'CDR2'; and as 'complementarity determining region 3' or 'CDR3', respectively.

As used herein, the terms 'complementarity determining region' or 'CDR' within the context of antibodies refer to variable regions of either the H (heavy) or the L (light) chains (also abbreviated as VH and VL, respectively) and contain the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains. As also further described hereinbelow, the total number of amino acid residues in a heavy chain variable domain of an antibody (including a $V_{HH}$ or a $V_H$) can be in the region of 110-130, is preferably 112-115, and is most preferably 113. It should however be noted that parts, fragments or analogs of a heavy chain variable domain of an antibody are not particularly limited as to their length and/or size, as long as such parts, fragments or analogs retain (at least part of) the functional activity, and/or retain (at least part of) the binding specificity of the original a heavy chain variable domain of an antibody from which these parts, fragments or analogs are derived from.

Parts, fragments or analogs retaining (at least part of) the functional activity, and/or retaining (at least part of) the binding specificity of the original heavy chain variable domain of an antibody from which these parts, fragments or analogs are derived from are also further referred to herein as 'functional fragments' of a heavy chain variable domain.

Figure 2:
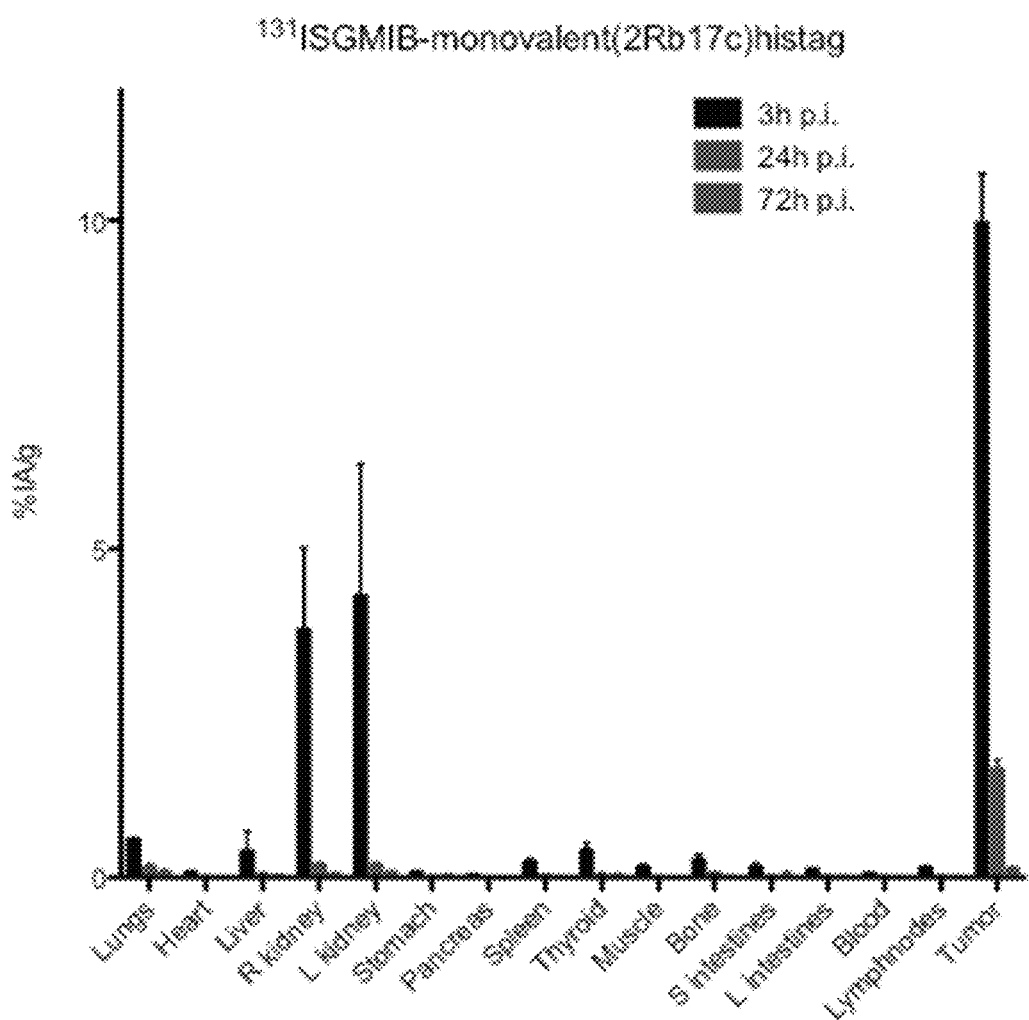
FIG. 2: After injection of the His-tagged [$^{131}$I]SGMIB-labeled mono-valent anti-HER2 $V_{HH}$ 2 Rb17c, different tissues of interest are counted for $^{131}$I activity in an automated gamma counter. Uptake values were expressed as % injected Activity/gram tissue (% IA/g). The obtained data were used to calculate tumor to healthy tissue ratios. Radiation dose estimates for the adult human female were calculated from the biodistribution data of mice using OLINDA 1.0 software, using a voiding bladder interval of 1 h. The calculations were based on time-activity curves to determine the number of disintegrations in organs. Organ doses and effective dose were calculated using the appropriate weighting factors for the various organs.

The amino acid residues of a variable domain of a heavy chain variable domain of an antibody (including a $V_{HH}$ or a $V_H$) are numbered according to the general numbering for heavy chain variable domains given by Kabat et al. ('Sequence of proteins of immunological interest', US Public Health Services, NIH Bethesda, Md., Publication No. 91), as applied to $V_{HH}$ domains from Camelids in the article of Riechmann and Muyldermans, referred to above (see for example FIG. 2 of said reference). According to this numbering, FR1 of a heavy chain variable domain comprises the amino acid residues at positions 1-30, CDR1 of a heavy chain variable domain comprises the amino acid residues at positions 31-35, FR2 of a heavy chain variable domain comprises the amino acids at positions 36-49, CDR2 of a heavy chain variable domain comprises the amino acid residues at positions 50-65, FR3 of a heavy chain variable domain comprises the amino acid residues at positions 66-94, CDR3 of a heavy chain variable domain comprises the amino acid residues at positions 95-102, and FR4 of a heavy chain variable domain comprises the amino acid residues at positions 103-113. [In this respect, it should be noted that—as is well known in the art for $V_{HH}$ domains— the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.

Alternative methods for numbering the amino acid residues of heavy chain variable domains are the method described by Chothia et al. (Nature 342, 877-883 (1989)), the so-called 'AbM definition' and the so-called 'contact definition'. However, in the present description, claims and figures, the numbering according to Kabat as applied to $V_{HH}$ domains by Riechmann and Muyldermans will be followed, unless indicated otherwise.

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N. V. and Ablynx N V; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by Ablynx N V and the further published patent applications by Ablynx N V; Hamers-Casterman et al., Nature 1993 Jun. 3; 363 (6428): 446-8; Davies and Riechmann, FEBS Lett. 1994 Feb. 21; 339(3): 285-90; Muyldermans et al., Protein Eng. 1994 September; 7(9): 1129-3; Davies and Riechmann, Biotechnology (NY) 1995 May; 13(5): 475-9; Gharoudi et al., 9th Forum of Applied Biotechnology, Med. Fac. Landbouw Univ. Gent. 1995; 60/4a part I: 2097-2100; Davies and Riechmann, Protein Eng. 1996 June; 9(6): 531-7; Desmyter et al., Nat Struct Biol. 1996 September; 3(9): 803-11; Sheriff et al., Nat Struct Biol. 1996 September; 3(9): 733-6; Spinelli et al., Nat Struct Biol. 1996 September; 3(9): 752-7; Arbabi Ghahroudi et al., FEBS Lett. 1997 Sep. 15; 414(3): 521-6; Vu et al., Mol. Immunol. 1997 November-December; 34(16-17): 1121-31; Atarhouch et al., Journal of Camel Practice and Research 1997; 4: 177-182; Nguyen et al., J. Mol. Biol. 1998 Jan. 23; 275(3): 413-8; Lauwereys et al., EMBO J. 1998 Jul. 1; 17(13): 3512-20; Frenken et al., Res Immunol. 1998 July-August; 149(6):589-99; Transue et al., Proteins 1998 Sep. 1; 32(4): 515-22; Muyldermans and Lauwereys, J. Mol. Recognit. 1999 March-April; 12 (2): 131-40; van der Linden et al., Biochim. Biophys. Acta 1999 Apr. 12; 1431(1): 37-46; Decanniere et al., Structure Fold. Des. 1999 Apr. 15; 7(4): 361-70; Ngyuen et al., Mol. Immunol. 1999 June; 36(8): 515-24; Woolven et al., Immunogenetics 1999 October; 50 (1-2): 98-101; Riechmann and Muyldermans, J. Immunol. Methods 1999 Dec. 10; 231 (1-2): 25-38; Spinelli et al., Biochemistry 2000 Feb. 15; 39(6): 1217-22; Frenken et al., J. Biotechnol. 2000 Feb. 28; 78(1): 11-21; Nguyen et al., EMBO J. 2000 Mar. 1; 19(5): 921-30; van der Linden et al., J. Immunol. Methods 2000 Jun. 23; 240 (1-2): 185-95; Decanniere et al., J. Mol. Biol. 2000 Jun. 30; 300 (1): 83-91; van der Linden et al., J. Biotechnol. 2000 Jul. 14; 80(3): 261-70; Harmsen et al., Mol. Immunol. 2000 August; 37(10): 579-90; Perez et al., Biochemistry 2001 Jan. 9; 40(1): 74-83; Conrath et al., J. Biol. Chem. 2001 Mar. 9; 276 (10): 7346-50; Muyldermans et al., Trends Biochem Sci. 2001 April; 26(4):230-5; Muyldermans S., J. Biotechnol. 2001 June; 74 (4): 277-302; Desmyter et al., J. Biol. Chem. 2001 Jul. 13; 276 (28): 26285-90; Spinelli et al., J. Mol. Biol. 2001 Aug. 3; 311 (1): 123-9; Conrath et al., Antimicrob Agents Chemother. 2001 October; 45 (10): 2807-12; Decanniere et al., J. Mol. Biol. 2001 Oct. 26; 313(3): 473-8; Nguyen et al., Adv Immunol. 2001; 79: 261-96; Muruganandam et al., FASEB J. 2002 February; 16 (2): 240-2; Ewert et al., Biochemistry 2002 Mar. 19; 41 (11): 3628-36; Dumoulin et al., Protein Sci. 2002 March; 11 (3): 500-15; Cortez-Retamozo et al., Int. J. Cancer. 2002 Mar. 20; 98 (3): 456-62; Su et al., Mol. Biol. Evol. 2002 March; 19 (3): 205-15; van der Vaart J M., Methods Mol. Biol. 2002; 178: 359-66; Vranken et al., Biochemistry 2002 Jul. 9; 41 (27): 8570-9; Nguyen et al., Immunogenetics 2002 April; 54 (1): 39-47; Renisio et al., Proteins 2002 Jun. 1; 47 (4): 546-55; Desmyter et al., J. Biol. Chem. 2002 Jun. 28; 277 (26): 23645-50; Ledeboer et al., J. Dairy Sci. 2002 June; 85 (6): 1376-82; De Genst et al., J. Biol. Chem. 2002 Aug. 16; 277 (33): 29897-907; Ferrat et al., Biochem. J. 2002 Sep. 1; 366 (Pt 2): 415-22; Thomassen et al., Enzyme and Microbial Technol. 2002; 30: 273-8; Harmsen et al., Appl. Microbiol. Biotechnol. 2002 December; 60 (4): 449-54; Jobling et al., Nat. Biotechnol. 2003 January; 21 (1): 77-80; Conrath et al., Dev. Comp. Immunol. 2003 February; 27 (2): 87-103; Pleschberger et al., Bioconjug. Chem. 2003 March-April; 14 (2): 440-8; Lah et al., J. Biol. Chem. 2003 Apr. 18; 278 (16): 14101-11; Nguyen et al., Immunology. 2003 May; 109 (1): 93-101; Joosten et al., Microb. Cell Fact. 2003 Jan. 30; 2 (1): 1; Li et al., Proteins 2003 Jul. 1; 52 (1): 47-50; Loris et al., Biol. Chem. 2003 Jul. 25; 278 (30): 28252-7; van Koningsbruggen et al., J. Immunol. Methods. 2003 August; 279 (1-2): 149-61; Dumoulin et al., Nature. 2003 Aug. 14; 424 (6950): 783-8; Bond et al., J. Mol. Biol. 2003 Sep. 19; 332 (3): 643-55; Yau et al., J. Immunol. Methods. 2003 Oct. 1; 281 (1-2): 161-75; Dekker et al., J. Virol. 2003 November; 77 (22): 12132-9; Meddeb-Mouelhi et al., Toxicon. 2003 December; 42 (7): 785-91; Verheesen et al., Biochim. Biophys. Acta 2003 Dec. 5; 1624 (1-3): 21-8; Zhang et al., J Mol Biol. 2004 Jan. 2; 335 (1): 49-56; Stijlemans et al., J Biol. Chem. 2004 Jan. 9; 279 (2): 1256-61; Cortez-Retamozo et al., Cancer Res. 2004 Apr. 15; 64 (8): 2853-7; Spinelli et al., FEBS Lett. 2004 Apr. 23; 564 (1-2): 35-40; Pleschberger et al., Bioconjug. Chem. 2004 May-June; 15 (3): 664-71; Nicaise et al., Protein Sci. 2004 July; 13 (7): 1882-91; Omidfar et al., Tumour Biol. 2004 July-August; 25 (4): 179-87; Omidfar et al., Tumour Biol. 2004 September-December; 25(5-6): 296-305; Szynol et al., Antimicrob Agents Chemother. 2004 September; 48(9):3390-5; Saerens et al., J. Biol. Chem. 2004 Dec. 10; 279 (50): 51965-72; De Genst et al., J. Biol. Chem. 2004 Dec. 17; 279 (51): 53593-601; Dolk et al., Appl. Environ. Microbiol. 2005 January; 71(1): 442-50; Joosten et al., Appl Microbiol Biotechnol. 2005 January; 66(4): 384-92; Dumoulin et al., J. Mol. Biol. 2005 Feb. 25; 346 (3): 773-88; Yau et al., J Immunol Methods. 2005 February; 297 (1-2): 213-24; De Genst et al., J. Biol. Chem. 2005 Apr. 8; 280 (14): 14114-21; Huang et al., Eur. J. Hum. Genet. 2005 Apr. 13; Dolk et al., Proteins. 2005 May 15; 59 (3): 555-64; Bond et al., J. Mol. Biol. 2005 May 6; 348(3):699-709; Zarebski et al., J. Mol. Biol. 2005 Apr. 21.

Generally, it should be noted that the term 'heavy chain variable domain' as used herein in its broadest sense is not limited to a specific biological source or to a specific method of preparation. For example, as will be discussed in more detail below, the heavy chain variable domains derived from heavy chain antibodies (i.e. $V_{HH}$'s) as disclosed herein can be obtained (1) by isolating the $V_{HH}$ domain of a naturally occurring heavy chain antibody; (2) by expression of a nucleotide sequence encoding a naturally occurring $V_{HH}$ domain; (3) by 'camelization' (as described below) of a naturally occurring $V_H$ domain from any animal species, in particular a species of mammal, such as from a human being, or by expression of a nucleic acid encoding such a camelized $V_H$ domain; (4) by 'camelisation' of a 'domain antibody' or Dab' as described by Ward et al (supra), or by expression of a nucleic acid encoding such a camelized $V_H$ domain (5) using synthetic or semi-synthetic techniques for preparing proteins, polypeptides or other amino acid sequences; (6) by preparing a nucleic acid encoding a $V_{HH}$ using techniques for nucleic acid synthesis, followed by expression of the nucleic acid thus obtained; and/or (7) by any combination of the foregoing. Suitable methods and techniques for performing the foregoing will be clear to the skilled person based on the disclosure herein and for example include the methods and techniques described in more detail hereinbelow.

The term 'effective amount', as used herein, means the amount needed to achieve the desired result or results.

As used herein, the terms 'determining', 'measuring', 'assessing', 'monitoring' and 'assaying' are used interchangeably and include both quantitative and qualitative determinations.

As used herein, the term 'prevention and/or treatment' comprises preventing and/or treating a certain disease and/or disorder, preventing the onset of a certain disease and/or disorder, slowing down or reversing the progress of a certain disease and/or disorder, preventing or slowing down the onset of one or more symptoms associated with a certain disease and/or disorder, reducing and/or alleviating one or more symptoms associated with a certain disease and/or disorder, reducing the severity and/or the duration of a certain disease and/or disorder, and generally any prophylactic or therapeutic effect of the amino acid sequences as disclosed herein that is beneficial to the subject or patient being treated.

As used herein, the terms 'diagnosis', 'prediction' and/or 'prognosis' as used herein comprise diagnosing, predicting and/or prognosing a certain disease and/or disorder, thereby predicting the onset and/or presence of a certain disease and/or disorder, and/or predicting the progress and/or duration of a certain disease and/or disorder, and/or predicting the response of a patient suffering from of a certain disease and/or disorder to therapy.

[Invention-Related Definitions]

As used herein, the terms 'solid tumor-specific antigen', 'tumor-specific antigen', 'tumor antigen', 'target protein present on and/or specific for a (solid) tumor', 'tumor-specific target (protein)", "tumor-associated antigen" are used interchangeably herein and include any protein which is present only on tumor cells and not on any other cell or any protein, which is present on some tumor cells and also on some normal, healthy cells. Non-limiting examples of tumor antigens include tissue differentiation antigens, mutant protein antigens, oncogenic viral antigens, cancer-testis antigens and vascular or stromal specific antigens.

As used herein, the term 'tumor cell' refers to a cell that is present in a primary or metastatic tumor lesion. In this context, tumors consist not only of cancer cells, but should be considered as organ-like structures in which a complex bidirectional interplay exists between transformed and non-transformed cells. The malignant potential of transformed cells requires an apt support structure from the stroma, which can consist of fibroblasts, adipocytes, blood and lymph vessels, but may also be considerably infiltrated by a wide range of immune cells.

As used herein, the terms 'cancer cell-specific antigen', 'cancer-specific antigen', 'cancer antigen', 'target protein present on and/or specific for a cancer cell', 'cancer cell-specific target (protein)", "cancer (cell)-associated antigen" are used interchangeably herein and include any protein which is present only on cancer cells and not on any other cell or any protein, which is present on some cancer cells and also on some normal, healthy cells. Non-limiting examples of cancer-cell-specific antigens include tissue differentiation antigens, mutant protein antigens, oncogenic viral antigens, cancer-testis antigens and vascular or stromal specific antigens.

As used herein, the term 'radiolabelled' as in 'radiolabelled' amino acid sequence, 'radiolabelled' antibody fragment or 'radiolabelled' $V_{HH}$ refers to the radioisotopic labeling of that amino acid sequence, antibody fragment or $V_{HH}$, wherein the amino acid sequence, antibody fragment or $V_{HH}$ is labelled by including, coupling, or chemically linking a radionuclide to its amino acid sequence structure.

As used herein, the terms 'radionuclide', 'radioactive nuclide', 'radioisotope' or 'radioactive isotope', are used interchangeably herein and refer to atoms with an unstable nucleus, characterized by excess energy available to be imparted either to a newly created radiation particle within the nucleus or via internal conversion. During this process, the radionuclide is said to undergo radioactive decay, resulting in the emission of gamma ray(s) and/or subatomic particles such as alpha or beta particles. These emissions constitute ionizing radiation. Radionuclides occur naturally, or can be produced artificially.

By "solid tumor(s)" or "tumor(s)" are meant primary tumors and/or metastases (wherever located) such as but not limited to gliomas, pancreatic tumors; lung cancer, e.g. small cell lung cancer, breast cancer; epidermoid carcinomas; neuroendocrine tumors; gynaecological and urological cancer, e.g. cervical, uterine, ovarian, prostate, renal-cell carcinomas, testicular germ cell tumors or cancer; pancreas cancer (pancreatic adenocarcinoma); glioblastomas; head and/or neck cancer; CNS (central nervous system) cancer; bones tumors; solid pediatric tumors; haematological malignancies; AIDS-related cancer; soft-tissue sarcomas, and skin cancer, including melanoma and Kaposi's sarcoma.

As used herein, the term 'cancer cell' refers to a cell that divides and reproduces abnormally and limitlessly with uncontrolled growth and which can break away and travel to other parts of the body and set up another site, referred to as metastasis.

A 'lesion' as used herein can refer to any abnormal change in a body tissue or organ resulting from injury or disease. In cancer terminology, lesion typically refers to a tumor.

As used herein, the term 'HER-2 positive' as in 'HER-2 positive (cancer) lesions', 'HER-2 positive (breast) cancer', or 'HER-2 positive tumor' refers to cancerous or malignant cells or tissue characterized by HER2 gene amplification or HER2 protein overexpression and thus have abnormally high levels of the HER2 gene and/or the HER2 protein compared to normal healthy cells. HER-2 positive breast cancer is characterized by cancerous breast cells characterized by HER2 gene amplification or HER2 protein overexpression. In about 1 of every 5 breast cancers, the cancer cells make an excess of HER2, mainly caused HER2 gene amplification due to one or more gene mutations. The elevated levels of HER2 protein that it causes can occur in many types of cancer—and are thus not limited to breast cancer.

As used herein, the term 'HER-2 negative' as in 'HER-2 negative (cancer) lesions', 'HER-2 negative (breast) cancer', 'HER-2 negative tumor', 'HER-2 negative cell(s)' can refer either to cancerous or malignant cells or tissue or to normal healthy cells or tissue, both of which are characterized by the absence of HER2 gene amplification or HER2 protein overexpression and thus by normal levels of the HER2 gene and/or the HER2 protein.

The term 'in situ hybridization (ISH)' as used herein refers to a type of hybridization assay that uses a labeled complementary DNA or RNA strand (i.e., probe) to localize a specific DNA or RNA sequence in a portion or section of tissue (in situ), or, if the tissue is small enough (e.g. plant seeds, *Drosophila* embryos), in the entire tissue (whole mount ISH), in cells and in circulating tumor cells (CTCs). In situ hybridization is a powerful technique for identifying specific mRNA species within individual cells in tissue sections, providing insights into physiological processes and disease pathogenesis. In particular, in situ hybridization is used to reveal the location of specific nucleic acids sequences on chromosomes or in tissues, a crucial step for understanding the organization, regulation and function of genes. The key techniques currently in use include: in situ hybridization to mRNA with oligonucleotide and RNA probes (both radio labelled and hapten labelled); analysis with light and electron microscopes; whole mount in situ hybridization; double detection of RNAs and RNA plus protein; and fluorescent in situ hybridization to detect chromosomal sequences. DNA ISH can be used to determine the structure of chromosomes. Fluorescent DNA ISH (FISH) can, for example, be used in medical diagnostics to assess chromosomal integrity. RNA ISH (RNA in situ hybridization) is used to measure and localize RNAs (mRNAs, lncRNAs and miRNAs) within tissue sections, cells, whole mounts, and circulating tumor cells (CTCs).

The term 'fluorescence in situ hybridization (FISH)' as used herein refers to a specific type of in situ hybridization assay that is used to detect and localize the presence or absence of specific DNA sequences on chromosomes. FISH uses fluorescent probes that bind to only those parts of the chromosome with which they show a high degree of sequence complementarity. Fluorescence microscopy can be used to find out where the fluorescent probe is bound to the chromosomes. FISH is often used for finding specific features in DNA for use in genetic counseling, medicine, and species identification. FISH can also be used to detect and localize specific RNA targets (mRNA, lncRNA and miRNA) in cells, circulating tumor cells, and tissue samples. In this context, it can help define the spatial-temporal patterns of gene expression within cells and tissues.

The term Immunohistochemistry (IHC)' as used herein refers to the process of detecting antigens (e.g., proteins) in cells of a tissue section by exploiting the principle of antibodies binding specifically to antigens in sections of biological tissues. Immunohistochemical staining is widely used in the diagnosis of abnormal cells such as those found in cancerous tumors. IHC is also widely used in basic research to understand the distribution and localization of biomarkers and differentially expressed proteins in different parts of a biological tissue.

Trastuzumab' (Trade names: Herclon®, Herceptin®) is a monoclonal antibody that interferes with the HER2/neu receptor. Its main use is to treat certain breast cancers.

'Pertuzumab' or '2C4' (Trade name: Perjeta®) is a monoclonal antibody that binds to HER2, more particularly domain II of HER2, thereby inhibiting the dimerization of HER2 with other HER receptors. Its main use is to treat HER2-positive breast cancers.

The term 'primary tumor(s)' as used herein is a tumor growing at the anatomical site where tumor progression began and proceeded to yield a cancerous mass.

The term 'metastatic lesion(s)' as used herein refers to malignant, or cancerous, tumors that have spread from their original location to other parts of the body. Related medical terms that might be used interchangeably include late-stage cancer, advanced cancer, or metastatic disease. In general, metastatic lesions are considered to be incurable, although treatment is often available to control the spread of cancerous cells and potentially increase the individual's life expectancy.

Metastasis is the term for the spread of cancer beyond its originating site in the body. Thus, metastatic lesions are cancerous tumors that are found in locations apart from the original starting point of the primary tumor. Metastatic tumors occur when cells from the primary tumor break off and travel to distant parts of the body via the lymph system and blood stream. Alternately, cells from the original tumor could seed into new tumors at adjacent organs or tissues: Metastatic disease' as used herein refers to late-stage cancer and to the medical classification of cancer as being in stage III, when cancer cells are found in lymph nodes near the original tumor, or in stage IV, when cancer cells have traveled far beyond the primary tumor site to distant parts of the body. Metastatic lesions are most commonly found in the brain, lungs, liver, or bones. An individual with metastatic cancer might or might not experience any symptoms, and the symptoms could be related to the area where metastasized cells have relocated. Once metastatic lesions are present in the body, the individual's cancer will be considered incurable for most cancer types. This means it is excessively difficult to eradicate every existing cancer cell with available treatments. In this case, the goal of treatment becomes slowing the growth of tumors to maintain the highest possible quality of life and potentially extend the individual's life expectancy. In some cases, people with metastatic lesions can live for a number of years with appropriate treatment for symptom management.

The '(calculated mean) effective dose' of radiation within a subject as used herein refers to the tissue-weighted sum of the equivalent doses in all specified tissues and organs of the body and represents the stochastic health risk, which the probability of cancer induction and genetic effects of ionizing radiation delivered to those body parts. It takes into account the type of radiation and the nature of each organ or tissue being irradiated. It is the central quantity for dose limitation in radiological protection in the international system of radiological protection devised by the International Commission on Radiological Protection (ICRP). The SI unit for effective dose is the sievert (Sv) which is one joule/kilogram (J/kg). The effective dose replaced the former "effective dose equivalent" in 1991 in the ICRP system of dose quantities. For procedures using radiopharmaceuticals, the effective dose is typically expressed per unit of injected activity, i.e. expressed in mSv/MBq. The effective dose for the individual patient will then depend upon the injected activity of the radiopharmaceutical, expressed in MBq, and the calculated mean effective dose, expressed in mSv/MBq.

The effective dose for radiopharmaceuticals is calculated using OLINDA/EXM® software, that was approved in 2004 by the FDA. The OLINDA/EXM® personal computer code performs dose calculations and kinetic modeling for radiopharmaceuticals (OLINDA/EXM stands for Organ Level INternal Dose Assessment/EXponential Modeling). OLINDA® calculates radiation doses to different organs of the body from systemically administered radiopharmaceuticals and performs regression analysis on user-supplied biokinetic data to support such calculations for nuclear medicine drugs. These calculations are used to perform risk/benefit evaluations of the use of such pharmaceuticals in diagnostic and therapeutic applications in nuclear medicine. The technology employs a number of standard body models for adults, children, pregnant women and others, that are widely accepted and used in the internal dose community. The calculations are useful to pharmaceutical industry developers, nuclear medicine professionals, educators, regulators, researchers and others who study the accepted radiation doses that should be delivered when radioactive drugs are given to patients or research subjects.

The calculated effective dose depends on the chosen standard body model and the chosen voiding bladder model. The values provided herein have been calculated using the female adult model and a voiding bladder interval of 1 h.

All documents cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

[Body of Description]

The present inventors have identified solid tumor-binding antibody fragments and cancer cell-binding antibody fragments, more particularly $V_{HH}$'s or functional fragments thereof, specifically interacting with an antigen that is specific for solid tumors and/or for cancer cells for use in the prevention and/or treatment of cancer. Additionally and more importantly, by radiolabelling the $V_{HH}$'s as disclosed herein, an improved and effective method for radioimmunotherapy has been developed, resulting in high tumor or cancer cell uptake values, low healthy tissue uptake values, low overall biodistribution and fast clearance from the blood in a subject in need thereof, and in particular in human patients in need thereof.

Thus, the radio-labelled $V_{HH}$'s or functional fragments thereof as disclosed herein not only show a high therapeutic efficacy but also, through their low uptake by normal healthy tissues and their fast clearance, a low toxicity effect and therefore much less side effects in treated patients compared to traditional immunotherapy or known radio-immunotherapy agents.

The efficacy and potency of the antibody fragments as disclosed herein thus suggest a potential for a higher maximally tolerated dosage (MTD) in medical applications, allowing repeated and continued administration of a high treatment dosage, so as to effectively counteract tumor or cancer cell growth while still remaining below the dose-limiting toxicity (DLT) side-effects on normal healthy tissue.

Therefore, the present disclosure demonstrates for the first time that radio-labelled antibody fragments, and in particular radiolabelled $V_{HH}$'s or functional fragments thereof, can be used to effectively protect or treat an animal or human from cancer. More particularly, the present disclosure shows the therapeutic efficacy of radiolabeled, monovalent, and non-lifetime extended $V_{HH}$'s or functional fragments thereof.

The radiolabelled antibody fragments disclosed herein can be derived from a naturally occurring polypeptide, or alternatively they can be entirely artificially designed. Non-limiting examples of such naturally occurring polypeptides include heavy chain antibodies (hcAb), such as but not limited to camelid heavy chain antibodies.

In particular, the heavy chain variable domains derived from heavy chain antibodies (i.e. the $V_{HH}$'s) as disclosed herein consist of a single polypeptide chain and are not post-translationally modified. More particularly, the $V_{HH}$'s or functional fragments thereof disclosed herein are derived from an innate or adaptive immune system, preferably from a protein of an innate or adaptive immune system. Still more particularly, the $V_{HH}$'s disclosed herein comprise 4 framework regions and 3 complementary determining regions, or any suitable fragment thereof (which will then usually contain at least some of the amino acid residues that form at least one of the complementary determining regions). In particular, the $V_{HH}$'s disclosed herein are easy to produce at high yield, preferably in a microbial recombinant expression system, and convenient to isolate and/or purify subsequently.

According to particular embodiments, the disclosure provides a number of stretches of amino acid residues (i.e. small peptides) that are particularly suited for binding to a tumor antigen or a cancer cell antigen, such as but not limited to HER2.

These stretches of amino acid residues may be present in, and/or may be incorporated into, the $V_{HH}$'s as disclosed herein, in particular in such a way that they form (part of) the antigen binding site of that $V_{HH}$. As these stretches of amino acid residues were first generated as CDR sequences of antibodies (or may be based on and/or derived from such CDR sequences, as further described herein), they will also generally be referred to herein as 'CDR sequences' (i.e. as CDR1 sequences, CDR2 sequences and CDR3 sequences, respectively). It should however be noted that the disclosure in its broadest sense is not limited to a specific structural role or function that these stretches of amino acid residues may have in the heavy chain variable domains as disclosed herein, as long as these stretches of amino acid residues allow the variable domains as disclosed herein to specifically bind to a tumor antigen and/or a cancer cell-specific antigen. Thus, generally, the disclosure in its broadest sense relates to radiolabelled $V_{HH}$'s for use in the treatment and/or prevention of cancer, which $V_{HH}$'s comprise a combination of CDR sequences as described herein and are specifically directed to a tumor-specific or a cancer cell-specific target protein.

Thus, in particular, but non-limiting embodiments, the VHH's as disclosed herein comprise at least one amino acid sequence that is chosen from the group consisting of the CDR1 sequences, CDR2 sequences and CDR3 sequences that are described herein. In particular, the $V_{HH}$'s as disclosed herein may comprise at least one antigen binding site, wherein said antigen binding site comprises at least one combination of a CDR1 sequence, a CDR2 sequence and a CDR3 sequence that are described herein.

Any $V_{HH}$ antibody fragment as disclosed herein and having one these CDR sequence combinations is preferably such that it can specifically bind (as defined herein) to a tumor-specific antigen and/or to a cancer-cell-specific antigen, and more in particular such that it specifically binds to a tumor-specific antigen and/or to a cancer-cell-specific antigen with dissociation constant (Kd) of $10^{-8}$ moles/liter or less of said variable domain in solution.

In particular embodiments, the $V_{HH}$ antibody fragments against HER2 as disclosed herein are such that they can specifically bind to HER2 with dissociation constant (Kd) of less than 5 nM, such as between 1 to 5 nM, preferably between 2 and 3 nM.

Specific binding of a $V_{HH}$ tumor antigen or cancer cell antigen can be determined in any suitable manner known per se, including, for example biopanning, Scatchard analysis and/or competitive binding assays, such as radioimmunoassays (RIA), enzyme immunoassays (EIA) and sandwich competition assays, and the different variants thereof known in the art.

In further particular embodiments, the $V_{HH}$'s as disclosed herein comprise at least one combination of CDR sequences chosen from the group comprising:

a CDR1 region having SEQ ID NO: 1, a CDR2 region having has SEQ ID NO: 2, and a CDR3 region having SEQ ID NO: 3, and/or a CDR1 region having SEQ ID NO: 4, a CDR2 region having has SEQ ID NO: 5, and a CDR3 region having SEQ ID NO: 6.

Thus, in particular embodiments, the present disclosure provides heavy chain variable domains derived from heavy chain antibodies with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and are as further defined herein.

SEQ ID NO's: 7 and 8 (see Table 1) give the amino acid sequences of heavy chain variable domains that have been raised against a tumor-specific antigen, in particular against HER2.

TABLE 1

VHH sequences

| Name | SEQ ID | VHH Amino acid sequence |
|---|---|---|
| 2Rs15d | 7 | QVQLQESGGGSVQAGGSLKLTCAASGYIFNSCGMGWYRQ SPGRERELVSRISGDGDTWHKESVKGRFTISQDNVKKTL YLQMNSLKPEDTAVYFCAVCYNLETYWGQGTQVTVSS |
| 2Rb17c | 8 | QVQLQESGGGLVQPGGSLRLSCAASGFIFSNDAMTWVRQ APGKGLEWVSSINWSGTHTNYADSVKGRFTISRDNAKRT LYLQMNSLKDEDTALYYCVTGYGVTKTPTGQGTQVTVSS |

In particular, the disclosure in some specific embodiments provides radiolabelled $V_{HH}$ domains directed against a tumor-specific or cancer cell-specific target antigen, which have at least 80%, preferably at least 85%, such as 90% or 95% or more sequence identity with at least one of the heavy chain variable domains of SEQ ID NO's: 7 or 8 (see Table 1), or functional fragments thereof, and nucleic acid sequences that encode such heavy chain variable domains or functional fragments thereof.

Some particularly preferred heavy chain variable domain sequences as disclosed herein are those which can bind to and/or are directed against HER2 and which have at least 90% amino acid identity with at least one of the heavy chain variable domains of SEQ ID NO's: 7 or 8 (see Table 1), in which for the purposes of determining the degree of amino acid identity, the amino acid residues that form the CDR sequences are disregarded.

In these heavy chain variable domains, the CDR sequences (see Table 2) are generally as further defined herein.

TABLE 2

Specific combinations of CDR sequences
(CDR sequences identified using IMGT numbering)

| Name | CDR1 sequence | SEQ ID | CDR2 sequence | SEQ ID | CDR3 sequence | SEQ ID |
|---|---|---|---|---|---|---|
| 2Rs15d | GYIFNSCG | 1 | ISGDGDT | 2 | AVCYNLETY | 3 |
| 2Rb17c | GFIFSNDA | 4 | INWSGTHT | 5 | VTGYGVTKTP | 6 |

It should be noted that the disclosure is not limited as to the origin of the $V_{HH}$ fragments disclosed herein (or of the nucleotide sequences to express these), nor as to the way that the $V_{HH}$ fragments or nucleotide sequences disclosed herein are (or have been) generated or obtained. Thus, the $V_{HH}$ fragments disclosed herein may be naturally occurring amino acid sequences (from any suitable species) or synthetic or semi-synthetic amino acid sequences. In a specific but non-limiting aspect of the disclosure, the amino acid sequence is a naturally occurring immunoglobulin sequence (from any suitable species) or a synthetic or semi-synthetic immunoglobulin sequence, including but not limited to "humanized" immunoglobulin sequences (such as partially or fully humanized mouse or rabbit immunoglobulin sequences, and in particular partially or fully humanized $V_{HH}$ sequences), "camelized" immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Also, a $V_{HH}$ sequence or functional fragments thereof as disclosed herein may be suitably humanized, as further described herein, so as to provide one or more further (partially or fully) humanized amino acid sequences of the disclosure. Similarly, when an amino acid sequence comprises a synthetic or semi-synthetic sequence (such as a partially humanized sequence), said sequence may optionally be further suitably humanized, again as described herein, so as to provide one or more further (partially or fully) humanized amino acid sequences as disclosed herein.

In particular, humanized amino acid sequences may be amino acid sequences in which at least one amino acid residue is present (and in particular, in at least one of the framework residues) that is and/or that corresponds to a humanizing substitution. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences or functional fragments thereof can be tested for affinity for the target, for stability, for ease and level of expression, and/or for other desired properties. In this way, by means of a limited degree of trial and error, other suitable humanizing substitutions (or suitable combinations thereof) can be determined by the skilled.

In order to be suitable for the medical purposes as disclosed herein, and in particular for the therapeutic and prophylactic applications in cancer as disclosed herein, in which it is intended to kill a tumor cell or a cancer cell that expresses the antigen against which the $V_{HH}$'s or functional fragments thereof as disclosed herein are directed against, or to reduce or slow the growth and/or proliferation of such a tumor cell or cancer cell, the $V_{HH}$'s are linked to or coupled to, such as chemically coupled to, a radionuclide.

Examples of suitable radionuclides which can be linked to a $V_{HH}$ as disclosed herein in order to provide a cytotoxic compound for the prevention and/or treatment of cancer will be clear to the skilled person and can for example without any limitation be chosen from the group consisting of α-emitting radioisotopes and β-emitting radioisotopes, including but not limited to a radioisotope chosen from the group consisting of Actinium-225, Astatine-211, Bismuth- 212, Bismuth-213, Caesium-137, Chromium-51, Cobalt-60, Dysprosium-165, Erbium-169, Fermium-255, Gold-198, Holium-166, Iodine-125, Iodine-131, Iridium-192, Iron-59, Lead-212, Lutetium-177, Molydenum-99, Palladium-103, Phosphorus-32, Potassium-42, Rhenium-186, Rhenium-188, Samarium-153, Technitium-99m, Radium-223, Ruthenium-106, Sodium-24, Strontium-89, Terbium-149, Thorium-227, Xenon-133, Ytterbium-169, Ytterbium-177, Yttrium-90.

In still further particular embodiments, the radiolabelled $V_{HH}$'s or functional fragments thereof as disclosed herein are labelled with Iodine-131.

Thus, in one aspect, the present disclosure provides radio-labelled $V_{HH}$ sequences or functional fragments thereof specifically directed against a tumor antigen and/or a cancer cell antigen for use in the prevention and/or treatment of cancer.

In particular embodiments, the present disclosure provides radiolabelled $V_{HH}$ sequence or functional fragments thereof specifically directed against a tumor antigen and/or a cancer cell antigen for use in the prevention and/or treatment of cancer, and more specifically for use in the prevention and/or treatment of breast cancer.

In further particular embodiments, the present disclosure provides radiolabelled $V_{HH}$ sequences specifically directed against a tumor antigen and/or a cancer cell antigen having an amino acid sequence, which has at least 80%, preferably at least 85%, such as 90% or 95% or more sequence identity with at least one of SEQ ID NO's: 7 or 8 or functional fragments thereof for use in the prevention and/or treatment of cancer.

In further particular embodiments, the present disclosure provides radiolabelled $V_{HH}$ sequences specifically directed against a tumor antigen and/or a cancer cell antigen having an amino acid sequence chosen from the group consisting of SEQ ID NO's: 7 or 8 or functional fragments thereof for use in the prevention and/or treatment of cancer.

In further particular embodiments, the present disclosure provides $^{131}$I-labelled $V_{HH}$ sequences specifically directed against a tumor antigen and/or a cancer cell antigen for use in the prevention and/or treatment of cancer.

In particular embodiments, the present disclosure provides $^{131}$I-labelled $V_{HH}$ sequences or functional fragments thereof specifically directed against a tumor antigen and/or a cancer cell antigen for use in the prevention and/or treatment of cancer, and more specifically for use in the prevention and/or treatment of breast cancer.

In further particular embodiments, the present disclosure provides $^{131}$I-labelled $V_{HH}$ sequences specifically directed against a tumor antigen and/or a cancer cell antigen having an amino acid sequence, which has at least 80%, preferably at least 85%, such as 90% or 95% or more sequence identity with at least one of SEQ ID NO's: 7 or 8 or functional fragments thereof, for use in the prevention and/or treatment of cancer.

In further particular embodiments, the present disclosure provides $^{131}$I-labelled $V_{HH}$ sequences specifically directed against a tumor antigen and/or a cancer cell antigen having SEQ ID NO: 7 or 8 or functional fragments thereof, for use in the prevention and/or treatment of cancer.

In yet further particular embodiments, the present disclosure provides $^{131}$I-labelled $V_{HH}$ specifically directed against a tumor antigen and/or a cancer cell antigen having an amino acid sequence, which has at least 80%, preferably at least 85%, such as 90% or 95% or more sequence identity with at least one of SEQ ID NO's: 7 or 8 or functional fragments thereof, for use in the prevention and/or treatment of breast cancer.

In yet further particular embodiments, the present disclosure provides $^{131}$I-labelled $V_{HH}$ sequences specifically directed against a tumor antigen and/or a cancer cell antigen having SEQ ID NO: 7 or 8 or functional fragments thereof, for use in the prevention and/or treatment of breast cancer.

In particularly preferred embodiments, the present disclosure provides $V_{HH}$ domains or functional fragments thereof in their monomeric form as well as polypeptides and pharmaceutical compositions comprising a $V_{HH}$ domain or a functional fragment thereof in its monomeric form, i.e. comprising only one $V_{HH}$ domain so as to minimize the in vivo half-life of said polypeptides and pharmaceutical compositions as much as possible.

[Variants of Heavy Chain Variable Domain Sequences]

In certain aspects, the radiolabelled $V_{HH}$ domains or functional fragments thereof specifically binding to a tumor-specific antigen and/or a cancer cell-specific antigen as disclosed herein may be optionally linked to one or more further groups, moieties, or residues via one or more linkers. These one or more further groups, moieties or residues can serve for binding to other targets of interest. It should be clear that such further groups, residues, moieties and/or binding sites may or may not provide further functionality to the heavy chain variable domains as disclosed herein and may or may not modify the properties of the heavy chain variable domain as disclosed herein. Such groups, residues, moieties or binding units may also for example be chemical groups which can be biologically active.

These groups, moieties or residues are, in particular embodiments, linked N- or C-terminally to the heavy chain variable domain, in particularly C-terminally linked.

In particular embodiments, the radiolabelled $V_{HH}$ domains or functional fragments thereof specifically binding to a tumor-specific antigen and/or a cancer cell-specific antigen as disclosed herein may also have been chemically modified. For example, such a modification may involve the introduction or linkage of one or more functional groups, residues or moieties into or onto the heavy chain variable domain. These groups, residues or moieties may confer one or more desired properties or functionalities to the heavy chain variable domain. Examples of such functional groups will be clear to the skilled person.

For example, the introduction or linkage of such functional groups to a heavy chain variable domain can result in an increase in the solubility and/or the stability of the heavy chain variable domain, in a reduction of the toxicity of the heavy chain variable domain, or in the elimination or attenuation of any undesirable side effects of the heavy chain variable domain, and/or in other advantageous properties.

In particular embodiments, the one or more groups, residues, moieties are linked to the heavy chain variable domain via one or more suitable linkers or spacers.

Preferably, the one or more groups, residues or moieties do not confer to the radio-labelled $V_{HH}$ or functional fragments thereof as disclosed herein an extended half-life. Accordingly, in preferred embodiments, the radio-labelled $V_{HH}$ or functional fragments thereof as disclosed herein are non-lifetime extended.

Also preferably, the one or more groups, residues or moieties do not induce multimerization such as dimerization of the radio-labelled $V_{HH}$ or functional fragments thereof as disclosed herein. For example, $V_{HH}$s containing a carboxy-terminal cysteine-containing tag such as a GCC-tag result in an equilibrium mixture of monomeric and dimeric forms (Pruszyski et al. 2013 Nucl Med Biol. 40:52-59). Accordingly, in particular embodiments, the radio-labelled $V_{HH}$ or functional fragments thereof as disclosed herein are devoid of a tag that induces multimerization such as dimerization, more particularly a cysteine-containing tag, even more particularly a GGC-tag.

In particular embodiments, the radio-labelled $V_{HH}$ or functional fragments thereof as disclosed herein are devoid of a C-terminal polypeptide tag such as a His-tag and/or a Myc-tag, preferably untagged. Advantageously, kidney retention was shown to be significantly reduced when using $V_{HH}$s without a carboxy-terminal polypeptide tag compared to polypeptide tagged, such as His-tagged and Myc-His-tagged, $V_{HH}$s.

While the radiolabelled $V_{HH}$ domains specifically binding to a tumor-specific antigen and/or a cancer cell-specific antigen as disclosed herein are preferably in monomeric form (as further described herein), in particular alternative embodiments, two or more of the radiolabelled $V_{HH}$ domains or functional fragments thereof, specifically binding to a tumor-specific antigen and/or a cancer cell-specific antigen as disclosed herein may be linked to each other or may be interconnected. In particular embodiments, the two or more heavy chain variable domains or functional fragments thereof are linked to each other via one or more suitable linkers or spacers. Suitable spacers or linkers for use in the coupling of different heavy chain variable domains as disclosed herein will be clear to the skilled person and may generally be any linker or spacer used in the art to link peptides and/or proteins.

Some particularly suitable linkers or spacers include for example, but are not limited to, polypeptide linkers such as glycine linkers, serine linkers, mixed glycine/serine linkers, glycine- and serine-rich linkers or linkers composed of largely polar polypeptide fragments, or homo- or heterobifunctional chemical crosslinking compounds such as glutaraldehyde or, optionally PEG-spaced, maleimides or NHS esters.

For example, a polypeptide linker or spacer may be a suitable amino acid sequence having a length between 1 and 50 amino acids, such as between 1 and 30, and in particular between 1 and 10 amino acid residues. It should be clear that the length, the degree of flexibility and/or other properties of the linker(s) may have some influence on the properties of the heavy chain variable domains, including but not limited to the affinity, specificity or avidity for the tumor target or the target on a cancer cell. It should be clear that when two or more linkers are used, these linkers may be the same or different. In the context and disclosure of the present disclosure, the person skilled in the art will be able to determine the optimal linkers for the purpose of coupling heavy chain variable domains as disclosed herein without any undue experimental burden.

[Fragments of Heavy Chain Variable Domains]

The present disclosure also encompasses parts, fragments, analogs, mutants, variants, and/or derivatives of the radiolabelled $V_{HH}$ domains specifically binding to a tumor-specific antigen and/or a cancer cell-specific antigen as disclosed herein and/or polypeptides comprising or essentially consisting of one or more of such parts, fragments, analogs, mutants, variants, and/or derivatives, as long as these parts, fragments, analogs, mutants, variants, and/or derivatives are suitable for the purposes envisaged herein. Such parts, fragments, analogs, mutants, variants, and/or derivatives according to the disclosure are still capable of specifically binding to the tumor-specific antigen and/or to the cancer cell-specific antigen.

For example, the disclosure provides a number of stretches of amino acid residues (i.e. small peptides), also referred to herein as CDR sequences of the $V_{HH}$'s as disclosed herein, that are particularly suited for binding to a tumor antigen or cancer antigen. These stretches may be regarded as being functional fragments of the $V_{HH}$'s as disclosed herein and may be present in, and/or may be incorporated into any suitable scaffold (protein), such as but not limited to the $V_{HH}$'s as disclosed herein, in particular in such a way that they form (part of) the antigen binding site of that suitable scaffold or $V_{HH}$. It should however be noted that the disclosure in its broadest sense is not limited to a specific structural role or function that these stretches of amino acid residues may have in the scaffolds or $V_{HH}$'s as disclosed herein, as long as these stretches of amino acid residues allow these scaffolds or $V_{HH}$'s as disclosed herein to specifically bind to a tumor antigen or cancer antigen.

[Nucleic Acid Sequences]

In a further aspect, the present disclosure provides nucleic acid sequences encoding the $V_{HH}$ domain amino acid sequences in the compositions as disclosed herein (or suitable fragments thereof). These nucleic acid sequences can also be in the form of a vector or a genetic construct or polynucleotide. The nucleic acid sequences as disclosed herein may be synthetic or semi-synthetic sequences, nucleotide sequences that have been isolated from a library (and in particular, an expression library), nucleotide sequences that have been prepared by PCR using overlapping primers, or nucleotide sequences that have been prepared using techniques for DNA synthesis known per se.

[Constructs, Vectors, Host Cells]

The genetic constructs as disclosed herein may be DNA or RNA, and are preferably double-stranded DNA. The genetic constructs of the disclosure may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs of the disclosure may be in the form of a vector, such as for example a plasmid, cosmid, YAC, a viral vector or transposon. In particular, the vector may be an expression vector, i.e., a vector that can provide for expression in vitro and/or in vivo (e.g. in a suitable host cell, host organism and/or expression system).

Accordingly, in another further aspect, the present disclosure also provides vectors comprising one or more nucleic acid sequences as disclosed herein.

In still a further aspect, the present disclosure provides hosts or host cells that express or are capable of expressing one or more amino acid sequences as disclosed herein. Suitable examples of hosts or host cells for expression of the $V_{HH}$ sequences, polypeptides of the disclosure will be clear to the skilled person.

[Polypeptides Comprising VHH Domains]

In a further aspect, the present disclosure provides polypeptides (also referred to herein as "polypeptides as disclosed herein") that comprise or essentially consist of at least one $V_{HH}$ sequence of the present disclosure that specifically binds to a tumor-specific antigen and/or a cancer cell-specific antigen. The polypeptides of the disclosure may comprise at least one $V_{HH}$ or functional fragments thereof as disclosed herein and optionally one or more further groups, moieties, residues optionally linked via one or more linkers.

In particularly preferred embodiments, the present disclosure provides polypeptides and pharmaceutical compositions comprising a $V_{HH}$ domain in its monomeric form, i.e.

comprising only one $V_{HH}$ domain so as to minimize the in vivo half-life of said polypeptides and pharmaceutical compositions as much as possible.

In alternative embodiments, however the present disclosure also provides polypeptides and pharmaceutical compositions comprising two or more identical or different $V_{HH}$ domains resulting in a bivalent (or multivalent) or a bispecific or (multispecific) polypeptide.

The polypeptides as disclosed herein may at least contain one or more further groups, moieties or residues for binding to other targets or target proteins of interest. It should be clear that such further groups, residues, moieties and/or binding sites may or may not provide further functionality to the amino acid sequences as disclosed herein (and/or to the polypeptide or composition in which it is present) and may or may not modify the properties of the amino acid sequence as disclosed herein. Such groups, residues, moieties or binding units may also for example be chemical groups which can be biologically and/or pharmacologically active.

Preferably, the further groups, residues or moieties do not confer to the polypeptide an extended half-life. Accordingly, in preferred embodiments, the polypeptides as disclosed herein are non-lifetime extended.

Also preferably, the further groups, residues or moieties do not induce multimerization such as dimerization of the polypeptides as disclosed herein. Accordingly, in particular embodiments, the polypeptides as disclosed herein are devoid of a tag that induces multimerization such as dimerization, more particularly a cysteine-containing tag, even more particularly a GGC-tag.

In particular embodiments, the polypeptides as disclosed herein are devoid of a C-terminal polypeptide tag such as a His-tag and/or a Myc-tag, preferably the polypeptides as disclosed herein are untagged.

These groups, moieties or residues are, in particular embodiments, linked N- or C-terminally to the amino acid sequence as disclosed herein.

[Origin and Form of VHH Sequences, Polypeptides and Compositions as Disclosed Herein]

It should be noted that the disclosure is not limited as to the origin of the $V_{HH}$ sequences or functional fragments thereof, polypeptides or compositions of the disclosure (or of the nucleotide sequences of the disclosure used to express them). Furthermore, the present disclosure is also not limited as to the way that the $V_{HH}$ sequences, polypeptides or nucleotide sequences as disclosed herein have been generated or obtained. Thus, the amino acid sequences as disclosed herein may be synthetic or semi-synthetic amino acid sequences, polypeptides or proteins.

The amino acid sequences, polypeptides and compositions provided by the disclosure can be in essentially isolated form (as defined herein), or alternatively can form part of a polypeptide or composition as disclosed herein, which may comprise or essentially consist of at least one amino acid sequence as disclosed herein and which may optionally further comprise one or more other groups, moieties or residues (all optionally linked via one or more suitable linkers).

[Target Species and Cross-Reactivity]

It will be appreciated based on the disclosure herein that for prophylactic and/or therapeutic, applications, the $V_{HH}$ sequences or functional fragments thereof, polypeptides and compositions as disclosed herein will in principle be directed against or specifically bind to all forms of the tumor-specific antigen and/or a cancer cell-specific antigen. However, where the $V_{HH}$ sequences or functional fragments thereof, polypeptides and compositions as disclosed herein are intended for veterinary purposes, they will be directed against or specifically bind to all forms of the tumor-specific antigen and/or a cancer cell-specific antigen from the species intended to be treated, or they will be at least cross-reactive with all forms of the tumor-specific antigen and/or a cancer cell-specific antigen from the species to be treated. Accordingly, $V_{HH}$ sequences or functional fragments thereof, polypeptides and compositions that specifically bind to all forms of the antigen from one subject species may or may not show cross-reactivity with all forms of the antigen from one or more other subject species. Of course it is envisaged that, in the context of the development of amino acid sequences for use in humans or animals, $V_{HH}$ sequences may be developed which bind to forms of the tumor-specific antigen and/or a cancer cell-specific antigen from another species than that which is to be treated for use in research and laboratory testing.

It is also expected that the $V_{HH}$ sequences and polypeptides of the disclosure will bind to a number of naturally occurring or synthetic analogs, variants, mutants, alleles, parts and fragments of the tumor-specific antigen and/or cancer cell-specific antigen. More particularly, it is expected that the $V_{HH}$ sequences and polypeptides of the disclosure will bind to at least to those analogs, variants, mutants, alleles, parts and fragments of the tumor-specific antigen and/or cancer cell-specific antigen that (still) contain the binding site, part or domain of the (natural/wild-type) antigen to which those $V_{HH}$ sequences and polypeptides bind.

[Targets]

In particular embodiments, $V_{HH}$ domains disclosed herein are obtained by affinity selection against a particular target protein present on and/or specific for a solid tumor and/or a cancer cell. Obtaining suitable polypeptides by affinity selection against a particular solid tumor antigen or cancer cell may for example be performed by screening a set, collection or library of cells that express $V_{HH}$'s on their surface (e.g. bacteriophages) for binding against a tumor-specific antigen and/or a cancer cell-specific antigen; all of which may be performed in a manner known per se, essentially comprising the following non-limiting steps: a) obtaining an isolated solution or suspension of a tumor-specific or cancer cell-specific protein target molecule, which molecule is known to be a target for a potential cancer drug; b) bio-panning phages or other cells from a $V_{HH}$ library against said protein target molecule; c) isolating the phages or other cells binding to the tumor-specific or cancer cell-specific protein target molecule; d) determining the nucleotide sequence encoding the $V_{HH}$ insert from individual binding phages or other cells; e) producing an amount of $V_{HH}$ according to this sequence using recombinant protein expression and f) determining the affinity of said $V_{HH}$ domain for said tumor-specific or cancer cell-specific protein target molecule and optionally g) testing the tumoricidal or anti-cancer activity of said $V_{HH}$ domain in a bio-assay. Various methods may be used to determine the affinity between the $V_{HH}$ domain and the tumor-specific or cancer cell-specific protein target molecule, including for example, enzyme linked immunosorbent assays (ELISA) or Surface Plasmon Resonance (SPR) assays, which are common practice in the art, for example, as described in Sambrook et al. (2001), Molecular Cloning, A Laboratory Manual. Third Edition. Cold Spring Harbor Laboratory Press, Cold Spring Harbor, N.Y. The dissociation constant is commonly used to describe the affinity between a polypeptide and its target molecule. Typically, the dissociation constant of the binding between the polypeptide and its target molecule is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M, such as preferably below $10^{-9}$ M, more preferably below $0.5 \cdot 10^{-9}$ M, such as below $10^{-10}$ M.

In particular embodiments, the VHH fragments as disclosed herein specifically bind to a solid tumor antigen with a dissociation constant of less than $5 \cdot 10^{-9}$ M, such as between about $1 \cdot 10^{-9}$ M and about $5 \cdot 10^{-9}$ M, such as between about $2 \cdot 10^{-9}$ M and about $3 \cdot 10^{-9}$ M.

Tumor-specific antigens or cancer cell-specific antigens are molecules occurring specifically or being expressed specifically and/or abundantly on the surface of tumor cells or cancer cells, respectively, and preferably not or only in relatively low concentration or density on the surface of normal healthy cells. When these tumor-specific or cancer cell-specific antigens are bound to the radiolabelled $V_{HH}$'s as disclosed herein, the corresponding tumor or cancer cells onto which the antigens are expressed are killed or at least arrested, inhibited or reduced in their growth through the mechanism of radiotoxicity.

Suitable tumor-specific or cancer cell-specific target molecules are readily available from existing literature or patent databases for the skilled person and include, without limitation any protein produced in a tumor cell that has an abnormal structure due to mutation, including the abnormal products of ras and p53 genes, tissue differentiation antigens, mutant protein antigens, oncogenic viral antigens, cancer-testis antigens, oncofetal antigens and vascular or stromal specific antigens. Examples of specific tumor antigens include but are not limited to CTAG1B, MAGEA1, the enzyme tyrosinase, alphafetoprotein (AFP), carcinoembryonic antigen (CEA), EBV and HPV, abnormally structured cell surface glycolipids and glycoproteins and HER2, EGFR and variants thereof.

In particular embodiments, the radiolabelled $V_{HH}$ domains as disclosed herein for use in the prevention and/or treatment of cancer are specifically directed against HER2.

In particular embodiments, the present disclosure provides radiolabelled $V_{HH}$ sequence specifically directed against HER2 for use in the prevention and/or treatment of breast cancer.

In further particular embodiments, the present disclosure provides radiolabelled $V_{HH}$ sequences specifically directed against HER2 having an amino acid sequence, which has at least 80%, preferably at least 85%, such as 90% or 95% or more sequence identity with at least one of SEQ ID NO's: 7 or 8 or functional fragments thereof, for use in the prevention and/or treatment of cancer.

In further particular embodiments, the present disclosure provides radiolabelled $V_{HH}$ sequences specifically directed against HER2 having an amino acid sequence chosen from the group consisting of SEQ ID NO's: 7 or 8 or functional fragments thereof, for use in the prevention and/or treatment of cancer.

In further particular embodiments, the present disclosure provides $^{131}$I-labelled $V_{HH}$ sequences or functional fragments thereof, specifically directed against a tumor antigen and/or a cancer cell antigen for use in the prevention and/or treatment of cancer.

In particular embodiments, the present disclosure provides $^{131}$I-labelled $V_{HH}$ sequences or functional fragments thereof specifically directed against HER2 for use in the prevention and/or treatment of cancer, and more specifically for use in the prevention and/or treatment of breast cancer.

In further particular embodiments, the present disclosure provides $^{131}$I-labelled $V_{HH}$ sequences specifically directed against HER2 having an amino acid sequence, which has at least 80%, preferably at least 85%, such as 90% or 95% or more sequence identity with at least one of SEQ ID NO's: 7 or 8 or functional fragments thereof, for use in the prevention and/or treatment of cancer.

In further particular embodiments, the present disclosure provides $^{131}$I-labelled $V_{HH}$ sequences specifically directed against HER2 having SEQ ID NO: 7 or 8 or functional fragments thereof, for use in the prevention and/or treatment of cancer.

In yet further particular embodiments, the present disclosure provides $^{131}$I-labelled $V_{HH}$ or functional fragments thereof specifically directed against HER2 having an amino acid sequence, which has at least 80%, preferably at least 85%, such as 90% or 95% or more sequence identity with at least one of SEQ ID NO's: 7 or 8 or functional fragments thereof for use in the prevention and/or treatment of breast cancer.

In yet further particular embodiments, the present disclosure provides $^{131}$I-labelled $V_{HH}$ sequences or functional fragments thereof specifically directed against HER2 having SEQ ID NO: 7 or 8 for use in the prevention and/or treatment of breast cancer.

In certain non-limiting embodiments, the radio-labelled $V_{HH}$ sequences or functional fragments thereof of the present disclosure are specifically directed against a binding site on HER2, which is different from the Herceptin® (Trastuzumab) binding site on HER2 and/or do not compete with Herceptin® for binding to HER-2, as determined using a suitable competition assay.

In particular embodiments, the radio-labelled $V_{HH}$ sequences of the present disclosure are specifically directed against a binding site on HER2, which is different from (i.e. is not) domain IV of HER2. In yet further particular embodiments, the radio-labelled $V_{HH}$ sequences or functional fragments thereof of the present disclosure are specifically directed against a binding site on HER2, which is different from (i.e. is not) the C-terminus of domain IV of HER2.

Thus, in particular embodiments, the radio-labelled $V_{HH}$ sequences or functional fragments thereof of the present disclosure do not compete with the monoclonal antibody Herceptin® (Trastuzumab) for binding to HER2, as determined using a suitable competition assay.

In certain embodiments, the radio-labelled $V_{HH}$ sequences or functional fragments thereof of the present disclosure do not compete with the monoclonal antibody Pertuzumab (Perjeta®) for binding to HER2, as determined using a suitable competition assay. In further embodiments, the radio-labelled $V_{HH}$ sequences or functional fragments thereof of the present disclosure are specifically directed against a binding site on HER2, which is different from the Perjeta® (Pertuzumab) binding site on HER2, more particularly the radio-labelled $V_{HH}$ sequences of the present disclosure are specifically directed against a binding site on HER2, which is different from (i.e. is not) domain II of HER2.

In certain embodiments, the radio-labelled $V_{HH}$ sequences or functional fragments thereof of the present disclosure do not compete with the monoclonal antibody Trastuzumab (Herceptin®) and the monoclonal antibody Pertuzumab (Perjeta®) for binding to HER2, as determined using a suitable competition assay. In further embodiments, the radio-labelled $V_{HH}$ sequences or functional fragments thereof of the present disclosure are specifically directed against a binding site on HER2, which is different from the Trastuzumab (Herceptin®) and Pertuzumab (Perjeta®) binding site on HER2. In particular embodiments, the radiolabelled $V_{HH}$ sequences of the present disclosure are specifically directed against a binding site on HER2, which is different from (i.e. is not) domain IV of HER2, more particularly, the C-terminus of domain IV of HER2, and domain II of HER2.

A suitable competition assay for determining whether or not an antigen-targeting (e.g. HER2-targeting) radio-labeled $V_{HH}$ or a functional fragment thereof competes with a binding agent, such as a monoclonal body, targeting the same antigen may be, for example but without limitation, an in vivo competition assay. In an in vivo competition assay, the biodistribution of the radio-labelled $V_{HH}$ or the functional fragment thereof is compared in a test animal that was administered the radio-labeled $V_{HH}$ or the functional fragment thereof alone and a test animal that was pre-treated with the binding agent prior to administration of the radio-labelled $V_{HH}$ or the functional fragment thereof, wherein substantially the same biodistribution profile indicates that the radio-labelled $V_{HH}$ or the functional fragment thereof does not compete with the binding agent for binding to the target antigen.

[Forms of Target Antigen]

It will be appreciated based on the disclosure herein that for medical, i.e. prophylactic and/or therapeutic applications, the heavy chain variable domains as disclosed herein will in principle be directed against or specifically bind to several different forms of the tumor-specific antigen or cancer cell-specific antigen. It is also expected that $V_{HH}$'s or functional fragments thereof as disclosed herein will bind to a number of naturally occurring or synthetic analogs, variants, mutants, alleles, parts and fragments of their tumor antigen or cancer antigen. More particularly, it is expected that the heavy chain variable domains as disclosed herein will bind to at least to those analogs, variants, mutants, alleles, parts and fragments of the tumor or cancer antigen that (still) contain the binding site, part or domain of the natural tumor or cancer antigen to which those $V_{HH}$'s or functional fragments thereof bind.

In particular embodiments, where the disclosure provides $V_{HH}$'s or functional fragments thereof that are specifically directed against HER2, it is within the scope of the disclosure that the VHH's as disclosed herein can only bind to HER2 in monomeric form, or can only bind to HER2 in multimeric form, or can bind to both the monomeric and the multimeric form of HER2. Again, in such a case, the $V_{HH}$'s or functional fragments thereof as disclosed herein may bind to the monomeric form of HER2 with an affinity and/or specificity that are the same as, or that are different from (i.e. higher than or lower than), the affinity and specificity with which the $V_{HH}$'s as disclosed herein bind to the multimeric form.

Also, when HER2 can associate with other proteins or polypeptides (e.g. with other ERBB receptors, also referred to as heterodimerization) to form protein complexes (e.g. with multiple subunits), it is within the scope of the disclosure that the $V_{HH}$'s as disclosed herein can bind to HER2 in its non-associated state, or can bind HER2 in its associated state, or can bind to both. Generally, $V_{HH}$ sequences as disclosed herein will at least bind to those forms of HER2 (including monomeric, multimeric and associated forms) that are the most relevant from a biological and/or therapeutic point of view, as will be clear to the skilled person.

[Methods of Production and Manufacturing of VHH Sequences as Disclosed Herein]

The disclosure further provides methods for preparing or generating the $V_{HH}$ domain sequences or functional fragments thereof, as well as methods for producing nucleic acids encoding these and host cells, products and compositions comprising these heavy chain variable domain sequences. Some preferred but non-limiting examples of such methods will become clear from the further description herein.

As will be clear to the skilled person, one particularly useful method for preparing heavy chain variable domain sequences as disclosed herein generally comprises the steps of:

(a) expressing a nucleotide sequence encoding a heavy chain variable domain sequence as disclosed herein or a vector or genetic construct a nucleotide sequence encoding that heavy chain variable domain sequence and (b) optionally isolating and/or purifying the heavy chain variable domain sequence.

In particular embodiments envisaged herein, the tumor-specific or cancer cell-specific a heavy chain variable domain sequences can be obtained by methods which involve generating a random library of $V_{HH}$ sequences and screening this library for an $V_{HH}$ sequence capable of specifically binding to a tumor-specific or cancer cell-specific target protein.

Accordingly, in particular embodiments, methods for preparing a heavy chain variable domain sequence as disclosed herein comprise the steps of
a) providing a set, collection or library of amino acid sequences of $V_{HH}$ domains; and
b) screening said set, collection or library of amino acid sequences for amino acid sequences that can bind to and/or have affinity for the tumor-specific or cancer cell-specific target. and
c) isolating the amino acid sequence(s) that can bind to and/or have affinity for the tumor-specific or cancer cell-specific target.

In such a method, the set, collection or library of $V_{HH}$ sequences may be any suitable set, collection or library of amino acid sequences. For example, the set, collection or library of amino acid sequences may be a set, collection or library of immunoglobulin fragment sequences (as described herein), such as a naïve set, collection or library of immunoglobulin fragment sequences; a synthetic or semi-synthetic set, collection or library of immunoglobulin fragment sequences; and/or a set, collection or library of immunoglobulin fragment sequences that have been subjected to affinity maturation.

In particular embodiments of this method, the set, collection or library of $V_{HH}$ sequences may be an immune set, collection or library of immunoglobulin fragment sequences, for example derived from a mammal that has been suitably immunized with a tumor-specific or cancer cell-specific target or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of $V_{HH}$ sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In other embodiments, the methods for generating the heavy chain variable domain sequences as disclosed herein comprise at least the steps of:
a) providing a collection or sample of cells expressing $V_{HH}$ domain amino acid sequences;
b) screening said collection or sample of cells for cells that express an amino acid sequence that can bind to and/or have affinity for a tumor-specific or cancer cell-specific target; and
c) either (i) isolating said amino acid sequence; or (ii) isolating from said cell a nucleic acid sequence that encodes said amino acid sequence, followed by expressing said amino acid sequence.

The collection or sample of cells may for example be a collection or sample of B-cells. Also, in this method, the sample of cells may be derived from a mammal that has been suitably immunized with a tumor-specific or cancer cell-specific target or with a suitable antigenic determinant based thereon or derived therefrom, such as an antigenic part, fragment, region, domain, loop or other epitope thereof. In one particular embodiment, the antigenic determinant may be an extracellular part, region, domain, loop or other extracellular epitope(s).

In other embodiments, the method for generating a heavy chain variable domain sequence directed against a tumor-specific or cancer cell-specific target may comprise at least the steps of:
a) providing a set, collection or library of nucleic acid sequences encoding a $V_{HH}$ domain amino acid sequence;
b) screening said set, collection or library of nucleic acid sequences for nucleic acid sequences that encode an amino acid sequence that can bind to and/or has affinity for the tumor-specific or cancer cell-specific target; and
c) isolating said nucleic acid sequence, followed by expressing said amino acid sequence.

In the above methods, the set, collection or library of nucleic acid sequences encoding amino acid sequences may for example be a set, collection or library of nucleic acid sequences encoding a naïve set, collection or library of immunoglobulin fragment sequences; a set, collection or library of nucleic acid sequences encoding a synthetic or semi-synthetic set, collection or library of immunoglobulin fragment sequences; and/or a set, collection or library of nucleic acid sequences encoding a set, collection or library of immunoglobulin fragment sequences that have been subjected to affinity maturation.

In particular, in such a method, the set, collection or library of nucleic acid sequences encodes a set, collection or library of $V_{HH}$ domains directed against a tumor-specific or cancer cell-specific antigen (as defined herein).

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

The disclosure also relates to $V_{HH}$ sequences that are obtainable or obtained by the above methods, or alternatively by a method that comprises one of the above methods and in addition at least the steps of determining the nucleotide sequence or amino acid sequence of said $V_{HH}$ sequence; and of expressing or synthesizing said $V_{HH}$ sequence in a manner known per se, such as by expression in a suitable host cell or host organism or by chemical synthesis.

[Isolation of VHH Domains as Disclosed Herein]

In some cases, the methods for producing the amino acid sequences binding specifically to a tumor-specific or cancer cell-specific target as envisaged herein may further comprise the step of isolating from the amino acid sequence library at least one $V_{HH}$ domain having detectable binding affinity for, or detectable in vitro effect on a tumor-specific or cancer cell-specific target. These methods may further comprise the step of amplifying a sequence encoding at least one $V_{HH}$ domain having detectable binding affinity for, or detectable in vitro effect on the activity of a tumor-specific or cancer cell-specific target. For example, a phage clone displaying a particular amino acid sequence, obtained from a selection step of a method described herein, may be amplified by reinfection of a host bacteria and incubation in a growth medium.

In particular embodiments, these methods may encompass determining the sequence of the one or more amino acid sequences capable of binding to a tumor-specific or cancer cell-specific target.

Where a heavy chain variable domain sequence, comprised in a set, collection or library of amino acid sequences, is displayed on a suitable cell or phage or particle, it is possible to isolate from said cell or phage or particle, the nucleotide sequence that encodes that amino acid sequence. In this way, the nucleotide sequence of the selected amino acid sequence library member(s) can be determined by a routine sequencing method.

In further particular embodiments, the methods for producing a $V_{HH}$ domain as envisaged herein comprise the step of expressing said nucleotide sequence(s) in a host organism under suitable conditions, so as to obtain the actual desired amino acid sequence. This step can be performed by methods known to the person skilled in the art.

In addition, the obtained $V_{HH}$ domain sequences having detectable binding affinity for, or detectable in vitro effect on the activity of a tumor-specific or cancer cell-specific target, may be synthesized as soluble protein construct, optionally after their sequence has been identified.

For instance, the $V_{HH}$ domain sequences obtained, obtainable or selected by the above methods can be synthesized using recombinant or chemical synthesis methods known in the art. Also, the amino acid sequences obtained, obtainable or selected by the above methods can be produced by genetic engineering techniques. Thus, methods for synthesizing the $V_{HH}$ sequences obtained, obtainable or selected by the above methods may comprise transforming or infecting a host cell with a nucleic acid or a vector encoding an amino acid sequence having detectable binding affinity for, or detectable in vitro effect on the activity of a tumor-specific or cancer cell-specific target. Accordingly, the $V_{HH}$ sequences having detectable binding affinity for, or detectable in vitro effect on the activity of a tumor-specific or cancer cell-specific target can be made by recombinant DNA methods. DNA encoding the amino acid sequences can be readily synthesized using conventional procedures. Once prepared, the DNA can be introduced into expression vectors, which can then be transformed or transfected into host cells such as *E. coli* or any suitable expression system, in order to obtain the expression of amino acid sequences in the recombinant host cells and/or in the medium in which these recombinant host cells reside.

It should be understood, as known by someone skilled in the art of protein expression and purification, that the $V_{HH}$ domain produced from an expression vector using a suitable expression system may be tagged (typically at the N-terminal or C-terminal end of the amino acid sequence) with e.g. a His-tag or other sequence tag for easy purification.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired heavy chain variable domain sequences may be any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic plant.

Thus, the application also provides methods for the production of $V_{HH}$ domain sequences having detectable binding affinity for, or detectable in vitro effect on the activity of a tumor or cancer cell-specific antigen comprising transforming, transfecting or infecting a host cell with nucleic acid sequences or vectors encoding such $V_{HH}$ sequences and expressing their amino acid sequences under suitable conditions.

In yet another embodiment, the disclosure further provides methods for the manufacture ('or the production of' which is equivalent wording) a pharmaceutical composition as disclosed herein.

In particular embodiments, the disclosure provides methods for producing a pharmaceutical composition as disclosed herein, at least comprising the steps of:
  obtaining at least one $V_{HH}$ or a functional fragment thereof, which specifically binds to a tumor or cancer cell-specific antigen, and
  formulating said $V_{HH}$ or functional fragment thereof in a pharmaceutical composition.

In particular embodiments of these methods, the step of obtaining at least one heavy chain variable domain or functional fragment thereof, which specifically binds to a tumor-specific or cancer cell-specific antigen comprises:
  (a) expressing a nucleotide sequence encoding a $V_{HH}$ or functional fragment thereof, which specifically binds to a tumor-specific or cancer cell-specific antigen, and optionally
  (b) isolating and/or purifying the $V_{HH}$ or functional fragment thereof.

In other particular embodiments of these methods, the step of obtaining at least one $V_{HH}$ or functional fragment thereof, which specifically binds to a tumor-specific or cancer cell-specific protein target comprises:
a) providing a set, collection or library of $V_{HH}$ domain sequences or functional fragments of $V_{HH}$ sequences;
b) screening said set, collection or library of $V_{HH}$ domain sequences or sequences of functional fragments thereof for sequences that specifically bind to and/or have affinity for a tumor antigen, and optionally
c) isolating the $V_{HH}$ sequences or sequences of functional fragments thereof that specifically bind to and/or have affinity for a tumor-specific or cancer cell-specific antigen.

[Radiolabelling of VHH Domains as Disclosed Herein]

In order to be suitable for the prophylactic and therapeutic purposes, especially for the prevention and/or treatment of cancer-related diseases and disorders, where it is intended to kill or at least reduce or slow down the growth or proliferation of a tumor cell or cancer cell that expresses a tumor-specific or cancer cell-specific antigen against which the $V_{HH}$'s as disclosed herein are directed, the $V_{HH}$'s as disclosed herein are linked to or coupled to, such as chemically coupled to, a radionuclide.

Examples of suitable radionuclides which can be linked to a $V_{HH}$ or functional fragments thereof as disclosed herein in order to provide a cytotoxic compound for the prevention and/or treatment of cancer will be clear to the skilled person and can for example without any limitation be chosen from the group consisting of α-emitting radioisotopes and β-emitting radioisotopes, including but not limited to a radioisotope chosen from the group consisting of Actinium-225, Astatine-211, Bismuth-212, Bismuth-213, Caesium-137, Chromium-51, Cobalt-60, Dysprosium-165, Erbium-169, Fermium-255, Gold-198, Holium-166, Iodine-125, Iodine-131, Iridium-192, Iron-59, Lead-212, Lutetium-177, Molydenum-99, Palladium-103, Phosphorus-32, Potassium-42, Rhenium-186, Rhenium-188, Samarium-153, Technitium-99m, Radium-223, Ruthenium-106, Sodium-24, Strontium-89, Terbium-149, Thorium-227, Xenon-133, Ytterbium-169, Ytterbium-177, Yttrium-90.

In still further particular embodiments, the radiolabelled $V_{HH}$'s or functional fragments thereof as disclosed herein are labelled with Iodine-131.

There are various radiolabeling strategies available to incorporate a radionuclide into a protein. The choice of technique for a radiochemist depends primarily on the radionuclide used. The radioactive isotopes of iodine possess the ability to be directly integrated into a molecule by electrophilic substitution or indirectly via conjugation. Radioactive metals on the other hand are labeled via complexation with a chelating agent. Many metallic radionuclides possess the ability to form stable complexes with chelating agents, thus allowing for conjugation with a protein. Radiolabeling molecules with iodine nuclides is of great importance in pharmaceutical radiochemistry. There are over thirty different identified iodine isotopes, but only four are commonly used in radioiodine chemistry: $^{123}$I, $^{124}$I, $^{125}$I, and $^{131}$I.

The direct radioiodination of a protein is a key method for the synthesis of tumor-targeting or cancer cell-targeting radiopharmaceuticals. Generally there are two basic approaches of protein radioiodination. The most straightforward approach is direct protein labeling using electrophilic substitution at tyrosine and histidine residues. The radioiodide is oxidized in situ creating the electrophile *I$^+$. This is done using oxidizing agents like chloramine T, Iodogen® and N-halosuccinimides. The generated electrophile attacks the electron rich of aromatic ring of the amino acid tyrosine, forming a σ-complex. This substitution is performed at the tyrosine residue due to the electron donating hydroxyl group which stabilizes the σ-complex. As the labeling of proteins must take place under mild conditions, the attachment of iodine to the tyrosine is highly suitable.

This method is performed under mild conditions, which is optimal for the labeling of proteins. This is however only possible when the protein contains accessible tyrosine or histidine residues.

Indirect iodination of proteins via conjugation is a frequently used alternative method. In this approach iodine is incorporated by the application of prosthetic groups containing two functional groups to enable both radioiodination and incorporation to the protein. There are a variety of prosthetic groups used for radioiodination, but the most frequently used are N-succinimidyl 5-[*1]iodo-3-pyridinecarboxyl ([$^{131}$I]SIPC) and N-succinimidyl-3-[*I]-iodobenzoate ([*I]SIB). Both active esters are conjugated to amino groups of the protein and exhibit a high in vivo stability.

Another prosthetic group for the acylation of aromatic groups is N-succinimidyl-4-guanidinomethyl-3-[I-131]iodobenzbate ([I-131]SGMIB).

In particular embodiments of the present disclosure, the radiolabelled $V_{HH}$'s as disclosed herein are labelled with Iodine-131 using N-succinimidyl-4-guanidinomethyl-3-[I-131]iodobenzbate ([I-131]SGMIB) or suitable derivatives or variants thereof.

Detailed protocols for radiotherapy are readily available to the expert (Cancer Radiotherapy: Methods and Protocols (Methods in Molecular Medicine), Huddart R A Ed., Human Press 2002). The skilled person knows how to determine an appropriate dosing and application schedule, depending on the nature of the disease and the constitution of the patient. In particular, the skilled person knows how to assess dose-limiting toxicity (DLT) and how to determine the maximum tolerated dose (MTD) accordingly.

In particular embodiments, the radiolabelled $V_{HH}$'s or functional fragments thereof as disclosed herein are administered at a radioactive dosage of lower than about 800 mCi, such as for instance lower than about 150 mCi, such as for instance lower than about 30 mCi, such as lower than about 15 mCi.

In particular embodiments, the radioimmunoconjugate has a specific activity of from about 0.5 mCi/mg to about 8000 mCi/mg, such as for instance from 1 mCi/mg to about 1500 mCi/mg, such as for instance from 1 mCi/mg to about 300 mCi/mg, such as for instance from 1 mCi/mg to about 150 mCi/mg, depending on the radionuclide, and may be administered via an intravenous, intraperitoneal or other route such as intrathecal route. Depending on the desired duration and effectiveness of the treatment, the radionuclide-$V_{HH}$ conjugates as disclosed herein may be administered once or several times, in combination with other therapeutic drugs or radio-sensitizing agents. The amount of the radioimmunoconjugate applied depends on the precise nature of the carcinoma. The dose of radioactivity per administration must be high enough to be effective, but must be below the dose limiting toxicity (DLT).

[VHH Sequences, Polypeptides and Pharmaceutical Compositions for Prophylactic and/or Therapeutic and/or Purposes]

In yet a further aspect, compositions are provided comprising one or more $V_{HH}$ sequences or functional fragments thereof disclosed herein and/or nucleic acid sequences as envisaged herein and optionally at least one acceptable carrier (also referred to herein as pharmaceutical compositions as envisaged herein).

According to certain particular embodiments, the compositions as envisaged herein may further optionally comprise at least one other compound.

In particular embodiments, the compositions as disclosed herein are pharmaceutical compositions.

The pharmaceutical compositions as envisaged herein can be used in the prevention and/or treatment of diseases and disorders associated with tumor-specific or cancer cell-specific target molecules of interest. In particular, the application provides pharmaceutical compositions comprising one or more $V_{HH}$ sequences or functional fragments thereof as envisaged herein that are suitable for prophylactic and/or therapeutic use in a warm-blooded animal, and in particular in a mammal, and more in particular in a human being.

Also provided are pharmaceutical compositions comprising and one or more $V_{HH}$ sequences or functional fragments thereof as envisaged herein that can be used for veterinary purposes in the prevention and/or treatment of one or more cancer-related diseases, disorders or conditions.

Dose, route of administration, application scheme, repetition and duration of treatment will in general depend on the nature of the disease (type, grade, and stage of the tumor or cancer cell etc.) and the patient (constitution, age, gender etc.), and will be determined by the skilled medical expert responsible for the treatment. With respect to the possible doses for the components of the disclosed combination which are described above, it is clear that the medical expert responsible for the treatment will carefully monitor whether any dose-limiting toxicity or other severe side effects occur and undertake the necessary steps to manage those.

Generally, for pharmaceutical use, the $V_{HH}$ sequences or functional fragments thereof as envisaged herein may be formulated as a pharmaceutical preparation or compositions comprising at least one $V_{HH}$ sequence or polypeptide as envisaged herein and at least one pharmaceutically acceptable carrier, diluent or excipient and/or adjuvant, and optionally one or more further pharmaceutically active polypeptides and/or compounds. Such a formulation may be suitable for intraperitoneal, intravenous or other administration such as intrathecal administration. Thus, the $V_{HH}$ sequences or functional fragments thereof, or polypeptides as envisaged herein and/or the compositions comprising the same can for example be administered systemically, locally or topically to the tissue or organ of interest, depending on the location, type and origin of the tumor or cancer cell, and preferably intraperitoneally, intravenously, or intrathecally, depending on the specific pharmaceutical formulation or composition to be used. The clinician will be able to select a suitable route of administration and a suitable pharmaceutical formulation or composition to be used in such administration.

The pharmaceutical dosage forms suitable for injection or infusion can include sterile aqueous solutions or dispersions or sterile powders comprising the active ingredients which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

The amount of the $V_{HH}$ sequences or functional fragments thereof and polypeptides as envisaged herein required for use in prophylaxis and/or treatment may vary not only with the particular $V_{HH}$ sequence or functional fragments thereof or polypeptide selected but also with the route of administration, the nature of the condition being treated and the age and condition of the patient and will be ultimately at the discretion of the attendant physician or clinician. Also the dosage of the $V_{HH}$ sequences or functional fragments thereof and polypeptides envisaged herein may vary depending on the target cell, tumor, tissue, graft, or organ.

In particular, the $V_{HH}$ sequences or functional fragments thereof and polypeptides as envisaged herein will be administered in an amount which will be determined by the medical practitioner based inter alia on the severity of the condition and the patient to be treated. Typically, for each disease indication an optimal dosage will be determined specifying the amount to be administered per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

Useful dosages of the $V_{HH}$'s and polypeptides comprising the $V_{HH}$'s or functional fragments thereof as envisaged herein can be determined by determining their in vitro activity, and/or in vivo activity in animal models.

In certain embodiments, the present disclosure provides a radiolabelled $V_{HH}$ or functional fragments thereof as disclosed herein for use in the prevention and/or treatment of cancer by administering to a subject in need thereof the radiolabelled $V_{HH}$ or functional fragments thereof at a dose of between 10 µg and 1000 µg of $V_{HH}$. In further particular embodiments, the present disclosure provides a radiolabelled $V_{HH}$ or functional fragments thereof as disclosed herein for use in the prevention and/or treatment of cancer by administering to a subject in need thereof the radiolabelled $V_{HH}$ at a dose of between 10 µg and 500 µg of radiolabelled $V_{HH}$, such as in particular between 10 and 100 µg of radiolabelled $V_{HH}$, preferably between 20 and 70 µg of radiolabelled $V_{HH}$, such as between 40 and 60 µg of radiolabelled $V_{HH}$, more preferably but not limited to about 50 µg of radiolabelled $V_{HH}$.

Thus, in certain embodiments, prevention and/or treatment of cancer is achieved by administering a radiolabelled $V_{HH}$ as disclosed herein to a subject in need thereof, characterized in that the $V_{HH}$ or functional fragments thereof has a calculated mean effective dose of between 0.001 and 0.05 mSv/MBq in a subject, such as but not limited to a calculated mean effective dose of between 0.02 and 0.05 mSv/MBq, more preferably between 0.02 and 0.04 mSv/MBq, most preferably between 0.03 and 0.05 mSv/MBq.

Accordingly, the dose of radioactivity applied to the patient per administration has to be high enough to be effective, but must be below the dose limiting toxicity (DLT). For pharmaceutical compositions comprising radiolabeled antibodies, e.g. with 131-Iodine, the maximally tolerated dose (MTD) has to be determined which must not be exceeded in therapeutic settings.

The polypeptides as envisaged herein and/or the compositions comprising the same are administered according to a regimen of treatment that is suitable for preventing and/or treating the disease or disorder to be prevented or treated. The clinician will generally be able to determine a suitable treatment regimen. Generally, the treatment regimen will comprise the administration of one or more $V_{HH}$ sequences or polypeptides, or of one or more compositions comprising the same, in one or more pharmaceutically effective amounts or doses.

The desired dose may conveniently be presented in a single dose or as divided doses (which can again be sub-dosed) administered at appropriate intervals. An administration regimen could include long-term (i.e., at least two weeks, and for example several months or years) or daily treatment. In particular, an administration regimen can vary between once a day to once a month, such as between once a day and once every two weeks, such as but not limited to once a week. Thus, depending on the desired duration and effectiveness of the treatment, pharmaceutical $V_{HH}$ compositions as disclosed herein may be administered once or several times, also intermittently, for instance on a daily basis for several days, weeks or months and in different dosages. The amount applied of the $V_{HH}$ compositions disclosed herein depends on the nature of the particular cancer disease. Multiple administrations are preferred. However, radiolabelled materials are typically administered at intervals of 4 to 24 weeks apart, preferable 12 to 20 weeks apart. The skilled artisan knows however how to choose dividing the administration into two or more applications, which may be applied shortly after each other, or at some other predetermined interval ranging e.g. from 1 day to 1 week.

In particular, the $V_{HH}$ sequences or functional fragments thereof and polypeptides as envisaged herein may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

In the context of this disclosure, "in combination with", "in combination therapy" or "in combination treatment" shall mean that the radiolabelled $V_{HH}$ sequences as disclosed herein or polypeptides comprising the radiolabelled $V_{HH}$ sequences as disclosed herein are applied together with one or more other pharmaceutically active compounds or principles to the patient in a regimen wherein the patient may profit from the beneficial effect of such a combination. In particular, both treatments are applied to the patient in temporal proximity. In a preferred embodiment, both treatments are applied to the patient within four weeks (28 days). More preferably, both treatments are applied within two weeks (14 days), more preferred within one week (7 days). In a preferred embodiment, the two treatments are applied within two or three days. In another preferred embodiment, the two treatments are applied at the same day, i.e. within 24 hours. In another embodiment, the two treatments are applied within four hours, or two hours, or within one hour. In another embodiment, the two treatments are applied in parallel, i.e. at the same time, or the two administrations are overlapping in time.

In particular non-limiting embodiments, the radiolabelled $V_{HH}$ sequences or functional fragments thereof as disclosed herein or polypeptides comprising the radiolabelled $V_{HH}$ sequences as disclosed herein are applied together with one or more therapeutic antibodies or therapeutic antibody fragments. Thus, in these particular non-limiting embodiments, the radioimmunotherapy with the radiolabelled $V_{HH}$ sequences or functional fragments thereof as disclosed herein or polypeptides comprising these radiolabelled $V_{HH}$ sequences or functional fragments thereof is combined with regular immunotherapy with one or more therapeutic antibodies or therapeutic antibody fragments. In further particular embodiments, the radiolabelled $V_{HH}$ sequences or functional fragments thereof as disclosed herein or polypeptides comprising these radiolabelled $V_{HH}$ sequences are used in a combination therapy or a combination treatment method with one or more therapeutic antibodies or therapeutic antibody fragments, such as but not limited to a combination treatment with Trastuzumab (Herceptin®) and/or Pertuzumab (Perjeta®).

For example, the radiolabelled $V_{HH}$ sequences or functional fragments thereof as disclosed herein or polypeptides comprising the radiolabelled $V_{HH}$ sequences and the one or more therapeutic antibodies or therapeutic antibody fragments, such as but not limited to Trastuzumab (Herceptin®) and/or Pertuzumab (Perjeta®), may be infused at the same time, or the infusions may be overlapping in time. If the two drugs are administered at the same time, they may be formulated together in one single pharmaceutical preparation, or they may be mixed together immediately before administration from two different pharmaceutical preparations, for example by dissolving or diluting into one single infusion solution. In another embodiment, the two drugs are administered separately, i.e. as two independent pharmaceutical compositions. In one preferred embodiment, administration of the two treatments is in a way that tumour cells within the body of the patient are exposed to effective amounts of the cytotoxic drug and the radiation at the same time. In another preferred embodiment, effective amounts of both the radiolabelled $V_{HH}$ sequences or functional fragments thereof as disclosed herein or polypeptides comprising the radiolabelled $V_{HH}$ sequences or functional fragments thereof and the one or more therapeutic antibodies or therapeutic antibody fragments, such as but not limited to Trastuzumab (Herceptin®) and/or Pertuzumab (Perjeta® are present at the site of the tumour at the same time. The present disclosure also embraces the use of further agents, which are administered in addition to the combination as defined. This could be, for example, one or more further chemotherapeutic agent(s). It could also be one or more agent(s) applied to prevent, suppress, or ameliorate unwanted side effects of any of the other drugs given. For example, a cytokine stimulating proliferation of leukocytes may be applied to ameliorate the effects of leukopenia or neutropenia.

According to a further aspect, the use of the $V_{HH}$ sequences or functional fragments thereof or polypeptides as envisaged herein that specifically bind to a tumor-specific or cancer cell-specific target molecule of interest is provided for the preparation of a medicament for the prevention and/or treatment of at least one cancer-related disease and/or disorder in which said tumor-specific or cancer cell-specific target molecule is involved. Accordingly, the application provides $V_{HH}$ sequences or functional fragments thereof, polypeptides and pharmaceutical compositions specifically binding to a tumor-specific or cancer cell-specific target, such as but not limited to HER2, for use in the prevention and/or treatment of at least one cancer-related disease and/or disorder in which said tumor-specific or cancer cell-specific target is involved. In particular embodiments, methods for the prevention and/or treatment of at least one cancer-related disease and/or disorder are also provided, comprising administering to a subject in need thereof, a pharmaceutically active amount of one or more $V_{HH}$ sequences or functional fragments thereof, polypeptides and/or pharmaceutical compositions as envisaged herein.

The subject or patient to be treated with the polypeptides described herein may be any warm-blooded animal, but is in particular a mammal and more in particular a human suffering from, or at risk of, a cancer-related disease and/or disorder.

The efficacy of the $V_{HH}$ sequences or functional fragments thereof and polypeptides described herein, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person.

Depending on the tumor-specific or cancer cell-specific target involved, the skilled person will generally be able to select a suitable in vitro assay, cellular assay or animal model to test the $V_{HH}$ sequences or functional fragments thereof and polypeptides described herein for binding to the tumor-specific or cancer cell-specific molecule; as well as for their therapeutic and/or prophylactic effect in respect of one or more cancer-related diseases and disorders.

Accordingly, polypeptides are provided comprising or essentially consisting of at least one radiolabelled $V_{HH}$ sequence or functional fragments thereof for use as a medicament, and more particularly for use in a method for the treatment of a disease or disorder related cancer, an in particular for the prevention and/or treatment of solid tumours.

In particular embodiments, the $V_{HH}$ sequences or functional fragments thereof and polypeptides envisaged herein are used to treat and/or prevent cancers and neoplastic conditions. Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

The $V_{HH}$ sequences and polypeptides as envisaged herein can also be used to treat a variety of proliferative disorders. Examples of proliferative disorders include hematopoietic neoplastic disorders and cellular proliferative and/or differentiative disorders, such as but not limited to, epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, miscellaneous malignant neoplasms, gynecomastia carcinoma, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma), malignant mesothelioma, non-neoplastic polyps, adenomas, familial syndromes, colorectal carcinogenesis, colorectal carcinoma, carcinoid tumors, nodular hyperplasias, adenomas, and malignant tumors, including primary carcinoma of the liver and metastatic tumors, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The following non-limiting Examples describe methods and means according to the invention. Unless stated otherwise in the Examples, all techniques are carried out according to protocols standard in the art. The following examples are included to illustrate embodiments of the invention. Those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Thus, the Figures, Sequence Listing and the Experimental Part/Examples are only given to further illustrate the invention and should not be interpreted or construed as limiting the scope of the invention and/or of the appended claims in any way, unless explicitly indicated otherwise herein.

EXAMPLES

Example 1

Radiolabelling of Anti-HER2 VHH's 1. 131-Iodine Experimental Setup
Radiochemical Procedure The established procedure for radioiodination of $V_{HH}$'s was performed as follows: the necessary amount of sodium [I*] iodide was transferred to a mixture of 3% (v/v) Acetic Acid, 30% (v/v) tert-butylhydroperoxide, and N-succinimidyl 4-[$N^1,N^2$-bis(tert-butyloxycarbonyl) guanodinomethyl]-3-(trimethylstannyl)benzoate, all dissolved in chloroform. While stirring, the mixture was incubated for 50 min at room temperature. Subsequently, [I*]SGMIB-BisBoc was purified on normal phase HPLC, using an ethyl acetate/hexane gradient. Deprotection was achieved after a 15 minute incubation at room temperature with trifluoroacetic acid. Finally, the deprotected [I*]SGMIB was reacted with 100 μg of the anti-HER2 $V_{HH}$ sequence in borate buffer pH 8.5 during 20 min at room temperature. His-tagged [$^{131}$I]SGMIB-bivalent(2Rb17c-2Rb17c), His-tagged [$^{131}$I]SGMIB-monovalent(2Rb17c), and His-tagged [$^{131}$I]SGMIB-monovalent(2Rs15d) $V_{HH}$'s were purified on a PD-10 column equilibrated in PBS.

Quality Control

Quality control was performed by instant thin layer chromatography (iTLC), using glass microfiber sheets impregnated silica gel strips (Varian, Lake Forest, Calif., USA), ran with PBS, pH 7.4. In parallel, analytical radio-HPLC, using a polystyrene divinylbenzene copolymer reversed-phase column (PLRP-S 300 Å, 5 μm, 250/4 mm, Agilent, Diegem, Belgium) was performed. A mixture of 0.1% TFA in water and acetonitrile was used in the following protocol: 0-5 min 25% acetonitrile; 5-7 min 25-34% acetonitrile; 7-10 min 75-100% acetonitrile; 10-25 min 100% acetonitrile at a flow rate of 1 ml/min.

Example 2

Biodistribution and Dosimetry of Radiolabelled Anti-HER2 VHH's in Tumor HER2+Xenografted Mice Female 10-12 week old Balb c nu/nu athymic mice were implanted with 60-day continuous release 17-β-estradiol pellets (0.72 mg, Innovative Research of America: Sarasota, Fla., USA) on their back 2 days prior to tumor implantation. HER2$^+$/luciferase$^+$ tumor cells (5×10$^6$) in 50% Martigel (BD Biosciences, Bedford, Mass., USA) were injected subcutaneously into the right flank and grown until they reached a volume of 350-500 mm$^3$.

Figure 1:
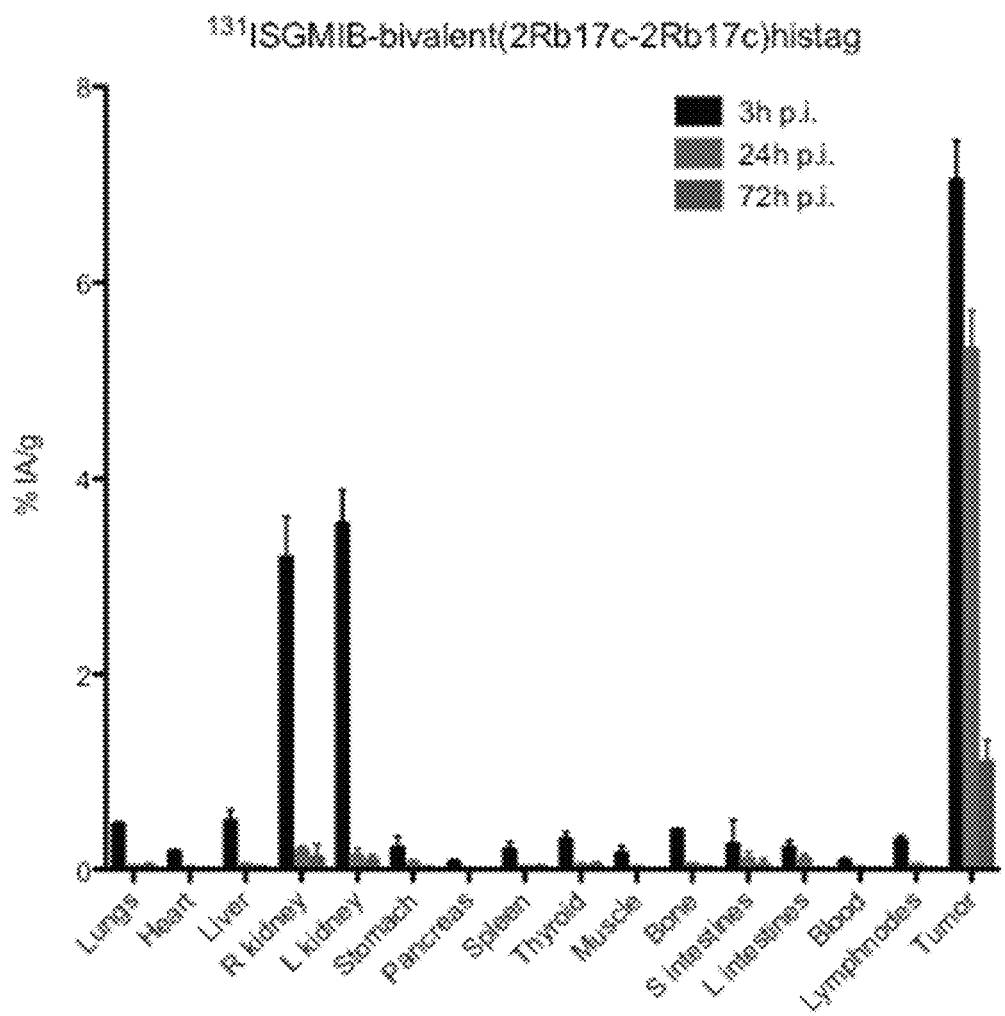
FIG. 1: After injection of the His-tagged [$^{131}$I]SGMIB-labeled bi-valent anti-HER2 $V_{HH}$ 2 Rb17c, different tissues of interest are counted for $^{131}$I activity in an automated gamma counter. Uptake values were expressed as % injected Activity/gram tissue (% IA/g). The obtained data were used to calculate tumor to healthy tissue ratios. Radiation dose estimates for the adult human female were calculated from the biodistribution data of mice using OLINDA 1.0 software, using a voiding bladder interval of 1 h. The calculations were based on time-activity curves to determine the number of disintegrations in organs. Organ doses and effective dose were calculated using the appropriate weighting factors for the various organs.
Figure 3:
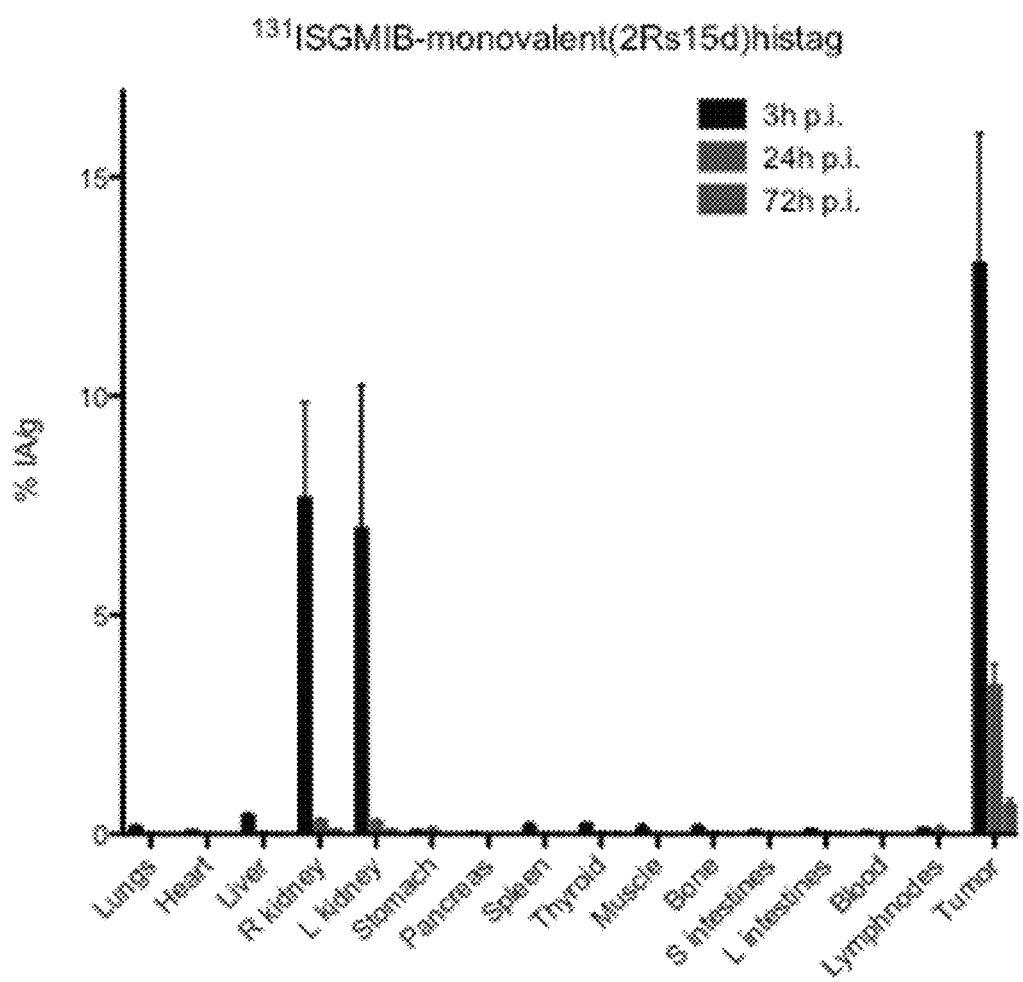
FIG. 3: After injection of the His-tagged [$^{131}$I]SGMIB-labeled mono-valent anti-HER2 $V_{HH}$ 2Rs15d, different tissues of interest are counted for $^{131}$I activity in an automated gamma counter. Uptake values were expressed as % injected Activity/gram tissue (% IA/g). The obtained data were used to calculate tumor to healthy tissue ratios. Radiation dose estimates for the adult human female were calculated from the biodistribution data of mice using OLINDA 1.0 software, using a voiding bladder interval of 1 h. The calculations were based on time-activity curves to determine the number of disintegrations in organs. Organ doses and effective dose were calculated using the appropriate weighting factors for the various organs.

Xenografted mice were killed by an overdose of isoflurane after an intraveneous injection of His-tagged [$^{131}$I]SGMIB-labeled anti-HER2 $V_{HH}$'s bivalent 2Rb17c (FIG. 1; Table 3), His-tagged [$^{131}$I]SGMIB-labeled monovalent 2Rb17c (FIG. 2; Table 4)) and His-tagged [$^{131}$I]SGMIB-labeled monovalent 2Rs15d (FIG. 3; Table 5) and dissected at 3, 24, and 72 h post injection, after which tissues of interest were removed, weighed, and counted for $^{131}$I activity in an automated gamma counter. Uptake values were expressed as % injected Activity/gram tissue (% IA/g).

After injection of the His-tagged [$^{131}$I]SGMIB-labeled anti-HER2 $V_{HH}$'s, tissues of interest were removed, weighed, and counted for $^{131}$I activity in an automated gamma counter.

The obtained data (expressed as % IA/g) were used to calculate the corresponding tumor to healthy tissue ratios (Table 6)

TABLE 3

| | 131I-Biv(2Rb17c2Rb17c)2 | | | | | |
|---|---|---|---|---|---|---|
| | 4 H MEAN | SD | 24 H MEAN | SD | 72 H MEAN | SD |
| Lungs | 0.46 | 0.02 | 0.03 | 0.01 | 0.03 | 0.03 |
| Heart | 0.18 | 0.02 | 0.02 | 0.001 | 0.01 | 0.001 |
| Liver | 0.50 | 0.11 | 0.04 | 0.01 | 0.02 | 0.005 |
| Right Kidney | 3.19 | 0.41 | 0.20 | 0.04 | 0.12 | 0.13 |
| Left Kidney | 3.53 | 0.35 | 0.14 | 0.08 | 0.09 | 0.05 |
| Stomach | 0.22 | 0.12 | 0.06 | 0.03 | 0.01 | 0.01 |
| Pancreas | 0.07 | 0.03 | 0.01 | 0.01 | 0.002 | 0.002 |
| Spleen | 0.21 | 0.08 | 0.02 | 0.002 | 0.03 | 0.01 |
| Thyroid | 0.31 | 0.08 | 0.04 | 0.02 | 0.04 | 0.03 |
| Muscle | 0.16 | 0.08 | 0.02 | 0.01 | 0.003 | 0.001 |
| Bone | 0.40 | 0.01 | 0.05 | 0.01 | 0.02 | 0.01 |
| S intestine | 0.26 | 0.25 | 0.10 | 0.07 | 0.04 | 0.07 |
| L intestine | 0.22 | 0.07 | 0.10 | 0.05 | 0.01 | 0.01 |
| Blood | 0.09 | 0.03 | 0.02 | 0.01 | 0.01 | 0.001 |
| Lymphnodes | 0.30 | 0.05 | 0.04 | 0.01 | 0.01 | 0.01 |
| Tumor | 7.05 | 0.40 | 5.32 | 0.40 | 1.10 | 0.23 |

TABLE 4

| | 131I-SGMIB-2Rb17c | | | | | |
|---|---|---|---|---|---|---|
| | 4 H MEAN | SD | 24 H MEAN | SD | 72 H MEAN | SD |
| Lungs | 0.57 | 0.02 | 0.15 | 0.05 | 0.07 | 0.05 |
| Heart | 0.07 | 0.02 | 0.01 | 0.002 | 0.004 | 0.002 |
| Liver | 0.39 | 0.31 | 0.04 | 0.02 | 0.02 | 0.01 |
| Right Kidney | 3.77 | 1.25 | 0.19 | 0.03 | 0.05 | 0.02 |
| Left Kidney | 4.28 | 2.01 | 0.19 | 0.03 | 0.07 | 0.02 |
| Stomach | 0.08 | 0.004 | 0.01 | 0.005 | 0.02 | 0.03 |
| Pancreas | 0.03 | 0.001 | 0.002 | 0.0002 | 0.001 | 0.001 |
| Spleen | 0.23 | 0.06 | 0.03 | 0.01 | 0.01 | 0.004 |
| Thyroid | 0.41 | 0.12 | 0.04 | 0.03 | 0.03 | 0.02 |
| Muscle | 0.15 | 0.05 | 0.01 | 0.004 | 0.003 | 0.003 |
| Bone | 0.26 | 0.09 | 0.06 | 0.02 | 0.01 | 0.002 |
| S intestine | 0.16 | 0.06 | 0.01 | 0.01 | 0.04 | 0.05 |
| L intestine | 0.12 | 0.01 | 0.01 | 0.004 | 0.01 | 0.01 |
| Blood | 0.06 | 0.002 | 0.01 | 0.002 | 0.005 | 0.002 |
| Lymphnodes | 0.14 | 0.03 | 0.01 | 0.01 | 0.01 | 0.01 |
| Tumor | 9.95 | 0.75 | 1.64 | 0.15 | 0.13 | 0.03 |

TABLE 5

131I-SGMIB-2Rs15d

| | 4 H MEAN | SD | 24 H MEAN | SD | 72 H MEAN | SD |
|---|---|---|---|---|---|---|
| Lungs | 0.16 | 0.03 | 0.02 | 0.003 | 0.01 | 0.01 |
| Heart | 0.07 | 0.004 | 0.01 | 0.002 | 0.002 | 0.0005 |
| Liver | 0.41 | 0.06 | 0.03 | 0.01 | 0.01 | 0.005 |
| Right Kidney | 7.66 | 2.19 | 0.28 | 0.07 | 0.09 | 0.02 |
| Left Kidney | 6.96 | 3.28 | 0.28 | 0.05 | 0.08 | 0.03 |
| Stomach | 0.07 | 0.01 | 0.07 | 0.08 | 0.01 | 0.003 |
| Pancreas | 0.02 | 0.01 | 0.004 | 0.002 | 0.001 | 0.0003 |
| Spleen | 0.17 | 0.08 | 0.01 | 0.005 | 0.01 | 0.005 |
| Thyroid | 0.22 | 0.03 | 0.03 | 0.01 | 0.03 | 0.03 |
| Muscle | 0.14 | 0.09 | 0.01 | 0.0003 | 0.001 | 0.001 |
| Bone | 0.15 | 0.07 | 0.04 | 0.01 | 0.01 | 0.004 |
| S intestine | 0.07 | 0.02 | 0.02 | 0.01 | 0.01 | 0.01 |
| L intestine | 0.09 | 0.02 | 0.03 | 0.01 | 0.01 | 0.01 |
| Blood | 0.05 | 0.004 | 0.01 | 0.002 | 0.003 | 0.001 |
| Lymphnodes | 0.11 | 0.02 | 0.08 | 0.11 | 0.01 | 0.004 |
| Tumor | 13.01 | 2.98 | 3.36 | 0.51 | 0.66 | 0.13 |

TABLE 6

| | 131I-SGMIB-Biv(2Rb17c)2 | | | 131I-SGMIB-Monov(2Rb17c) | | | 131I-SGMIB-Monov(2Rs15d) | | |
|---|---|---|---|---|---|---|---|---|---|
| | 3 H | 24 H | 72 H | 3 H | 24 H | 72 H | 3 H | 24 H | 72 H |
| T/Lu | 15.34 | 172.42 | 38.49 | 17.33 | 10.76 | 1.89 | 79.02 | 222.59 | 96.63 |
| T/He | 38.71 | 261.95 | 176.09 | 133.64 | 216.65 | 36.52 | 194.74 | 314.47 | 318.22 |
| T/Li | 14.21 | 128.21 | 49.13 | 25.31 | 36.68 | 5.69 | 31.67 | 122.30 | 48.94 |
| T/Rki | 2.21 | 26.97 | 8.87 | 2.64 | 8.71 | 2.83 | 1.70 | 11.90 | 7.56 |
| T/Lki | 2.00 | 38.48 | 12.02 | 2.33 | 8.62 | 1.78 | 1.87 | 12.11 | 8.37 |
| T/St | 31.97 | 85.86 | 76.58 | 124.91 | 152.63 | 6.24 | 186.49 | 50.68 | 115.10 |
| T/Pa | 97.05 | 795.12 | 477.74 | 307.58 | 930.94 | 119.37 | 609.19 | 811.41 | 932.66 |
| T/Sp | 34.35 | 232.62 | 42.66 | 43.65 | 55.55 | 18.93 | 77.11 | 259.52 | 87.30 |
| T/Th | 23.10 | 119.23 | 26.17 | 24.28 | 46.79 | 4.49 | 60.09 | 118.56 | 25.54 |
| T/M | 42.75 | 257.33 | 316.20 | 65.72 | 196.97 | 51.74 | 92.44 | 323.57 | 1177.17 |
| T/Bo | 17.49 | 114.93 | 63.91 | 38.20 | 26.93 | 9.63 | 88.56 | 84.46 | 48.86 |
| T/SI | 27.53 | 51.85 | 24.64 | 63.58 | 130.90 | 3.64 | 189.13 | 172.86 | 119.68 |
| T/LI | 31.42 | 52.52 | 158.27 | 82.78 | 159.28 | 14.19 | 141.84 | 126.33 | 70.96 |
| T/B | 78.29 | 313.63 | 151.63 | 178.48 | 162.05 | 28.57 | 239.96 | 361.37 | 224.33 |
| T/Ly | 23.61 | 134.42 | 115.68 | 69.38 | 178.03 | 17.19 | 115.57 | 44.10 | 121.09 |

Extremely high ratios were achieved, highlighting the very low uptake in healthy tissues and thus the low toxicity. Ratios of this extend as observed using $^{131}$Iodine-SGMIB-labeled His-tagged VHHs have never been published for other radioimmunobiologicals so far. Since other formats of radiolabeling VHH with isotopes such as 99mTc, 68Ga or even 131I had typically yielded a very high % IA/g tissue retained in the kidneys, it was especially surprising to detect the very low uptake value in the kidneys for the His-tagged 2Rs15d or 2Rb17c VHHs when labeled with 131I using SGMIB. These kidney uptake values were even lower than what had been reported recently for another Her2-targeting VHH termed 5F7GGC in (Pruszynski et al., J. Nucl. Med.; 2014; April; 55(4):650-6.; DOI: 10.2967/jnumed.113.127100). Accordingly, using the same method as described in the beforementioned manuscript for calculating radiation absorbed doses to the kidneys and based on the % IA/g tissue values obtained at 3 h and 24 h post injection, values of 1055 cGy/mCi or 586 cGy/mCi were obtained for the 131I-SGMIB labeled His-tagged monovalent 2Rs15d or 2Rb17c $V_{HH}$'s, respectively, which was lower than the values obtained for 5F7GGC, based on biodistribution data from the aforementioned manuscript.

As another method to calculate the absorbed radiation doses in various body tissues, mean effective dose estimates for the adult human female were calculated from the biodistribution data of mice using OLINDA 1.0 software, using a 1 h voiding bladder interval (extrapolation of mouse data to human prediction). These calculations yielded mean effective dose estimates for His-tagged [$^{131}$I]SGMIB-labeled anti-HER2 $V_{HH}$'s monovalent 2Rs15d, His-tagged [$^{131}$I]SGMIB-labeled monovalent 2Rb17c and His-tagged [$^{131}$I]SGMIB-labeled bivalent 2Rb17c of respectively 0.031±0.00040 mSv/MBq, 0.032±0.00081 mSv/MBq and 0.032±0.00026 mSv/MBq (values represent mean±SD).

Example 3

Imaging and Radioimmunotherapy of Multiple Myeloma with Anti-Idiotypic $V_{HH}$'s Multiple myeloma (MM) is characterized by the monoclonal expansion of malignant plasma cells in the bone marrow (BM) and the production of monoclonal protein (M-protein). With the implementation of autologous stem cell transplantation and high-dose chemotherapy using dexamethasone, bortezomib, thalidomide and lenalidomide, the survival rate has improved but MM patients still relapse, even if they achieve complete remission (CR). Therefore, new therapeutic strategies are needed to target residual malignant cells and eliminate minimal residual disease (MRD) in order to improve patient outcome.

Here, we take advantage of the M-protein present in the murine 5T2MM model to prove the potential use of $V_{HH}$'s in MM. The 5TMM models are syngeneic, immunocompetent models that resemble human MM clinically and biologically. The best characterized are the 5T33MM and the 5T2MM models. The former represents an aggressive tumor, which develops in a short period of time (4 weeks), whereas the latter represents a more moderate tumor that develops over a period of 3 months. Both express different idiotypes (5T33MMid and 5T2MMid, respectively) on the cell membrane surface.

Figure 6A:
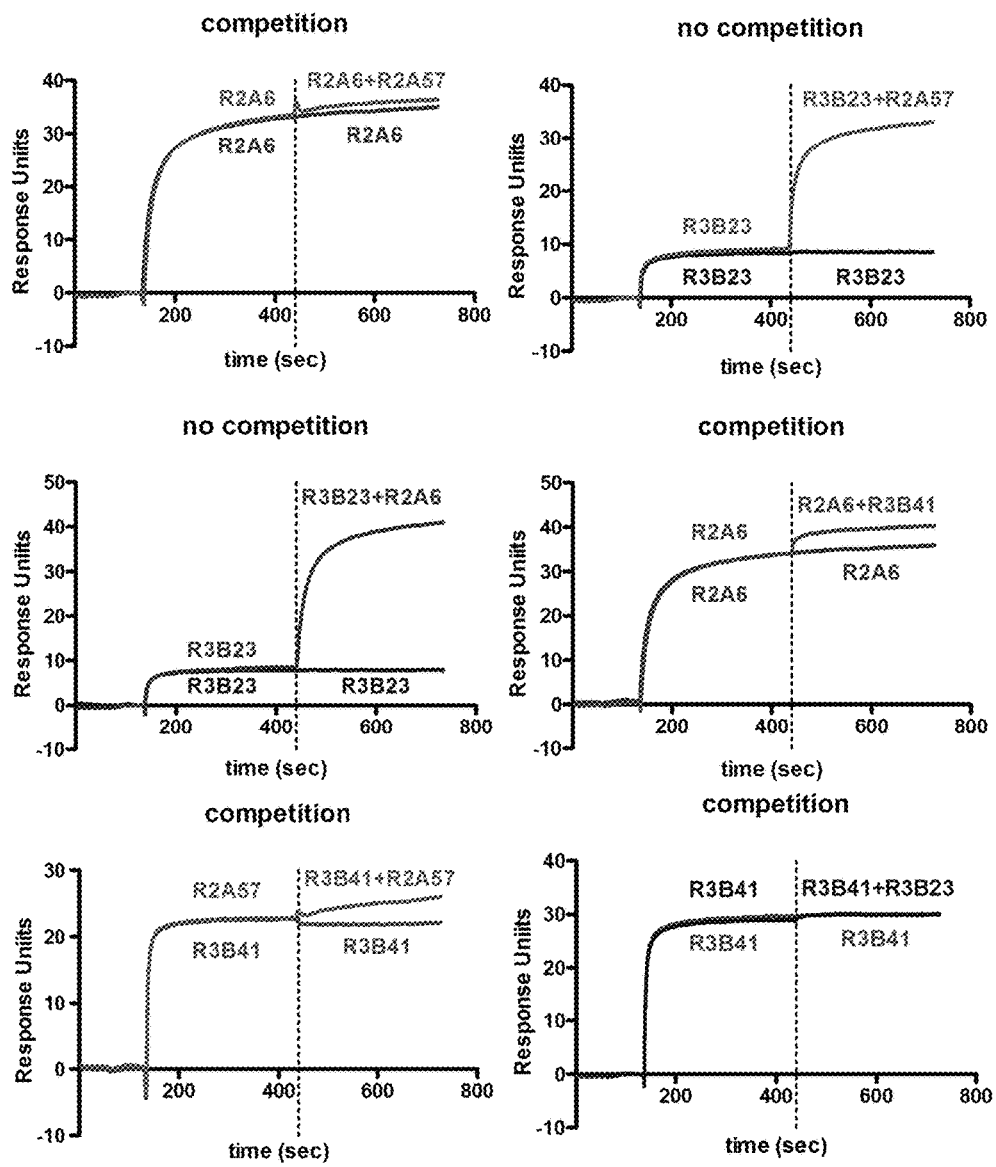
FIGS. 6A-6B: $V_{HH}$'s R2A6, R2A57, R3B23 and R3B41 bind close, largely overlapping epitopes on the 5T2MM-idiotype. (A) Representative competition studies between $V_{HH}$'s for binding to immobilized 5T2MM idiotype, as determined by Surface Plasmon Resonance measurements. In each graph, the competition between two $V_{HH}$'s at equimolar concentrations (1 mM each) is shown. Two $V_{HH}$'s compete for the same epitope on the 5T2MMid when the saturated binding of one $V_{HH}$ in the first phase hinders the binding of the competing $V_{HH}$ in a second phase. (B) Proposed model for the binding of the 4 investigated $V_{HH}$'s on overlapping epitopes of the 5T2MMid antigen.
Figure 6B:
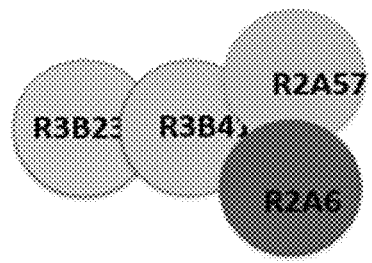
Figure 7:
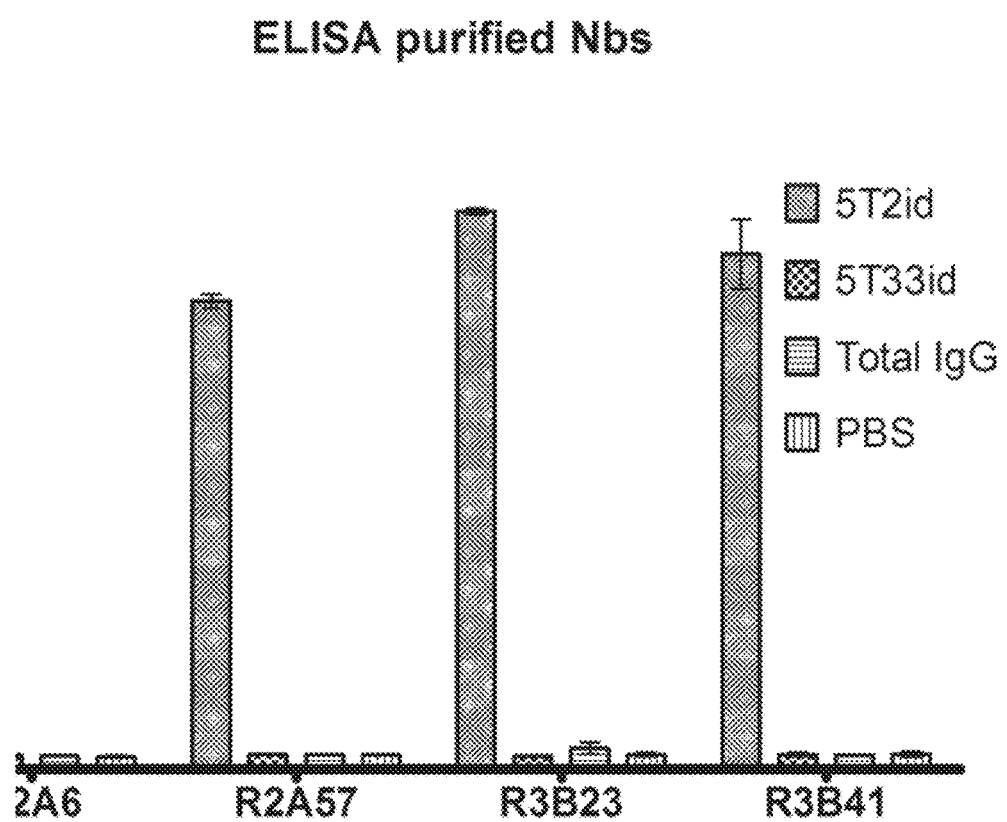
FIG. 7: Specific recognition of 5T2MMid by $V_{HH}$'s R2A6, R2A57, R3B23 and R3B41. ELISA of purified $V_{HH}$'s harboring His- and HA-tags on immobilized 5T2MMid, 5T33MMid, total mouse IgG or blank wells. Bound $V_{HH}$'s were detected using an HRP-coupled anti-HA secondary antibody. Results represent the mean±standard error of the mean of three independent experiments.
Figure 8:
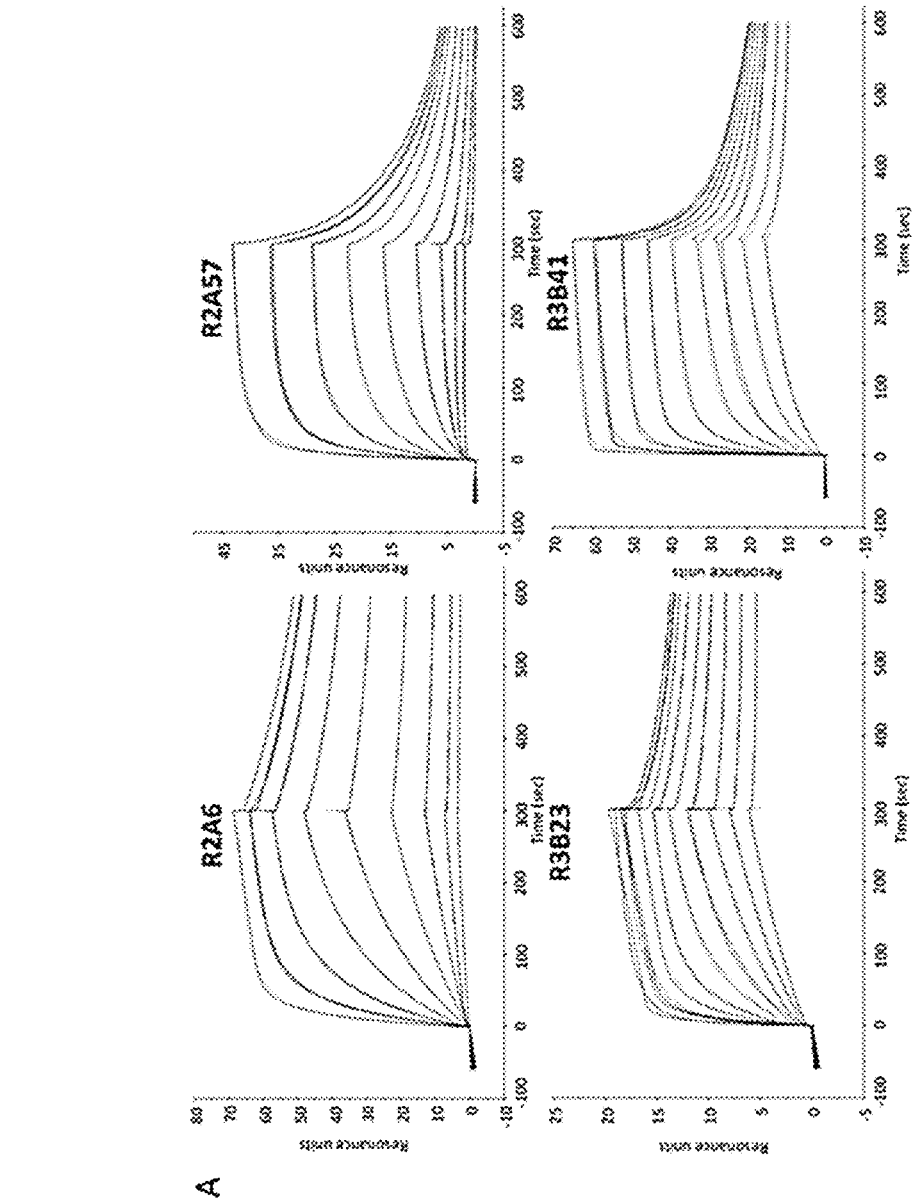
FIG. 8: Binding affinity measurement of $V_{HH}$'s R2A6, R2A57, R3B23 and R3B41. (A) Surface plasmon resonance (SPR) sensograms of purified $V_{HH}$'s on immobilized 5T2MM idiotype. Each sensogram represents a first phase binding of a 2-fold dilution series of $V_{HH}$'s from 500 to 1.95 nM, followed by dissociation from the antigen in a second phase. (B) Calculated association rate constants ka1 and ka2, dissociation rate constants kd1 and kd2 and equilibrium dissociation constant KD of purified $V_{HH}$'s by SPR on immobilized 5T2MM idiotype, based on curves fitted with a two-phase binding model.
Figure 9:
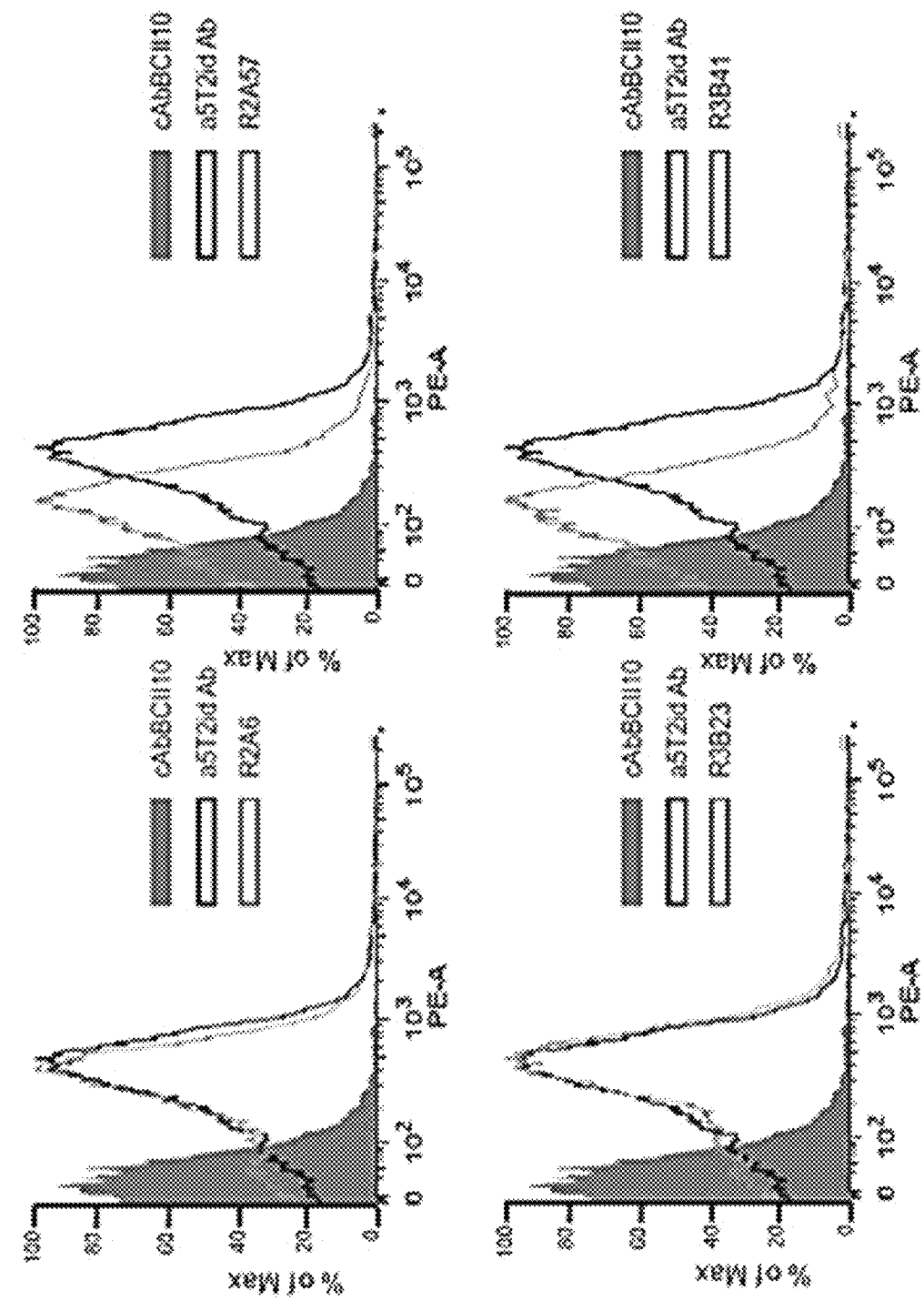
FIG. 9: Flow cytometric analysis of purified HA-tagged $V_{HH}$'s on 5T2MM cells.

By immunization of a dromedary with purified 5T2MM M-protein and a simple selection method, we were able to select, produce and purify a panel of very specific anti-5T2MM-idiotype $V_{HH}$'s (α5T2MMid-Nbs) that recognize nearby epitopes on the idiotype (FIG. 6). After in vitro characterization of these $V_{HH}$'s, R3B23 came up as the best binder (see FIGS. 7, 8 and 9) and was therefore selected for in vivo testing. R3B23 was labeled with radionuclides $^{99m}$Technetium ($^{99m}$Tc) and $^{177}$Lutetium ($^{177}$Lu) using previous established protocols. $^{99m}$Tc (half-life: 6 h) is used in SPECT for nuclear medicine imaging techniques, whereas $^{177}$Lu (half-life: 6.7 days) is mainly used for therapeutic applications due to the emission of low-energy β-minus particles.

Figures 4A, 4B, 4C, 4D:
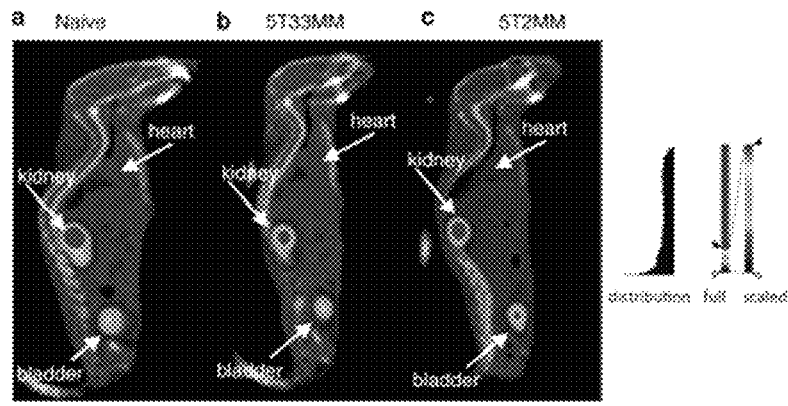
FIGS. 4A-4H: Whole-body imaging and biodistribution of $^{99m}$Tc-labeled $V_{HH}$'s. Sagittal view of the fused SPECT/micro-CT scan images at 1 h post injection (p.i.) of $^{99m}$Tc-cAbBCII10 (a-c) or $^{99m}$Tc-R3B23 (e-g) in naive (a, e), 5T33MM (b, f) or 5T2MM mice (c, g). One representative image of each group is shown. The National Institutes Health color scale is used, and all images are equally scaled down to 25% relative to maximum activity in image, corrected for injected activity. Uptake values of $^{99m}$Tc-cAbBCII10 (d) and $^{99m}$Tc-R3B23 (h) in naive, 5T33MM and 5T2MM diseased mice at 1.5 h p.i. The amount of radioactivity is represented as the percentage of injected activity per gram tissue or organ (% IA/g) corrected for decay.
Figures 4E, 4F, 4G, 4H:
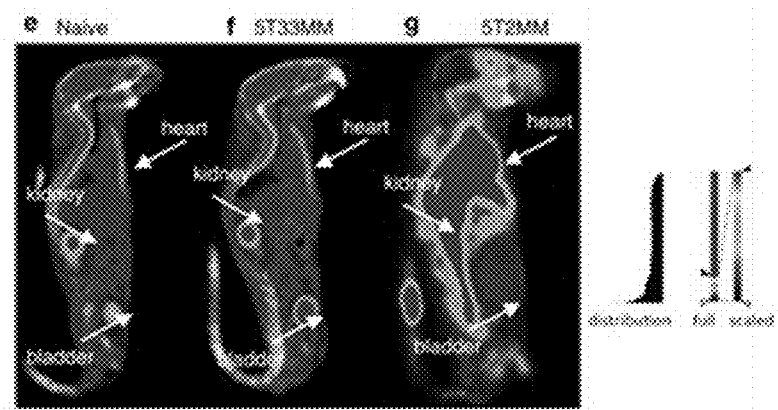

First, we studied the specificity of R3B23 in vivo. At 1 h post injection (p.i.), anesthetized mice were imaged using pinhole SPECT and micro-CT, as described previously. At 30 min after imaging, the mice were killed, different organs were removed, weighed and the radioactivity was measured. Fused SPECT/micro-CT images obtained from naive mice with non-targeting control $V_{HH}$ $^{99m}$Tc-cAbBCII10 showed tracer uptake only in the bladder and kidneys (FIG. 4a). Biodistribution experiments (FIG. 4d) confirmed a high tracer uptake in both kidneys (>200% IA/g) and only marginal levels of uptake in other organs (ranging from 0.20±0.04% IA/g in muscle tissue to 1.02±0.26% IA/g in lungs) as expected for unbound tracers that are eliminated from the body through renal filtration. Importantly, similar results were observed in naive mice injected with $^{99m}$Tc-R3B23 (FIGS. 4e and h) indicating that R3B23 does not bind to circulating immunoglobulins or other in vivo targets. SPECT/micro-CT scan images and biodistribution studies of terminally diseased 5T33MM mice injected with either $^{99m}$Tc-cAbBCII10 (FIGS. 4b and d) or $^{99m}$Tc-R3B23 (FIGS. 4f and h) and 5T2MM mice injected with $^{99m}$Tc-cAbBcII10 (FIGS. 4c and d) showed analogous patterns with a high tracer uptake in kidneys and bladder and a low uptake in all other organs, demonstrating that MM disease does not influence $V_{HH}$ uptake. SPECT/micro-CT scan images of 5T2MM mice injected with $^{99m}$Tc-R3B23 (FIG. 4g) revealed a systemic tracer uptake, which was confirmed by biodistribution studies (FIG. 4h). The up to 100-fold-elevated tracer levels in blood (44.56±2.54% IA/g) can be attributed to binding of the anti-idiotypic $V_{HH}$ to the high levels of circulating M-protein in this late-stage disease model. The elevated tracer blood-pool activity accounts for the decreased uptake observed in the kidneys (circa 8% IA/g) and is responsible for the elevated uptake in other organs (ranging from 0.91±0.04% IA/g in the muscle to 11.63±2.35% IA/g in the lungs). It is noteworthy that the in vivo increase in circulating M-protein can be monitored over time using SPECT/micro-CT scans with $^{99m}$Tc-R3B23 (FIG. 10). In conclusion, the biodistribution studies demonstrate that R3B23 does not bind to any target in healthy mice or to M-protein with a different idiotype, and it is therefore truly anti-idiotypic.

Finally, we evaluated the effect of $V_{HH}$ R3B23 conjugated with $^{177}$Lutetium ($^{177}$Lu-R3B23) on tumor growth. One week after inoculation of 5T2MM cells into naive mice, we started weekly treatments with intravenously administered $^{177}$Lu-R3B23 or negative control $^{177}$Lu-cAbBCII10. After 5 weeks of treatment, animals were imaged using SPECT/micro-CT scans with $^{99m}$Tc-R3B23 (FIG. 5). On the basis of micro-CT images, an ellipsoid region of interest was drawn around the heart. Tracer uptake in heart, as a measurement of blood-pool activity, is expressed as the counts in the tissue divided by the injected activity/cubic centimeter (% IA/cm$^3$). The % IA/cm$^3$ detected in the heart of mice treated with $^{177}$Lu-R3B23 (5.55±1.42) was significantly lower than the values measured in untreated mice (10.03±0.27; P<0.005) and mice treated with control $V_{HH}$ $^{177}$Lu-cAbBcII10 (9.19±0.84; P<0.05). The lower blood value of $^{99m}$Tc-R3B23 uptake in mice treated with $^{177}$Lu-R3B23 is not due to in vivo competition with the therapeutic $^{177}$Lu-labeled $V_{HH}$, as the latter was already systemically cleared. Indeed, the 10 μg $^{99m}$Tc-R3B23 injection and subsequent SPECT/micro-CT scanning were performed 5 days after injection with 10 μg $^{177}$Lu-$V_{HH}$. Moreover, at this time point, no signal could be detected in the SPECT $^{177}$Lu-channel in any group, despite the long physical half-life of $^{177}$Lu (FIG. 5).

After 7 weeks of treatment, the mice were killed and the tumor burden was assessed by the measurement of serum M-protein by capillary electrophoresis and determining plasmacytosis on the May-Grünwald Giemsa-stained cytosmears of BM. In the untreated mice, borderline amounts of malignant plasma cells (<10%) and circulating M-protein (between 0.06-0.16 g/dl) could be detected, but no measurable values could be obtained in the other two groups (data not shown). However, this indicates that SPECT/micro-CT scanning with $V_{HH}$'s is more sensitive for early detection of M-protein than capillary electrophoresis. In mice, splenomegaly is one of the hallmarks of MM-disease. Remarkably, we observed a significant lower spleen weight in mice treated with $^{177}$Lu-R3B23 (0.06±0.02 g) compared with those treated with $^{177}$Lu-cAbBCII10 (0.19±0.01 g; P<0.005) and untreated mice (0.21±0.01 g; P<0.0005). No significant difference was observed between the untreated group and the $^{177}$Lu-cAbBCII10 group. These results indicate that the observed effect in the $^{177}$Lu-R3B23-treated mice is due to a selective targeting of the 5T2MM cells.

In summary, we have here demonstrated, as a proof of principle, that it is possible to produce $V_{HH}$'s against a very specific tumor marker in MM and use them for in vitro detection of 5T2MMid by ELISA and flow cytometry. Moreover, $V_{HH}$'s conjugated with radionuclides were able to monitor disease progression in vivo and target MM cells in a MRD-like setup, thereby providing further evidence for the use of $V_{HH}$'s in the development of novel diagnostic and therapeutic techniques in MM.

Example 4

Targeted Radionuclide Therapy with a $^{177}$Lu-Labeled Anti-HER2 $V_{HH}$

In this study, we focus on $V_{HH}$-based targeted radionuclide therapy of HER2$^{pos}$ xenografted tumors, using the therapeutic radionuclide $^{177}$Lu ($T_{1/2}$=6.72 days, <Eβ>=133 keV).

1. Materials and Methods
a) Cell Line and Culture Conditions

The human ovarian cancer cell line SKOV3 (HER2$^{pos}$) was obtained from American Type Culture Collection (ATCC, Manassas, Va., USA). SKOV3-LUC (HER2$^{pos}$/Luciferase$^{pos}$) was made in-house by transfecting the SKOV3 cells with luciferase-encoding lentiviral particles. SKOV3 cells were cultured using McCoy's 5A medium, SKOV3-LUC in DMEM medium. Both media were enriched with 10% fetal bovine serum, L-Glutamine (2 mM), 100 U/mL of penicillin and 0.1 mg/mL streptomycin. Cells were grown in a humidified atmosphere with 5% CO$_2$ at 37° C. Prior to use for in vitro and in vivo purposes, cells were detached by using trypsin-EDTA. All media and supplements were obtained from Life Technologies (Paisley, UK).

b) $V_{HH}$ Production and Purification

Anti-HER2 $V_{HH}$'s 2Rs15d, 2Rb17c and 1R136b were produced with 3 types of C-terminal amino acid tags: untagged ($V_{HH}$), His-tag ($V_{HH}$-HHHHHH (SEQ ID NO:9)), and Myc-His-tag ($V_{HH}$-AAAEQKLISEEDLNGAA-HHH- HHH (SEQ ID NO:10)). $V_{HH}$'s were expressed in bacteria and purified. Briefly, the sequences were re-cloned into an expression vector either containing a His-tag (pHEN6), a Myc-His-tag (pHEN18), or devoid of any tag (pHEN21). The recombinant vectors were transformed into *E. coli* WK6 cells for $V_{HH}$ expression and extraction of periplasmic proteins. His- and Myc-His-tagged $V_{HH}$'s were further purified by affinity chromatography on His-Select Nickel Affinity Gel (GE Healthcare). Untagged control $V_{HH}$ BcII10, recognizing a bacterial enzyme, and both untagged 2Rb17c and 1R136b were purified on protein A Sepharose beads (GE Healthcare). Final purification of all $V_{HH}$'s was performed through size-exclusion chromatography using Superdex 75 16/60 columns (GE Healthcare) in PBS. Protein purity and integrity were evaluated using SEC on Superdex 75 10/30 (GE Healthcare) in PBS, at flow rate 0.5 mL/min. In addition, ESI-Q-ToF-MS (Waters,Micromass) was performed, in positive mode.

c) $V_{HH}$ Sequence Analysis

The impact of the C-terminal deviations on the polarity of a $V_{HH}$ was estimated with the Zimmerman polarity score plot. In short, amino acids in the $V_{HH}$ sequence were given a polarity index value based on the dipole moments of the side chains. These values were then plotted with Graphpad Prism.

d) Conjugation of 1B4M-DTPA and CHX-A"-DTPA to $V_{HH}$'s

A 10-fold molar excess of bifunctional chelator 1B4M-DTPA (for $^{177}$Lu) or CHX-A"-DTPA (for $^{111}$In) was conjugated for 3 h at RT to the free ε-amino-groups of lysines in the $V_{HH}$'s in 600 µl of 0.05 M sodium carbonate buffer (pH 8.5). The conjugation reaction was quenched by reducing the pH of the mixture to pH 7.0. $V_{HH}$-chelator was purified on Superdex 75 10/30 (GE Healthcare) in 0.1 M ammonium acetate buffer pH 7.0. The mean degree of conjugation was evaluated with ESI-Q-ToF-MS (Waters, Micromass), in positive mode.

e) Preparation of $^{111}$In— and $^{177}$Lu-DTPA-$V_{HH}$'s $V_{HH}$'s were labeled with $^{177}$Lu as previously described (20). Carrier-free $^{177}$Lu was obtained from ITG (Garching, Germany) as a chloride solution, with a specific activity of 3000 GBq/mg. Radiolabeling with $^{111}$In was performed similarly. $^{111}$InCl$_3$ was purchased from Mallinckrodt (Petten, The Netherlands) with a specific activity of 1850 GBq/mg.

The necessary amount of $^{177}$Lu/$^{111}$In was added to a test vial containing metal-free 0.1 M ammonium acetate buffer pH 5.0, to reach an end volume of 200 µL. Then, 25-100 µg of $V_{HH}$-DTPA (1 mg/mL) was added and incubated for 30 min at RT. The radiolabeled $V_{HH}$ solution was purified on a disposable Nap-5 gelfiltration column (GE Healthcare) and pushed through a 0.22 µm filter. Radiochemical purity was assessed using iTLC with 0.2 M citric acid as mobile phase, and with either analytical radio-HPLC or radio-SEC. Radio-HPLC was performed using a polystyrene divinylbenzene copolymer reversed-phase column (PLRP-S 300 Å, 5 µm, 250/4 mm, Agilent, Diegem, Belgium). Here, a mixture of 0.1% TFA in H$_2$O and ACN was used as eluent with the following gradient: 0-5 min 25% ACN; 5-7 min 25-34% ACN; 7-10 min 75-100% ACN; 10-25 min 100% ACN at a flow rate of 1 ml/min. Radio-SEC was done on Superdex 75 5/150GL using PBS as mobile phase at a flow rate of 0.3 mL/min.

Untagged $^{111}$In-DTPA-2Rs15d, used for dynamic planar scintigraphy studies, consisted of a $V_{HH}$:$^{111}$In ratio of 7:1. For the ex vivo biodistribution experiments with untagged $^{177}$Lu-DTPA-2Rs15d a ratio of 9:1 ($V_{HH}$:$^{177}$Lu) was achieved, while for targeted radionuclide therapy, samples of untagged $^{177}$Lu-DTPA-2Rs15d with a $V_{HH}$:$^{177}$Lu ratio of 3:1 were used.

f) Preparation of $^{177}$Lu-DTPA-Trastuzumab

Conjugation of 1B4M-DTPA to Trastuzumab was performed to yield a DTPA:Trastuzumab ratio of 5:1. Briefly, a 100-fold molar excess of bifunctional chelator 1B4M-DTPA was conjugated overnight at RT to the free ε-amino-groups of lysines in Trastuzumab (Herceptin®, Hoffman-La Roche, Missis-sauga, ON, USA) in 3500 it of 0.05 M sodium carbonate buffer (pH 8.5). The reaction was quenched by reducing the pH to 7.0. DTPA-Trastuzumab was purified on Superdex 75 10/30 (GE Healthcare) in 0.1 M ammonium acetate buffer pH 7.0. The degree of conjugation was evaluated with ESI-Q-ToF-MS (Waters, Micromass), in positive mode. The necessary amount of $^{177}$Lu was added to a test vial containing metal-free 0.1 M ammonium acetate buffer pH 5.0, to reach an end volume of 200 µL. Then, 100-250 µg DTPA-Trastuzumab (2.4 mg/mL) was added and incubated for 30 min at RT. $^{177}$Lu-DTPA-Trastuzumab was purified on a disposable Nap-5 gelfiltration column (GE Healthcare) and pushed through a 0.22 µm filter. Radiochemical purity was assessed using iTLC and radio-SEC, as described above.

q) Animal Studies

Healthy male Wistar rats (255±53 g body weight) were used in dynamic planar scintigraphy studies. Female athymic nude mice (20±5 g body weight) were inoculated with 8×10$^6$ SKOV3 cells in PBS, s.c. in the right hind leg, under 2.5% isoflurane anesthesia (Abbott, Ottignies-Louvain-la-Neuve, Belgium). Tumors reached a size of 205±68 mm$^3$, for biodistribution purposes. SKOV3-LUC xenografts were obtained by inoculating female athymic mice with 3×10$^6$ SKOV3-LUC cells in the right hind leg. Tumors were grown to reach 26±5 mm$^3$, for targeted radiotherapy purposes. The animal protocols were approved by the ethical committee of the Vrije Universiteit Brussel.

h) Kidney Retention of $^{111}$in-DTPA-$V_{HH}$'s in Healthy Wistar Rats

Wistar rats (n=3) were anesthetized by an i.p. injection of 250 µL pentobarbital, prior to an i.v. injection of $^{111}$In-DTPA-$V_{HH}$'s (35.8±5.4 MBq). In a separate group, the $^{111}$In-DTPA-untagged $V_{HH}$'s were additionally coinjected in parallel with 80 mg/kg Gelofusin (40 g/l, Braun Medical, Diegem, Belgium). To record the fast in vivo kinetics of radiolabeled $V_{HH}$'s, dynamic planar imaging was performed immediately after injection (100 frames of 30 s). Time activity curves of the kidneys were generated using AMIDE Medical Image Data Examiner software. ROIs were drawn around total body and kidneys, to calculate the radioactivity retained in kidneys relative to the total injected activity (% IA).

i) In Vivo Tumor Targeting of $^{177}$Lu-DTPA-$V_{HH}$'s

SKOV3 tumor-bearing mice (n=3) were injected i.v. with each of the $^{177}$Lu-DTPA-2Rs15d $V_{HH}$ formats (21.5±1.7 MBq). In a separate group, $^{177}$Lu-DTPA-untagged 2Rs15d was co-injected with 150 mg/kg Gelofusin. Mice were euthanized and dissected 1 h p.i., tissues were weighed and radioactivity was counted with an automated gamma counter (Cobra Inspector 5003, Canberra Packard, USA). The amount of radioactivity present in the different tissues was expressed as % IA/g tissue.

j) Comparative Dosimetry Calculation of a Single Dose $^{177}$Lu-DTPA-Untagged 2Rs15d and Gelofusin Versus $^{177}$Lu-DTPA-Trastuzumab SKOV3 tumor-bearing mice were injected i.v. with either 14.7±1.3 MBq $^{177}$Lu-DTPA-untagged 2Rs15d and 150 mg/kg Gelofusin, or 10.1±0.2 MBq $^{177}$Lu-DTPA-Trastuzumab. At 1, 3, 6, 24, 48, 72, and 120 h p.i., mice (n=3) were euthanized and dissected to count radioactivity as described above and to obtain tissue biodistribution values expressed as % IA/g. The time point 168 h p.i. was included for the dosimetric calculation of $^{177}$Lu-DTPA-Trastuzumab. These values were time integrated to obtain the residence time per gram tissue. Briefly, the integration between time 0 and 120 h (or 168 h for $^{177}$Lu-DTPA-Trastzuzmab) was made using the trapezoid method. The final 2 points were used to estimate the residence time from 120 h to infinity. For each data set, the absorbed doses were calculated. The S values of $^{177}$Lu were obtained from RADAR phantoms (www.doseinfo-radar.com/RADARphan.html). The S value for 1 g sphere (0.0233 mGy/MBq s) was used for dose calculations.

k) Experimental Targeted Radionuclide Therapy with $^{177}$Lu-DTPA-Untagged 2Rs15d and Gelofusin When SKOV3-LUC tumors reached a volume of 20-30 mm$^3$ (day 7), animals were randomly categorized into 3 groups (n=8). Mice in each group received 7 i.v. injections (once a week, over a period of 7 weeks) of a volume containing either 20.7±0.4 MBq $^{177}$Lu-DTPA-untagged 2Rs15d, 19.3±0.8 MBq $^{177}$Lu-DTPA-untagged BcII10, or PBS. All samples were diluted in 150 mg/kg Gelofusin. The study was terminated 125 days after tumor cell inoculation. Animal weights were monitored weekly, as well as tumor growth through caliper measurement. Once every 2 weeks, tumor burden was also visualized using bioluminescence imaging, after i.p. injection of 150 mg/kg Luciferin. Results were summarized in an event-free survival curve, with events defined as (1) mortality, (2)>20% weight loss, (3) ulcerating tumor tissue, or (4) a tumor volume exceeding 250 mm$^3$. At the end of the study, animals were euthanized, dissected and renal tissues were preserved.

l) Kidney Histopathology

Renal samples of $^{177}$Lu-dosed and control groups were fixed in formalin for 4 hours, dehydrated and embedded in paraffin. The paraffin sections (3 μm) were processed for staining with H&E, PAS and Masson's trichrome, according to standard protocols. Stained sections were evaluated for necrosis, apoptosis, inflammation and vascular changes in the renal tissue, using light microscopy.

m) Statistics

Statistically significant differences in biodistribution were analyzed with the two-tailed t-test, while the event-free survival between treated groups was analyzed using the log-rank test (P<0.05).

2. Results a) Conjugation of 1B4M-DTPA and CHX-A"-DTPA to $V_{HH}$'s

Figure 11A:
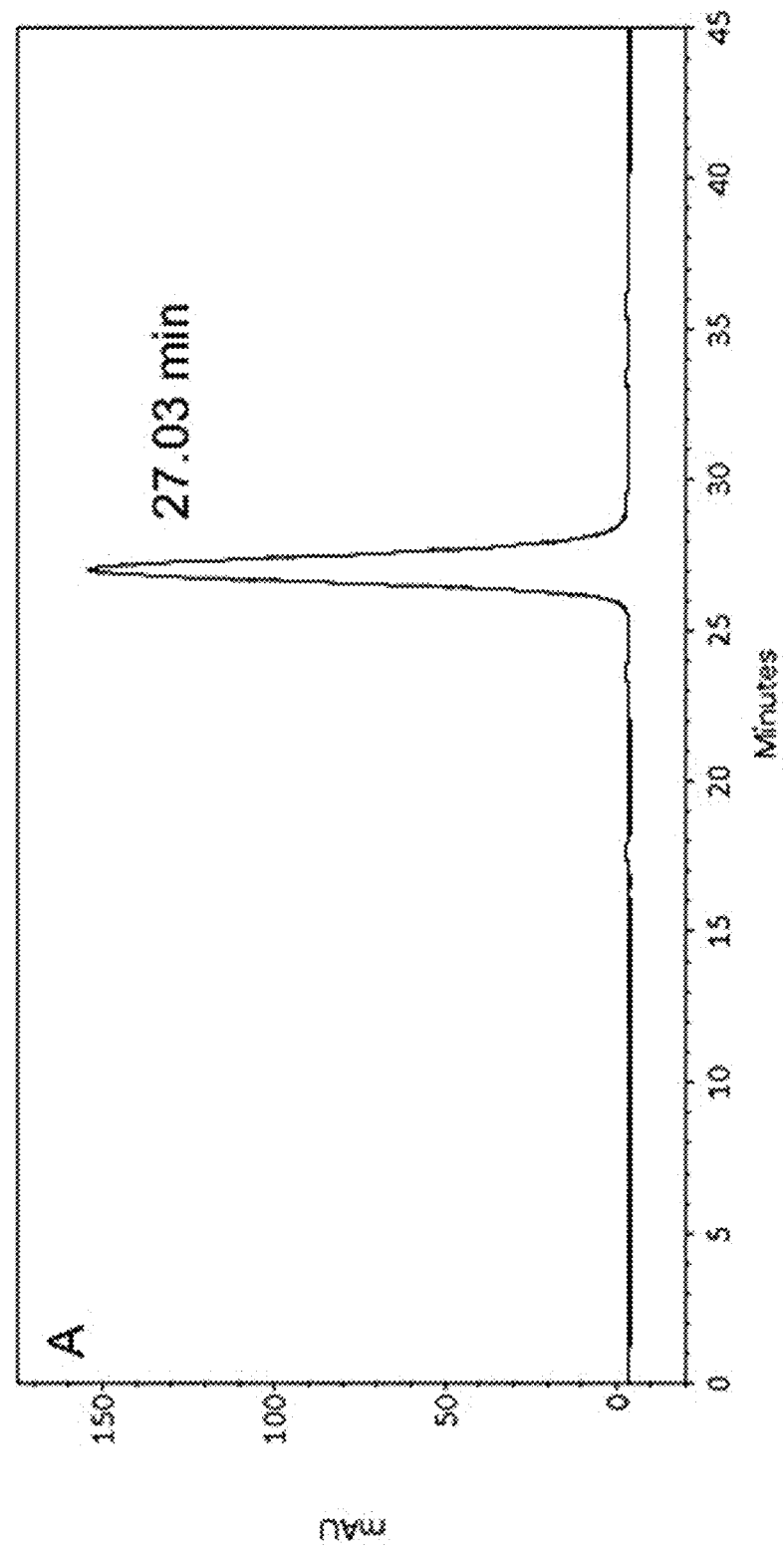
Figure 11B:
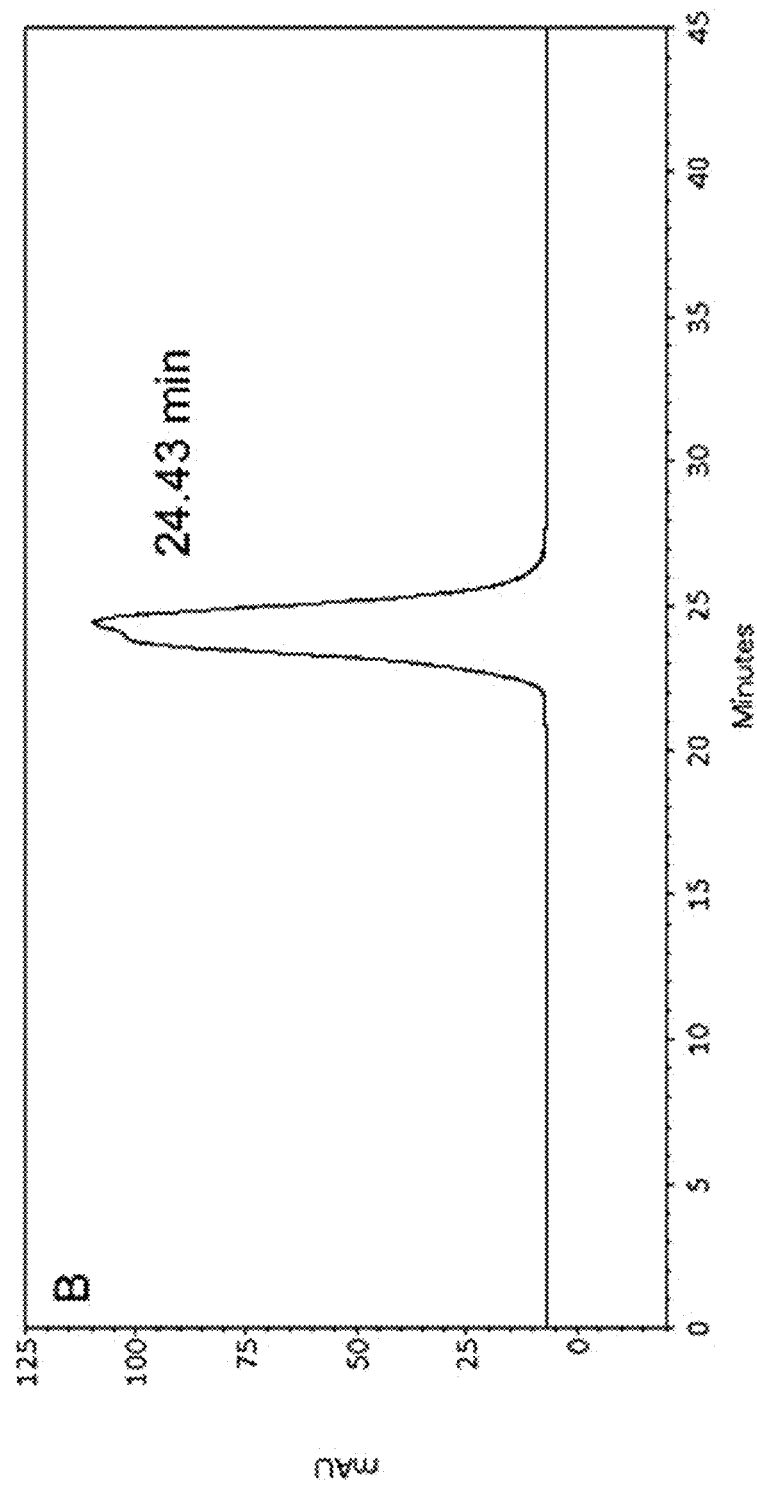
Figure 11C:
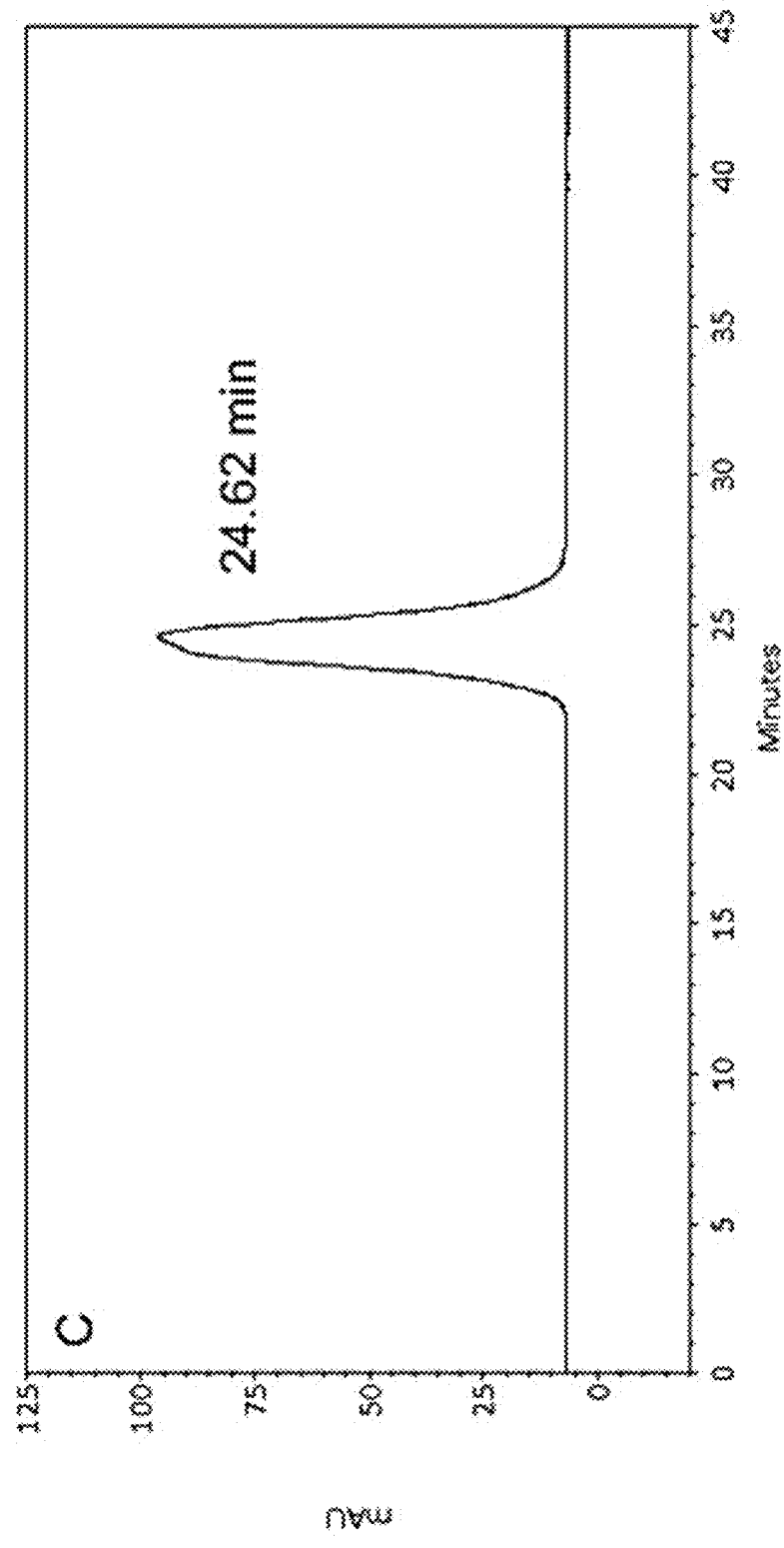
Figure 11D:
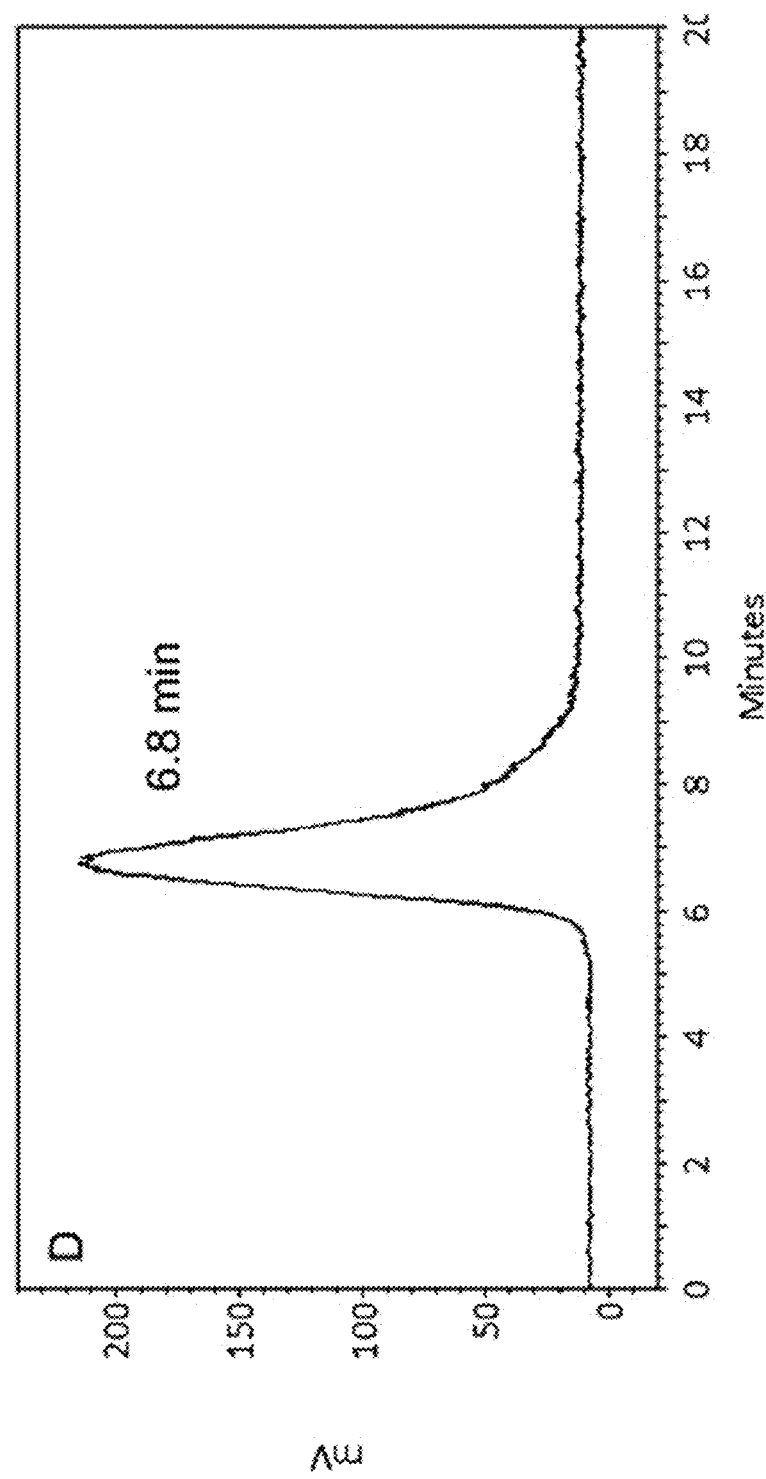
Figure 11E:
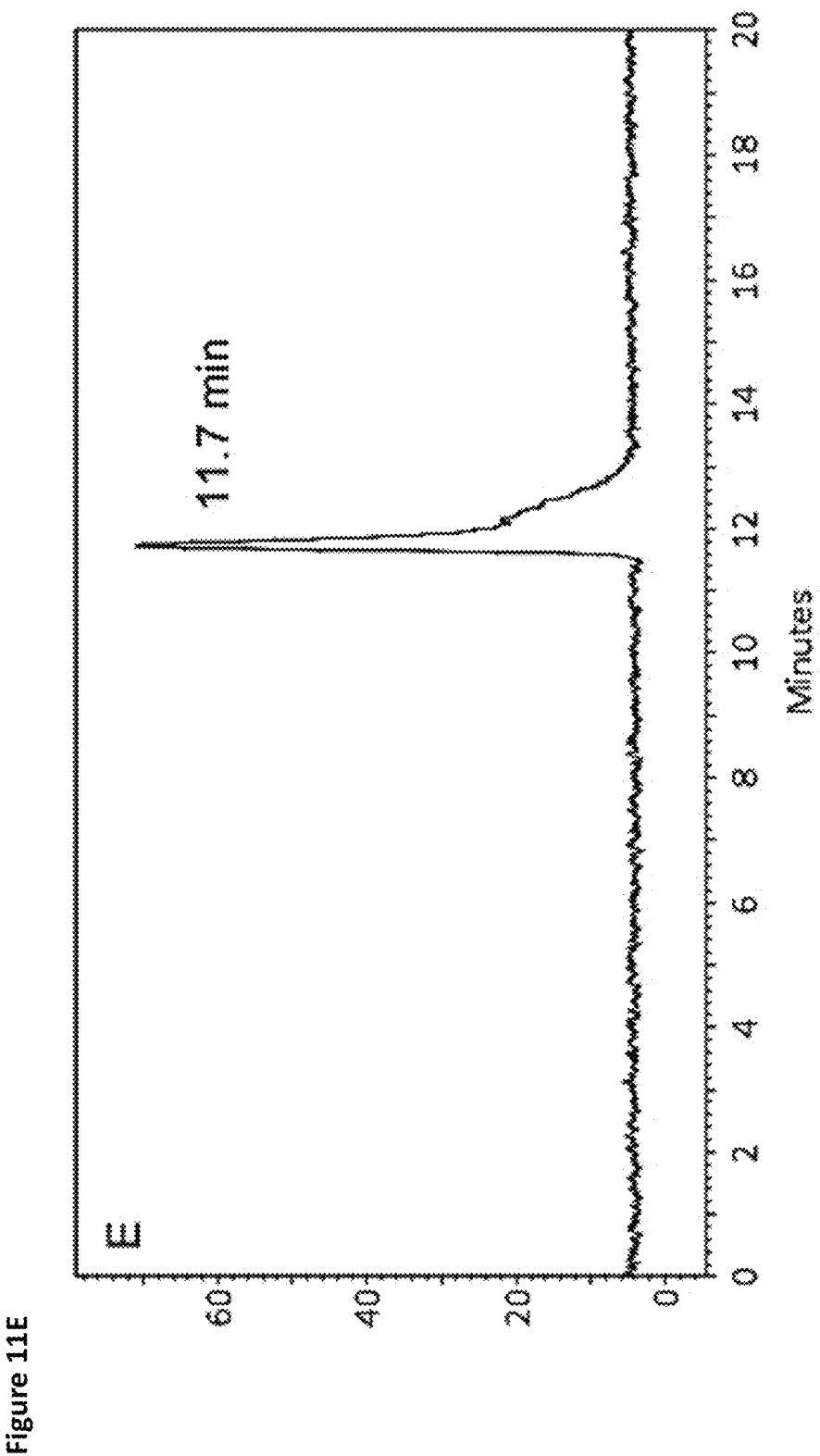

CHX-A"-DTPA was used for $^{111}$In labeling and 1B4M-DTPA for $^{177}$Lu labeling. SEC profiles and ESI-Q-ToF-MS analyses indicated successful conjugation of the bifunctional DTPA-chelators to the different $V_{HH}$ constructs. SEC profiles of untagged 2Rs15d, untagged 1B4M-DTPA-2Rs15d and untagged CHX-A"-DTPA-2Rs15d are presented in FIG. 11A-C. DTPA was conjugated to the ε-amino groups of lysine residues, hereby forming a thiourea bond. Therefore, since 2Rs15d contains multiple lysines, the conjugation reaction resulted in a mixture of molecules with 1, 2, and 3 DTPA chelators, as determined by ESI-Q-ToF-MS analysis. The MS profiles of untagged 2Rs15d (MW: 12624 Da), untagged CHX-A"-DTPA-2Rs15d (major peak corresponding to the conjugation of 2 DTPA, MW: 13923) and untagged 1B4M-DTPA-2Rs15d (major peak corresponding to the conjugation of 2 DTPA, MW: 13842) are shown in FIG. 16. Consequently, the dominant conjugation ratio (chelator:$V_{HH}$) for both 1B4M-DTPA and CHX-A"-DTPA to untagged 2Rs15d is 2:1. By applying the standardized protocol, a consistent degree of 2:1 (chelator: $V_{HH}$) conjugation was also obtained for the $V_{HH}$'s 2Rb17c and 1R136d.

b) Preparation of $^{111}$In— and $^{177}$Lu-DTPA-$V_{HH}$'s $V_{HH}$'s were conjugated with CHX-A"-DTPA for $^{111}$In labeling. After radiolabeling, iTLC revealed radiochemical purities of 95.1±1.7% and >99%, before and after SEC purification, respectively. The 2Rs15d $V_{HH}$ constructs conjugated with 1B4M-DTPA were labeled with $^{177}$Lu in high yields as determined by iTLC, i.e. 97.2±2.5% before and >99% after SEC purification. Radiochemical purities were confirmed with radio-HPLC or radio-SEC. The radio-HPLC profile of untagged $^{111}$In-DTPA-2Rs15d and the radio-SEC profile of untagged $^{177}$Lu-DTPA 2Rs15d are shown in FIG. 11D-E.

c) Preparation of $^{177}$Lu-DTPA-Trastuzumab

SEC profiles and ESI-Q-ToF-MS analyses indicated successful conjugation of 1B4M-DTPA to Trastuzumab. The radiochemical purity of $^{177}$Lu-DTPA-Trastuzumab was 99.5±0.2% (iTLC) and was confirmed with radio-SEC. SEC profiles of unconjugated Trastuzumab and DTPA-Trastuzumab are shown in FIG. 17, together with the radio-SEC profile of $^{177}$Lu-DTPA-Trastuzumab.

d) Kidney Retention of $^{111}$In-DTPA-$V_{HH}$'s in Healthy Wistar Rats

Figures 12A, 12B, 12C, 12D, 12E:
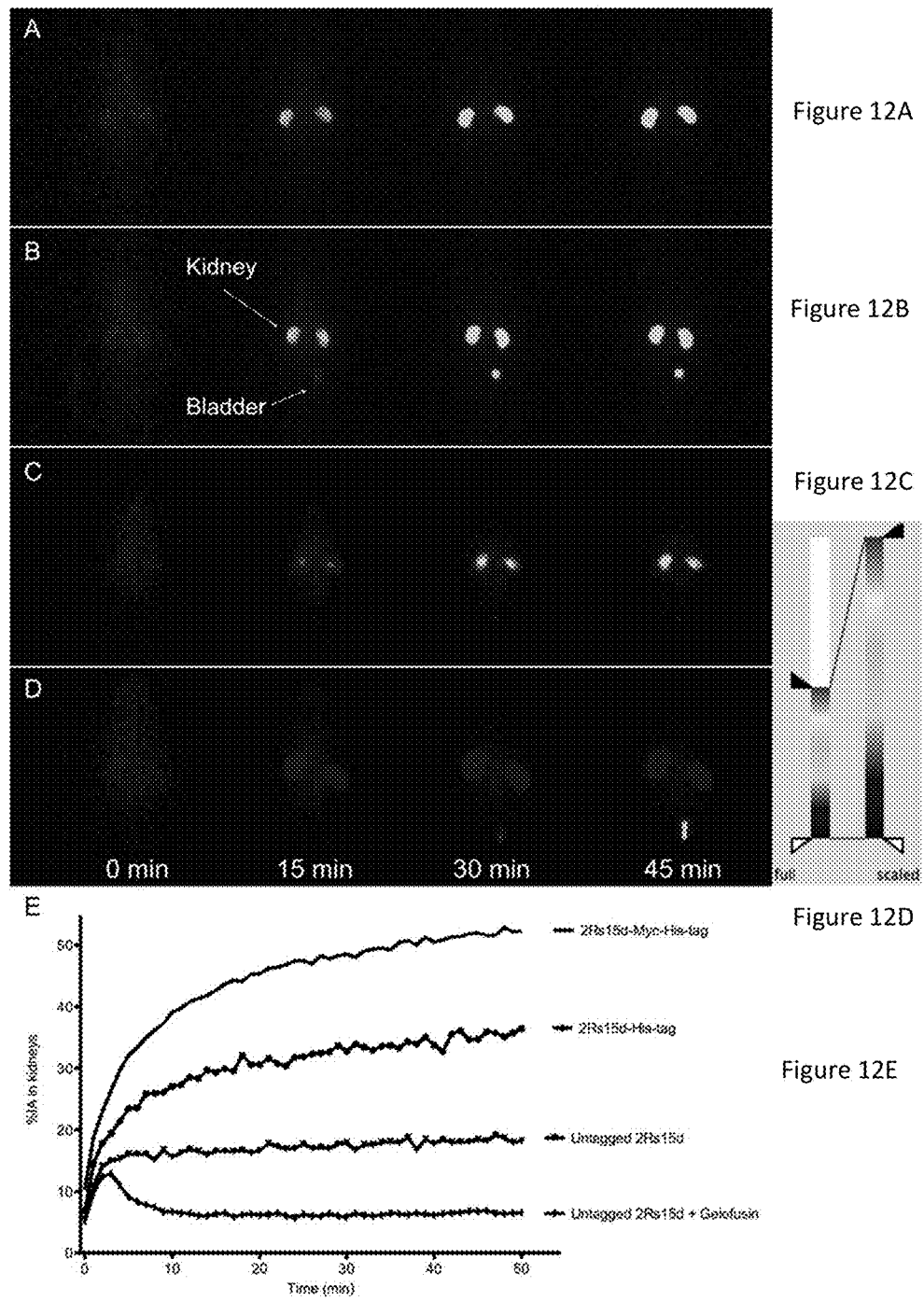

To confirm that the $V_{HH}$'s C-terminal polarity strongly influences the degree of kidney retention, Wistar rats were injected with the different $^{111}$In-DTPA-$V_{HH}$ constructs. Representative and equally scaled planar images are shown in FIG. 12A-D. Finally, whole-body and kidney ROIs were drawn and plotted as a function of time, to obtain the relative amounts of accumulating radioactivity in kidneys (FIG. 12E). Highest accumulation of radioactivity in the kidneys was confirmed for Myc-His-tagged 2Rs15d, followed by His-tagged and untagged 2Rs15d, giving values of 52.44±4.70, 36.45±4.28 and 18.24±1.71% IA at 50 min p.i., respectively. All three curves described a similar parabolic shape. The lowest accumulation in kidneys was observed for untagged 2Rs15d that was coinfused with 80 mg/kg Gelofusin, with a value of only 6.52±0.18% IA at 50 min p.i. Here the curve described an initial incline of radioactivity followed rapidly by a steady low amount of radioactivity in kidneys. These findings were confirmed for two additional HER2-targeting $V_{HH}$'s 2Rb17c and 1R136d (FIG. 18).

e) In Vivo Tumor Targeting of the $^{177}$Lu-DTPA-2Rs15d $V_{HH}$'s

SKOV3 tumor xenografted mice (n=3) were injected with the different $^{177}$Lu-DTPA-2Rs15d $V_{HH}$'s. Tumor targeting was not affected by altering the C-terminal tag or by a coinjection with gelofusin, with uptake values of 5.9±0.7%; 6.4±0.8%; 6.9±0.4% and 6.5±0.2% IA/g for Myc-His-tagged, His-tagged, untagged and untagged $V_{HH}$ with 150 mg/kg Gelofusin, respectively. More importantly, again substantial differences in kidney uptake were observed, with decreasing values of 195.8±23.7%; 127.7±2.9%; 25.8±1.3% and 10.4±1.7% IA/g for Myc-His-tagged, His-tagged, untagged, and untagged $V_{HH}$ together with 150 mg/kg Gelofusin, respectively (FIG. 13). Uptake values in the major organs and tissues did not differ significantly.

f) Comparative Dosimetry Calculation of a Single Dose $^{177}$Lu-DTPA-Untagged 2Rs15d and Gelofusin Versus $^{177}$Lu-DTPA-Trastuzumab For untagged $^{177}$Lu-DTPA-2Rs15d $V_{HH}$, the highest tumor uptake values were observed at early time points and decreased from 6.50±0.24% IA/g at 1 h p.i. to 2.15±0.11% IA/g at 48 h p.i. and to 1.15±0.16% IA/g at 120 h p.i. Kidney uptake values peaked at 10.36±1.73% IA/g 1 h p.i. and then decreased to 2.08±0.29% IA/g at 48 h p.i. and 0.40±0.29% IA/g at 120 h p.i. Bone activity was low, indicating there was no substantial release of $^{177}$Lu. Radioactivity concentration in the other major organs and tissues was low, with values below 0.5% IA/g at early time points, and decreasing over time. In contrast, tumor uptake of $^{177}$Lu-DTPA-Trastuzumab was low at early time points and increased from 1.07±0.31% IA/g to 28.09±0.58% IA/g at 96 h and 17.13±2.00% IA/g at 168 h p.i. Blood values were high with 23.32±4.36% IA/g at 1 h and still 10.69±1.77% IA/g at 168 h p.i. At all time points the radioactive concentrations in additional organs (especially in liver, lung and spleen) remained much higher than for untagged $^{177}$Lu-DTPA-2Rs15d.

For untagged $^{177}$Lu-labeled 2Rs15d, the highest radiation absorbed dose was delivered to tumor and kidneys, with an equivalent value of 0.9 Gy/MBq, while the radiation burden to other healthy tissues was very low. $^{177}$Lu-DTPA-Trastuzumab on the other hand delivered a calculated dose to the tumor of 5.55 Gy/MBq. However, radiation to blood, liver, spleen and lung was also high and estimated to be 4.18, 1.72, 1.60 and 1.55 Gy/MBq, respectively.

g) Experimental Targeted Radionuclide Therapy with $^{177}$Lu-DTPA-Untagged 2Rs15d and Gelofusin Mice bearing small SKOV3-LUC tumors were i.v. injected with either untagged $^{177}$Lu-DTPA-2Rs15d, untagged $^{177}$Lu-DTPA-BcII10 (a non-targeting control $V_{HH}$) or the vehicle PBS, all coinjected with 150 mg/kg Gelofusin. For both the PBS-treated (n=8) and $^{177}$Lu-DTPA-BcII10-treated animals (n=8), the tumor volume of all animals already exceeded the value of 250 mm$^3$ between day 33 and 75 after inoculation, as measured with a caliper (FIG. 14B). All animals from the control groups were euthanized at day 85 due to the development of large tumors (>1 cm$^3$), as shown in FIG. 14B. No statistically significant difference was observed in event-free survival between both control groups. In contrast, up to day 125 no substantial increase in tumor size was observed among the mice that were treated with untagged anti-HER2 $^{177}$Lu-DTPA-2Rs15d (n=8). Remarkably, 5 out of 8 mice were completely free of tumor burden, as confirmed by bioluminescence imaging (FIG. 14A). The other 3 mice developed small, LUC$^{pos}$, but no palpable tumors. One animal in this group had to be euthanized due to a weight loss of more than 20% (day 95). Overall, event-free survival was significantly longer for the treated group compared to the control groups that received PBS (P<0.0001) or $^{177}$Lu-DTPA-BcII10 (P<0.0001), respectively (FIG. 15A). Histopathological analyses of renal tissues showed no differences between the experimental groups. The glomeruli, the tubuli and the vasculature were morphologically normal and no necrosis was noted. The interstitium was not broadened or fibrotic, and was free of inflammatory cells. No protein casts could be observed (FIG. 15B).

3. Discussion

In this study we investigated the influence of the C-terminal amino acid tag on the overall polarity of the $V_{HH}$ sequence on the one hand, and the degree of kidney retention on the other. Amino-acid tags are regularly linked to proteins such as antibody-fragments, for purification and radiolabeling purposes (His-tag) or for in vitro detection (Myc-tag). However, the introduction of potentially charged amino acids will affect the overall polarity of the protein, and thus also its in vivo behavior. This presumption was eventually confirmed by evaluating the in vivo behavior of different $^{111}$In-DTPA-$V_{HH}$ formats in healthy Wistar rats. The highest activity retained in kidneys was observed for Myc-His-tagged 2Rs15d. Changing Myc-His-tag to His-tag led to a drop in retention of label by 31%, 50 min p.i. Complete removal of the C-terminal amino acid tag lowered kidney retention up to 65%, as compared to the Myc-His-tagged 2Rs15d. Finally, coinjecting untagged $^{111}$In-DTPA-2Rs15d with Gelofusin further reduced kidney retention with an additional 65%. This observation was confirmed with two other HER2-targeting $V_{HH}$'s.

A similar trend was observed after injecting the different 2Rs15d formats, radiolabeled with $^{177}$Lu, in HER2$^{pos}$ xenografted mice. FIG. 13 confirms the observations from the dynamic scans regarding the kidney retention. The highest uptake value in kidney was observed for the Myc-His-tagged format whereas the lowest uptake was attained with the untagged 2Rs15d and 150 mg/kg Gelofusin. Tumor targeting was not affected by either adjusting the C-terminal amino acid tag or coinjecting Gelofusin.

A comparative ex vivo biodistribution of a single dose untagged $^{177}$Lu-DTPA-2Rs15d with 150 mg/kg Gelofusin versus a single dose $^{177}$Lu-DTPA-Trastuzumab was evaluated until 120 h and 168 h p.i., respectively. Injecting untagged $^{177}$Lu-DTPA-2Rs15d $V_{HH}$ revealed a fast washout of activity from all non-target organs and tissues. At 48 h p.i., the radioactivity in tumor exceeded the amount present in kidney, resulting in a comparable radiation absorbed dose to tumor and kidneys. The dose delivered to non-targeted tissues like blood, liver, and spleen were extremely low. Moreover, the low dose delivered to bone suggests the absence of free $^{177}$Lu. In contrast, although $^{177}$Lu-DTPA-Trastuzumab supplied a 6 fold higher dose to the tumor than untagged $^{177}$Lu-DTPA-2Rs15d, also the radiation burden to lung, liver, spleen, bone and blood was concomitantly 155, 34, 80, 26 and 4180 fold higher.

Finally, $V_{HH}$-based targeted radionuclide therapy was performed in HER2$^{pos}$ xenografted mice with small tumor volumes of 20-30 mm$^3$, as a preliminary model to mimic minimal residual or micrometastatic disease. Both experimental groups receiving either non-specific $^{177}$Lu-labeled BcII10 $V_{HH}$ or the vehicle PBS group noted no significant differences in terms of tumor growth inhibition. Tumor volumes of all animals in both control groups exceeded already the value of 250 mm$^3$ between day 33 and 75 after inoculation. No animals in the treated group had tumors exceeding 250 mm$^3$ up to day 125. Moreover, 5 out of the 8 treated mice showed complete absence of tumor formation. The other 3 mice developed small, but no palpable tumors, that were however detectable via bioluminescence imaging.

Taken together, the results presented here show a successful application of $V_{HH}$-based targeted radionuclide therapy in tumor-bearing mice, using the therapeutic radionuclide Lutetium-177. Since highly specific $V_{HH}$'s are easily raised against a variety of cancer-related antigens, $V_{HH}$-based targeted radionuclide therapy could be introduced in several types of cancer disease.

4. Conclusion

We have demonstrated that kidney retention is reduced significantly when using untagged $V_{HH}$'s and coinfusion with 150 mg/kg Gelofusin. Hence, anti-HER2 $V_{HH}$'s constitute potent small molecular vehicles for targeted radionuclide therapy. Anti-HER2 $V_{HH}$'s, when radiolabeled with $^{177}$Lu, efficiently inhibit growth of HER2 expressing tumors in xenografted mice, without pronounced non-specific radia-

Example 5

Blood-Clearance of Monovalent, Non-Lifetime Extended, Untagged, [$^{131}$I]SGMIB-Labeled Anti-HER2 $V_{HH}$ 2Rs15d in C57bl/6 Mice Materials & Methods Six normal male C57bl/6 mice were used to assess blood clearance. Each animal received an intravenous injection of 2500 kBq untagged monovalent [$^{131}$I]SGMIB-labeled anti-HER2 VHH 2Rs15d (approximately 4 µg). Blood samples were collected with a microcapillary at 2, 5, 10, 15, 20, 40, 60 and 120 and 180 min post injection Results were expressed in percentage of injected activity per total blood volume (% IA/TBV). The total blood volume was estimated as 7% of the total body weight. The blood half-life was determined through a biphasic nonlinear regression fit using GraphPad Prism.

Results

Untagged monovalent [$^{131}$I]SGMIB-labeled anti-HER2 VHH 2Rs15d was cleared following a biphasic blood curve (FIG. 19). The calculated half-life for the initial fast washout phase was about 1.93 min. After 60 min, less than 2% IA/TBV (percentage of injected activity per total blood volume) was measured in blood.

Example 6

Biodistribution and Dosimetry of Monovalent, Non-Lifetime Extended, Untapped, [$^{131}$I]SGMIB-Labeled Anti-HER2 VHH 2Rs15d in HER2+Tumor Xenoqrafted Mice, and Radiation Dose Estimates in Adult Female Human Materials & Methods Female six weeks old CRL:Nu-FoxNlnu athymic mice were implanted with 60-day continuous release 17-β-estradiol pellets (0.72 mg, Innovative Research of America: Sarasota, Fla., USA) on their back one day prior to tumor implantation. HER2+BT474/M1 human breast cancer cells (10×10$^6$) in 50% Matrigel (BD Biosciences, Bedford, Mass., USA) were injected subcutaneously into the right flank and grown until they reached a volume of 250-350 mm$^3$.

The biodistribution profile of untagged monovalent [$^{131}$I]SGMIB-labeled anti-HER2 VHH 2Rs15d was determined. The animals (n=3) were injected with 1185 kBq of untagged monovalent [$^{131}$I]SGMIB-labeled anti-HER2 VHH 2Rs15d (2.0 µg). At 1, 3, 6, 24, 48, 72, 96, 120, 144 h after injection, the mice were euthanized by halothane overdose, dissected, and their organs collected. Tissues of interest were weighed and counted in a γ-counter for $^{131}$I radioactivity along with injection standards (Table 7). The obtained data (expressed as % IA/g) were used to calculate the corresponding tumor to healthy tissue ratios (Table 8)

In addition, the biodistribution values of untagged monovalent $^{131}$I-SGMIB-anti-HER2 VHH 2Rs15d were used for dosimetric calculations (Table 9). The values were time integrated to obtain the residence time per gram tissue. Briefly, the integration between time 0 and 144 h was made using the trapezoid method. Next, the absorbed doses were calculated. In the absorbed dose calculations, S values for $^{131}$I were obtained from RADAR phantoms (Unit Density Spheres) published on the internet. The S value for a 1 g sphere (0,0000304 Gy.Kg/MBq.s) was used generally to calculate all organ doses. This simplified dosimetry calculation is motivated by the fact that the low-energy β-particles in the $^{131}$I decay are locally absorbed, and photons and other penetrating radiations are contributing to a low extent, which means that the cross-talk between different organs in the mouse is negligible.

An estimation of organ-absorbed doses in adult female humans was performed by extrapolation of the biodistribution data of untagged monovalent [$^{131}$I]SGMIB-labeled anti-HER2 VHH 2Rs15d at different time points in mice to the adult female phantom using OLINDA software, using a voiding bladder interval of 1 h (Table 10). The calculations were based on time-activity curves to determine the number of disintegrations in organs. Organ doses and effective dose were calculated using the appropriate weighting factors for the various organs.

Results

Extremely high tumor to healthy tissue ratios were achieved (Table 8), highlighting the very low uptake in healthy tissues and thus the low toxicity. Tumor to tissue ratios of this extent as observed using the untagged monovalent [$^{131}$I]SGMIB-labeled anti-HER2 VHH 2Rs15d have never been published for other radioimmunobiologicals so far. In particular, these ratios were significantly higher compared to the HER2-targeting cystein-tagged VHH termed 5F7GGC (Pruszynski et al., 2014; J. Nucl. Med. 55(4):650-656). Tumor to lungs, heart, liver, kidney, stomach, spleen, muscle and blood ratios were all significantly higher at time points 1 and 24 h for untagged monovalent [$^{131}$I]SGMIB-labeled anti-HER2 VHH 2Rs15d versus 5F7GGC VHH. It was especially surprising to detect the very low uptake value in the kidneys for the untagged monovalent [$^{131}$I]SGMIB-labeled anti-HER2 VHH 2Rs15d. This kidney uptake value was even lower than what had been reported for 5F7GGC VHH.

TABLE 7

After injection of the untagged monovalent [$^{131}$I]SGMIB-labeled anti-HER2 VHH 2Rs15d, 21 different tissues of interest are counted for $^{131}$I activity in an automated gamma counter. Uptake values are expressed as % injected Activity/gram tissue (% IA/g), except for thyroid, adrenals and gallbladder for which % IA is used. Values represent an average (n = 3) ± SD.

| Organ/tissue | 1 H MEAN | 1 H SD | 3 H MEAN | 3 H SD | 6 H MEAN | 6 H SD | 24 H MEAN | 24 H SD | 48 H MEAN | 48 H SD |
|---|---|---|---|---|---|---|---|---|---|---|
| Brain | 0.08 | 0.08 | 0.49 | 0.44 | 0.01 | 0.003 | 0.002 | 0.001 | 0.0004 | 0.0001 |
| Lungs | 0.94 | 0.17 | 0.30 | 0.11 | 0.19 | 0.04 | 0.05 | 0.02 | 0.02 | 0.01 |
| Heart | 0.43 | 0.07 | 0.15 | 0.02 | 0.08 | 0.004 | 0.02 | 0.001 | 0.01 | 0.003 |
| Liver | 1.05 | 0.18 | 0.39 | 0.12 | 0.24 | 0.09 | 0.04 | 0.01 | 0.05 | 0.003 |
| Kidneys | 55.63 | 8.47 | 12.5 | 2.73 | 7.15 | 1.95 | 0.94 | 0.52 | 0.52 | 0.13 |
| Stomach | 0.94 | 0.39 | 0.71 | 0.76 | 0.12 | 0.06 | 0.01 | 0.04 | 0.01 | 0.004 |

TABLE 7-continued

After injection of the untagged monovalent [$^{131}$I]SGMIB-labeled anti-HER2 VHH 2Rs15d, 21 different tissues of interest are counted for $^{131}$I activity in an automated gamma counter. Uptake values are expressed as % injected Activity/gram tissue (% IA/g), except for thyroid, adrenals and gallbladder for which % IA is used. Values represent an average (n = 3) ± SD.

| | | | | | | | | | | |
|---|---|---|---|---|---|---|---|---|---|---|
| Pancreas | 0.18 | 0.04 | 0.05 | 0.01 | 0.02 | 0.005 | 0.01 | 0.002 | 0.003 | 0.001 |
| Spleen | 0.39 | 0.07 | 0.21 | 0.02 | 0.09 | 0.04 | 0.02 | 0.004 | 0.01 | 0.002 |
| Skin | 0.86 | 0.26 | 0.43 | 0.11 | 0.31 | 0.11 | 0.02 | 0.005 | 0.01 | 0.007 |
| Muscle | 0.62 | 0.15 | 0.24 | 0.15 | 0.08 | 0.01 | 0.01 | 0.01 | 0.004 | 0.002 |
| Bone | 1 | 0.08 | 0.53 | 0.30 | 0.28 | 0.2 | 0.04 | 0.01 | 0.02 | 0.01 |
| S. intestines | 0.37 | 0.09 | 0.58 | 0.58 | 0.16 | 0.01 | 0.01 | 0.003 | 0.004 | 0.001 |
| L. intestines | 0.3 | 0.12 | 0.36 | 0.34 | 0.1 | 0.02 | 0.01 | 0.01 | 0.004 | 0.002 |
| Lymphnodes | 0.44 | 0.15 | 0.19 | 0.03 | 0.1 | 0.02 | 0.02 | 0.01 | 0.01 | 0.003 |
| Blood | 0.83 | 0.02 | 0.19 | 0.06 | 0.07 | 0.01 | 0.02 | 0.002 | 0.01 | 0.003 |
| Uterus | 1.1 | 0.21 | 0.02 | 0.005 | 0.34 | 0.38 | 0.02 | 0.003 | 0.01 | 0.002 |
| Thyroid* | 0.01 | 0.002 | 0.001 | 0.001 | 0.001 | 0.0002 | 0.0001 | 0.00005 | 0.0001 | 0.00011 |
| Adenals* | 0.02 | 0.02 | 0.002 | 0.001 | 0.001 | 0.0001 | 0.0001 | 0.0001 | 0.0001 | 0.0001 |
| Galbladder* | 0.01 | 0.004 | 0.003 | 0.002 | 0.001 | 0.001 | 0.0002 | 0.00002 | 0.0001 | 0.00011 |
| Tumor | 20.22 | 1.64 | 17.77 | 1.87 | 7.16 | 1.18 | 5.1 | 1.9 | 1.16 | 0.16 |
| Bladder | 6.65 | 5.57 | 2.43 | 1.38 | 1.18 | 1.4 | 0.03 | 0.01 | 0.02 | 0.005 |

| | 72 H | | 96 H | | 120 H | | 144 H | |
|---|---|---|---|---|---|---|---|---|
| Organ/tissue | MEAN | SD | MEAN | SD | MEAN | SD | MEAN | SD |
| Brain | 0.0014 | 0.0005 | 0.0003 | 0.0004 | 0.0008 | 0.0007 | 0.01 | 0.02 |
| Lungs | 0.0089 | 0.0024 | 0.02 | 0.01 | 0.01 | 0.003 | 0.03 | 0.02 |
| Heart | 0.0058 | 0.0009 | 0.01 | 0.002 | 0.004 | 0.0003 | 0.003 | 0.002 |
| Liver | 0.0112 | 0.0023 | 0.02 | 0.01 | 0.01 | 0.003 | 0.02 | 0.01 |
| Kidneys | 0.2413 | 0.1426 | 0.13 | 0.06 | 0.09 | 0.02 | 0.1 | 0.02 |
| Stomach | 0.0083 | 0.0016 | 0.01 | 0.01 | 0.004 | 0.0005 | 0.004 | 0.002 |
| Pancreas | 0.0014 | 0.0012 | 0.002 | 0.001 | 0.001 | 0.001 | 0.002 | 0.002 |
| Spleen | 0.005 | 0.0008 | 0.01 | 0.002 | 0.01 | 0.001 | 0.01 | 0.005 |
| Skin | 0.0181 | 0.0073 | 0.01 | 0.002 | 0.01 | 0.003 | 0.01 | 0.004 |
| Muscle | 0.002 | 0.0009 | 0.002 | 0.002 | 0.003 | 0.001 | 0.004 | 0.003 |
| Bone | 0.0159 | 0.0105 | 0.02 | 0.01 | 0.01 | 0.01 | 0.05 | 0.04 |
| S. intestines | 0.0078 | 0.0073 | 0.003 | 0.001 | 0.002 | 0.001 | 0.01 | 0.01 |
| L. intestines | 0.0071 | 0.0039 | 0.02 | 0.03 | 0.002 | 0.001 | 0.01 | 0.01 |
| Lymphnodes | 0.0086 | 0.0046 | 0.004 | 0.003 | 0.004 | 0.002 | 0.02 | 0.01 |
| Blood | 0.0098 | 0.0017 | 0.01 | 0.001 | 0.01 | 0.0003 | 0.01 | 0.001 |
| Uterus | 0.0063 | 0.002 | 0.01 | 0.002 | 0.004 | 0.001 | 0.003 | 0.002 |
| Thyroid* | 0.00001 | 0.00002 | 0.0001 | 0.0001 | 0.0001 | 0.0001 | 0.0001 | 0.00004 |
| Adenals* | 0.00011 | 0.00005 | 0.0001 | 0.0001 | 0.00003 | 0.00004 | 0.0001 | 0.0002 |
| Galbladder* | 0.0001 | 0.0001 | 0.00001 | 0.00001 | 0.00007 | 0.00006 | 0.0002 | 0.0003 |
| Tumor | 0.3952 | 0.0531 | 0.14 | 0.01 | 0.11 | 0.03 | 0.01 | 0.01 |
| Bladder | 0.0185 | 0.0074 | 0.01 | 0.01 | 0.01 | 0.002 | 0.01 | 0.01 |

TABLE 8

Calculated tumor to healthy tissue ratios. Values represent an average (n = 3) ± SD.

| Tumor to tissue | 1 H | | 3 H | | 6 H | | 24 H | | 48 H | |
|---|---|---|---|---|---|---|---|---|---|---|
| | MEAN | SD | MEAN | SD | MEAN | SD | MEAN | SD | MEAN | SD |
| T/Brain | 435.35 | 278.36 | 57.59 | 36.68 | 830.65 | 351.38 | 3573.01 | 1848.90 | 2967.91 | 741.27 |
| T/Lungs | 21.95 | 3.96 | 63.55 | 18.44 | 38.24 | 13.02 | 95.01 | 12.86 | 99.92 | 58.70 |
| T/Heart | 47.37 | 4.31 | 122.36 | 10.13 | 93.48 | 10.06 | 332.65 | 129.69 | 121.73 | 15.44 |
| T/Liver | 19.76 | 3.95 | 49.12 | 16.93 | 31.71 | 10.07 | 139.18 | 44.97 | 23.76 | 2.96 |
| T/Kidney | 0.34 | 0.06 | 1.47 | 0.39 | 1.06 | 0.38 | 6.48 | 4.45 | 2.28 | 0.44 |
| T/Stomach | 24.73 | 11.98 | 47.70 | 32.92 | 68.30 | 26.79 | 434.72 | 203.18 | 203.02 | 135.91 |
| T/Pancreas | 112.78 | 20.65 | 398.68 | 103.12 | 380.57 | 31.62 | 1129.96 | 577.80 | 467.06 | 189.90 |
| T/Spleen | 53.66 | 14.59 | 85.43 | 7.36 | 103.47 | 80.11 | 336.61 | 172.00 | 107.51 | 23.59 |
| T/Skin | 25.42 | 9.73 | 42.48 | 8.31 | 23.89 | 4.70 | 232.89 | 43.89 | 98.33 | 46.17 |
| T/Muscle | 34.56 | 12.32 | 112.45 | 95.38 | 91.22 | 2.19 | 499.42 | 249.18 | 383.10 | 233.29 |
| T/Bone | 20.30 | 2.80 | 41.83 | 23.00 | 31.98 | 13.43 | 121.67 | 46.99 | 78.78 | 41.41 |
| T/Small intestine | 56.73 | 11.52 | 57.89 | 45.42 | 46.28 | 11.40 | 1107.06 | 986.14 | 281.88 | 104.41 |
| T/Large intestine | 74.99 | 28.66 | 76.35 | 45.49 | 72.43 | 11.17 | 819.79 | 591.78 | 365.73 | 165.39 |
| T/Lymphnodes | 49.66 | 17.83 | 97.34 | 22.84 | 75.39 | 20.89 | 376.44 | 298.04 | 146.48 | 55.22 |
| T/Blood | 24.35 | 1.39 | 96.84 | 20.56 | 107.23 | 29.37 | 258.66 | 93.60 | 86.21 | 22.81 |
| T/Uterus | 18.77 | 3.29 | 773.99 | 150.39 | 43.43 | 29.74 | 260.55 | 53.85 | 107.01 | 21.00 |

TABLE 8-continued

Calculated tumor to healthy tissue ratios. Values represent an average (n = 3) ± SD.

| Tumor to tissue | 72 H MEAN | SD | 96 H MEAN | SD | 120 H MEAN | SD | 144 H MEAN | SD |
|---|---|---|---|---|---|---|---|---|
| T/Brain | 305.22 | 69.97 | 1777.55 | 1503.79 | 800.14 | 1246.53 | 127.20 | 218.68 |
| T/Lungs | 46.84 | 13.85 | 14.05 | 8.15 | 23.92 | 19.31 | 1.38 | 1.94 |
| T/Heart | 70.57 | 20.95 | 29.61 | 10.39 | 27.94 | 5.13 | 6.29 | 6.49 |
| T/Liver | 36.22 | 9.22 | 7.53 | 3.27 | 13.19 | 6.27 | 1.14 | 0.68 |
| T/Kidney | 1.46 | 0.14 | 1.17 | 0.40 | 1.13 | 0.12 | 0.15 | 0.06 |
| T/Stomach | 48.35 | 5.77 | 20.07 | 9.04 | 27.86 | 7.02 | 3.95 | 2.21 |
| T/Pancreas | 401.81 | 238.60 | 99.27 | 41.36 | 122.83 | 49.57 | 208.69 | 347.90 |
| T/Spleen | 82.13 | 25.18 | 22.91 | 9.53 | 18.67 | 3.30 | 5.25 | 6.42 |
| T/Skin | 26.37 | 17.02 | 16.51 | 4.28 | 12.58 | 4.83 | 1.30 | 0.59 |
| T/Muscle | 209.72 | 55.17 | 397.50 | 619.22 | 37.80 | 7.76 | 11.12 | 15.97 |
| T/Bone | 34.05 | 23.93 | 8.63 | 2.38 | 9.68 | 6.90 | 1.25 | 1.91 |
| T/Small intestine | 85.01 | 55.60 | 56.79 | 27.42 | 54.00 | 18.94 | 6.88 | 9.13 |
| T/Large intestine | 70.39 | 41.52 | 19.75 | 14.92 | 92.04 | 60.83 | 4.41 | 4.81 |
| T/Lymphnodes | 54.48 | 23.58 | 216.58 | 326.69 | 28.43 | 7.59 | 0.97 | 0.32 |
| T/Blood | 41.65 | 12.01 | 17.69 | 0.40 | 16.53 | 4.75 | 2.78 | 0.87 |
| T/Uterus | 65.95 | 18.96 | 25.56 | 4.91 | 30.62 | 11.81 | 5.22 | 2.58 |

Using the same method as described in Pruszynski et al. for calculating radiation absorbed doses to the kidneys and based on the % IA/g tissue values (Table 7) a value of 835.96 cGy/mCi was obtained for untagged monovalent [$^{131}$I]SGMIB-labeled anti-HER2 VHH 2Rs15d (Table 9), which was less than half the value obtained for 5F7GGC VHH, based on dosimetry data from Pruszynski et al. Also much lower values were observed to liver, spleen, lungs, stomach and blood for untagged monovalent [$^{131}$I]SGMIB-labeled anti-HER2 VHH 2Rs15d.

The obtained value for untagged monovalent [$^{131}$I]SGMIB-labeled anti-HER2 VHH 2Rs15d (835.96 cGy/mCi) was surprisingly lower than the absorbed dose to kidneys for the his-tagged monovalent [$^{131}$I]SGMIB-labeled anti-HER2 VHH 2Rs15d (1055 cGy/mCi, see Example 2).

TABLE 9

Dosimetry calculations for untagged monovalent [$^{131}$I]SGMIB-labeled anti-HER2 VHH 2Rs15d in female HER2$^+$ tumor xenografted mice.

| Organ/tissue | Dose (cGy/mCi) |
|---|---|
| Brain | 9.38 |
| Lungs | 26.66 |
| Heart | 11.50 |
| Liver | 31.13 |
| Kidneys | 835.96 |
| Stomach | 24.94 |
| Pancreas | 3.75 |
| Spleen | 13.22 |
| Skin | 28.38 |
| Muscle | 11.37 |
| Bone | 32.24 |
| S intestines | 20.79 |
| L intestines | 15.79 |
| Lymphnodes | 13.11 |
| Blood | 14.72 |
| Galbladder | 0.18 |
| Tumor | 1188.34 |
| Urinary Bladder | 119.53 |

Radiation dose estimates for adult females were calculated from the biodistribution data of untagged monovalent [$^{131}$I]SGMIB-labeled anti-HER2 VHH 2Rs15d in mice using OLINDA 1.0 software. The calculations were based on time-activity curves to determine the number of disintegrations in 20 source organs. Organ doses, effective dose, and effective dose equivalent were calculated using the appropriate weighting factors for the various organs. Table 10 summarizes the calculated organ-absorbed doses. The effective dose was estimated at 0.0273 mSv/MBq.

TABLE 10

Radiation dose estimates to different organs for adult female human based on OLINDA calculations.

| Target organ | Total (mSv/MBq) |
|---|---|
| Adrenals | 2.17E−04 |
| Brain | 7.27E−07 |
| Breasts | 5.84E−05 |
| Gallbladder wall | 7.33E−04 |
| Lower large intestine Wall | 7.99E−03 |
| Small Intestine | 3.17E−03 |
| Stomach wall | 3.52E−04 |
| Upper large intestine wall | 2.45E−03 |
| Heart wall | 7.12E−05 |
| Kidneys | 4.43E−04 |
| Liver | 2.62E−04 |
| Lungs | 6.49E−05 |
| Muscle | 1.83E−03 |
| Ovaries | 7.45E−03 |
| Pancreas | 2.66E−04 |
| Red Marrow | 1.27E−03 |
| Osteogenic cells | 8.93E−04 |
| Skin | 6.16E−04 |
| Spleen | 2.63E−04 |
| Thymus | 3.93E−05 |
| Thyroid | 8.87E−06 |
| Urinary bladder wall | 4.91E−01 |
| Uterus | 1.58E−02 |
| Total Body | 1.86E−03 |
| Effective dose Equivalent | 3.33E−02 |
| Effective dose | 2.73E−02 |

Example 7

Biodistribution of Untapped Monovalent [$^{131}$I]SGMIB-Labeled Anti-HER2 VHH 2Rs15d, in Competition with Trastuzumab and/or Pertuzumab in HER2$^+$ Tumor Xenografted Mice The biodistribution profile of untagged monovalent [$^{131}$I] SGMIB-labeled anti-HER2 VHH 2Rs15d was evaluated in HER2+ tumor xenografted mice, after pretreatment with Trastuzumab, pertuzumab, or a combination of both. Trastuzumab (trade names: Herclon®, Herceptin®) and pertuzumab (Trade name: Perjeta®) are monoclonal antibodies that interfere with the HER2/neu receptor. Their main use is to treat certain breast cancers.

Materials and Methods

Female six weeks old CRL:Nu-FoxNlnu athymic mice were implanted with 60-day continuous release 17-β-estradiol pellets (0.72 mg, Innovative Research of America: Sarasota, Fla., USA) on their back one day prior to tumor implantation. HER2+ BT474/M1 human breast cancer cells (5×10⁶) in 50% Matrigel (BD Biosciences, Bedford, Mass., USA) were injected subcutaneously into the right flank and grown until they reached a volume of 150-250 mm³. 72 h prior to untagged monovalent [$^{131}$I]SGMIB-labeled anti-HER2 VHH 2Rs15d administration, animals (n=3) were pretreated with a 100 molar excess of anti-HER2 mAbs. Next, they received 1185 kBq of untagged monovalent [$^{131}$I]SGMIB-labeled anti-HER2 VHH 2Rs15d (5.0 μg). 1 h after injection, the mice were euthanized by halothane overdose, dissected, and their organs collected. Tissues of interest were weighed and counted in a γ-counter for $^{131}$I radioactivity along with injection standards. Results were expressed as percentage injected activity per gram of tissue (% IA/g).

Results

The results are shown in Table 11. No significant difference in tumor uptake was observed between the animal group that only received untagged monovalent [$^{131}$I]SGMIB-labeled anti-HER2 VHH 2Rs15d, and the animal groups that received a pretreatment of Herceptin® and/or Perjeta®.

Thus, in some embodiments, the untagged monovalent [$^{131}$I]SGMIB-labeled anti-HER2 VHH 2Rs15d or functional fragments thereof according to the present disclosure do not compete with the monoclonal antibodies Herceptin® and Perjeta® for binding to HER2, as shown by the presented in vivo competition assay.

Example 8

Therapeutic Efficacy of Untapped Monovalent [$^{131}$I]SGMIB-Labeled Anti-HER2 VHH 2Rs15d in HER2+ Tumor Xenoqrafted Mice The therapeutic efficacy of untagged monovalent [$^{131}$I] SGMIB-labeled anti-HER2 VHH 2Rs15d was assessed by measuring its capacity to inhibit tumor growth in HER2+ tumor xenografted mice. The specificity of its therapeutic efficacy was evaluated by including 2 controls; (1) administration of an untagged monovalent [$^{131}$I]SGMIB-labeled non-targeting control VHH and (2) administration of the vehicle solution PBS.

Materials and Methods

19 CRL:Nu-FoxNlnu mice were inoculated in the right hind leg with 5×10⁶ HER2+ BT474/M1 tumor cells in 50/50 matrigel/cell culture medium. Tumors were grown until 50±30 mm³, as determined by caliper measurements. Next, animals were randomly divided into 3 treatment groups; Treatment group 1 (n=6): untagged monovalent [$^{131}$I] SGMIB-labeled anti-HER2 VHH 2Rs15d (250±50 μCi/treatment), treatment group 2 (n=6): untagged monovalent [$^{131}$I]SGMIB-labeled non-targeting control VHH (250±50 μCi/treatment), and treatment group 3 (n=7): vehicle solution. Animals were treated five times (once a week during five weeks). Tumor volume and animal weight was measured every week. Animals were euthanized when tumors reached 1 cm³ or when a weight reduction of >20% was observed. After 150 days. The results were combined in a survival curve, after which statistical analysis was performed (Log-rank (Mantel-Cox) test).

Results

Mice bearing small HER2+ BT474/M1 tumors (50±30 mm³) were intravenously injected with either untagged monovalent [$^{131}$I]SGMIB-labeled anti-HER2 VHH 2Rs15d, untagged monovalent [$^{131}$I]SGMIB-labeled non-targeting control VHH or the vehicle solution PBS. All animals of the PBS-treated (n=7) and all except for 1 animal in the group

TABLE 11

Biodistribution data for untagged monovalent [$^{131}$I]SGMIB-labeled anti-HER2 VHH 2Rs15d in female HER2+ tumor xenografted mice with and without competition of Trastuzumab, Pertuzumab, or a combination of both anti-HER2 mAbs. Values are expressed as % Injected Activity/gram tissue (% IA/g), except for thyroid, for which % IA is used. Values represent an average (n = 3) ± SD.

| Organ/tissue | 2Rs15d | | 2Rs15d + Trastuzumab | | 2Rs15d + Pertuzumab | | 2Rs15d + Trastuzumab and Pertuzumab | |
|---|---|---|---|---|---|---|---|---|
| Brain | 0.03 | 0.01 | 0.03 | 0.01 | 0.04 | 0.02 | 0.05 | 0.03 |
| Lungs | 0.94 | 0.33 | 0.59 | 0.22 | 0.75 | 0.21 | 0.97 | 0.46 |
| Heart | 0.34 | 0.03 | 0.35 | 0.04 | 0.39 | 0.03 | 0.47 | 0.06 |
| Liver | 1.58 | 0.26 | 1.82 | 0.78 | 0.95 | 0.49 | 1.38 | 0.29 |
| Kidney | 78.08 | 26.88 | 60.31 | 17.08 | 66.21 | 15.71 | 75.74 | 11.28 |
| Stomach | 0.54 | 0.15 | 0.58 | 0.19 | 0.51 | 0.19 | 0.87 | 0.28 |
| Pancreas | 0.13 | 0.03 | 0.14 | 0.01 | 0.21 | 0.14 | 0.18 | 0.01 |
| Spleen | 0.43 | 0.1 | 0.49 | 0.15 | 0.44 | 0.05 | 0.7 | 0.1 |
| Muscle | 0.53 | 0.16 | 0.87 | 0.7 | 0.34 | 0.06 | 0.87 | 0.53 |
| Bone | 0.95 | 0.19 | 0.78 | 0.06 | 1.14 | 0.46 | 1.1 | 0.1 |
| S. intestines | 0.27 | 0.1 | 0.25 | 0.06 | 0.24 | 0.08 | 0.45 | 0.1 |
| L. intestines | 0.32 | 0.14 | 0.16 | 0.03 | 0.25 | 0.12 | 0.41 | 0.09 |
| Lymphnodes | 0.56 | 0.12 | 0.46 | 0.08 | 0.55 | 0.13 | 0.91 | 0.21 |
| Blood | 0.77 | 0.11 | 0.57 | 0.06 | 0.66 | 0.14 | 0.82 | 0.09 |
| Uterus | 0.69 | 0.22 | 0.58 | 0.28 | 0.62 | 0.27 | 0.9 | 0.32 |
| Thyroid* | 0.01 | 0.002 | 0.002 | 0.001 | 0.002 | 0.001 | 0.002 | 0.001 |
| Tumor | 11.00 | 3.94 | 9.31 | 2.35 | 8.91 | 2.06 | 8.59 | 2.85 | treated with untagged monovalent [$^{131}$I]SGMIB-labeled non-targeting control VHH (n=6), were euthanized at day 150 due to the development of large tumors (>1 cm$^3$) (FIG. 20). No statistically significant difference was observed in event-free survival between both control groups.

In contrast, tumor growth was delayed significantly in the group treated with untagged monovalent [$^{131}$I]SGMIB-labeled anti-HER2 VHH 2Rs15d compared to the two control animal groups (FIG. 20). Moreover, up to day 150, half of the treated animal group showed complete absence of tumor burden. Overall, survival was significantly longer for the treated group compared to the control groups that received PBS (P<0.05) or untagged monovalent [$^{131}$I]SGMIB-labeled non-targeting control VHH (P<0.05), respectively. This finding is remarkably surprising as it is shown that a radiolabeled untagged, non-lifetime extended, monovalent VHH has a therapeutic effect, while it is commonly accepted that for a therapeutic effect, lifetime extension and multivalency are required.

Example 9

Dose-escalating toxicity curves are established in mice for 131I-SGMIB labeled 2Rs15d or other VHHs to assess the toxicity limited dose for these probes.

Biodistribution analyses of low doses of GMP grade 131I-SGMIB-2Rs15d are performed in human volunteer breast cancer patients to establish effective targeting of Her2-positive tumor lesions but low background signals in other body tissues, such as the kidneys.

Therapeutic efficacy of the administration of high doses of 131I-SGMIB-2Rs15d at a regimen of 7 weekly injections is evaluated in athymic nude mice bearing subcutaneous Her2+SKOV3 cells transfected with luciferase-encoding lentiviral particles, thereby measuring tumor growth retardation as compared to control group mice through caliper measurement and/or bioluminescence imaging.

---

The invention claimed is:

1. A method for the treatment of cancer, the method comprising:
   administering to a subject in need thereof an effective amount of a radiolabelled, untagged monovalent heavy chain variable domain derived from a heavy chain antibody ($V_{HH}$), or a functional fragment thereof, which specifically binds to HER2 that is present on a cancer cell or solid tumor, wherein the radiolabelled, untagged monovalent VHH comprises one of the CDR combinations selected from the group consisting of: a CDR1 region having SEQ ID NO:1, a CDR2 region having SEQ ID NO:2, and a CDR3 region having SEQ ID NO:3, and a CDR1 region having SEQ ID NO:4, a CDR2 region having SEQ ID NO:5, and a CDR3 region having SEQ ID NO:6.

2. The method of claim 1, wherein the radiolabelled, untagged monovalent $V_{HH}$ or functional fragment thereof is labeled with a halogen radio-isotope.

3. The method of claim 2, wherein the radiolabelled, untagged monovalent $V_{HH}$ or functional fragment thereof is labeled with 131-Iodine.

4. The method of claim 1, wherein the radiolabelled, untagged monovalent $V_{HH}$ or functional fragment thereof is labeled with 131-Iodine using N-succinimidyl-4-guanidinomethyl-3-[I-131]iodobenzbate ([I-131]SGMIB) or a suitable derivative or variant thereof.

5. The method of claim 1, wherein the radiolabelled, untagged monovalent $V_{HH}$ or functional fragment thereof is labeled with a radio-isotope chosen from the group consisting of α-emitting radioisotopes and β-emitting radioisotopes.

6. The method of claim 5, wherein the radiolabelled, untagged monovalent $V_{HH}$ or functional fragment thereof is labeled with a radio-isotope chosen from the group consisting of Actinium-225, Astatine-211, Bismuth-212, Bismuth-213, Caesium-137, Chromium-51, Cobalt-60, Dysprosium-165, Erbium-169, Fermium-255, Gold-198, Holium-166, Iodine-125, Iodine-131, Iridium-192, Iron-59, Lead-212, Lutetium-177, Molydenum-99, Palladium-103, Phosphorus-32, Potassium-42, Rhenium-186, Rhenium-188, Samarium-153, Technitium-99m, Radium-223, Ruthenium-106, Sodium-24, Strontium-89, Terbium-149, Thorium-227, Xenon-133, Ytterbium-169, Ytterbium-177 and Yttrium-90.

7. The method of claim 1, wherein the radiolabelled, untagged monovalent $V_{HH}$ or functional fragment thereof is administered to the subject in a calculated mean effective dose of between 0.002 and 0.1 mSv/MBq in said subject.

8. The method of claim 1, wherein the radiolabelled, untagged monovalent $V_{HH}$ or functional fragment thereof is administered to the subject at an administration interval of between once a day and once a month or between once a month and once a year.

9. The method of claim 1, wherein the radiolabelled, untagged monovalent $V_{HH}$, or functional fragment thereof, has at least 80% amino acid identity with at least one of the amino acid sequences of SEQ ID NOs:7 and 8.

10. The method of claim 9, wherein the radiolabelled, untagged monovalent $V_{HH}$, or functional fragment thereof, is identical with at least one of the amino acid sequences of SEQ ID NOs:7 and 8.

11. The method of claim 1, wherein the cancer is breast cancer.

12. The method of claim 1, wherein the method further comprises performing immunotherapy on the subject.

13. The method of claim 1, wherein the radiolabelled, monovalent $V_{HH}$ or functional fragment thereof is administered to the subject intravenously, intrathecally, or intraperitoneally.

14. The method of claim 1, wherein the radiolabelled, monovalent $V_{HH}$ or functional fragment thereof is non-lifetime extended.

15. The method of claim 1, wherein residual malignant cells are targeted in the subject.

16. The method of claim 15, wherein minimal residual disease is reduced or eliminated in the subject.

17. The method of claim 15, wherein the residual malignant cells are present in the patient after remission.

18. The method of claim 1, wherein the radiolabelled, untagged monovalent VHH comprises: a CDR1 region having SEQ ID NO:1, a CDR2 region having SEQ ID NO:2, and a CDR3 region having SEQ ID NO:3.

19. The method of claim 1, wherein the radiolabelled, untagged monovalent VHH comprises: a CDR1 region having SEQ ID NO:4, a CDR2 region having SEQ ID NO:5, and a CDR3 region having SEQ ID NO:6.

* * * * *

UNITED STATES PATENT AND TRADEMARK OFFICE
CERTIFICATE OF CORRECTION

PATENT NO. : 9,855,348 B2
APPLICATION NO. : 14/802077
DATED : January 2, 2018
INVENTOR(S) : Nick Devoogdt et al.

It is certified that error appears in the above-identified patent and that said Letters Patent is hereby corrected as shown below:

In the Specification

At Column 3, Lines 26-27, delete "N-succinimidyl-4-guanidinomethyl-3-[I-131 ]iodobenzbate" and insert -- N-succinimidyl-4-guanidinomethyl-3-[I-131]iodobenzoate --

At Column 3, Lines 61-62, delete "N-succinimidyl-4-guanidinomethyl-3-[I-131 ]iodobenzbate" and insert -- N-succinimidyl-4-guanidinomethyl-3-[I-131]iodobenzoate --

At Column 4, Lines 49-50, delete "N-succinimidyl-4-guanidinomethyl-3-[I-131 ]iodobenzbate" and insert -- N-succinimidyl-4-guanidinomethyl-3-[I-131]iodobenzoate --

At Column 4, Line 57, delete "N-succinimidyl-4-guanidinomethyl-3-[I-131 ]iodobenzbate" and insert -- N-succinimidyl-4-guanidinomethyl-3-[I-131]iodobenzoate --

At Column 4, Lines 63-64, delete "N-succinimidyl-4-guanidinomethyl-3-[I-131 ]iodobenzbate" and insert -- N-succinimidyl-4-guanidinomethyl-3-[I-131]iodobenzoate --

At Column 5, Lines 25-26, delete "N-succinimidyl-4-guanidinomethyl-3-[I-131 ]iodobenzbate" and insert -- N-succinimidyl-4-guanidinomethyl-3-[I-131]iodobenzoate --

At Column 5, Lines 29-30, delete "N-succinimidyl-4-guanidinomethyl-3-[I-131 ]iodobenzbate" and insert -- N-succinimidyl-4-guanidinomethyl-3-[I-131]iodobenzoate --

At Column 6, Lines 12-13, delete "N-succinimidyl-4-guanidinomethyl-3-[I-131 ]iodobenzbate" and insert -- N-succinimidyl-4-guanidinomethyl-3-[I-131]iodobenzoate --

At Column 6, Line 21, delete "N-succinimidyl-4-guanidinomethyl-3-[I-131 ]iodobenzbate" and insert -- N-succinimidyl-4-guanidinomethyl-3-[I-131]iodobenzoate --

Signed and Sealed this
Eighteenth Day of December, 2018

Andrei Iancu
*Director of the United States Patent and Trademark Office*

CERTIFICATE OF CORRECTION (continued)
U.S. Pat. No. 9,855,348 B2

At Column 6, Lines 28-29, delete "N-succinimidyl-4-guanidinomethyl-3-[I-131 ]iodobenzbate" and insert -- N-succinimidyl-4-guanidinomethyl-3-[I-131]iodobenzoate --

At Column 6, Lines 52-53, delete "N-succinimidyl-4-guanidinomethyl-3-[I-131 ]iodobenzbate" and insert -- N-succinimidyl-4-guanidinomethyl-3-[I-131]iodobenzoate --

At Column 6, Lines 58-59, delete "N-succinimidyl-4-guanidinomethyl-3-[I-131 ]iodobenzbate" and insert -- N-succinimidyl-4-guanidinomethyl-3-[I-131]iodobenzoate --

At Column 7, Lines 31-32, delete "N-succinimidyl-4-guanidinomethyl-3-[I-131 ]iodobenzbate" and insert -- N-succinimidyl-4-guanidinomethyl-3-[I-131]iodobenzoate --

At Column 7, Lines 38-39, delete "N-succinimidyl-4-guanidinomethyl-3-[I-131 ]iodobenzbate" and insert -- N-succinimidyl-4-guanidinomethyl-3-[I-131]iodobenzoate --

At Column 7, Lines 45-46, delete "N-succinimidyl-4-guanidinomethyl-3-[I-131 ]iodobenzbate" and insert -- N-succinimidyl-4-guanidinomethyl-3-[I-131]iodobenzoate --

At Column 9, Lines 2-3, delete "N-succinimidyl-4-guanidinomethyl-3-[I-131 ]iodobenzbate" and insert -- N-succinimidyl-4-guanidinomethyl-3-[I-131]iodobenzoate --

At Column 11, Lines 29-30, delete "N-succinimidyl-4-guanidinomethyl-3-[I-131 ]iodobenzbate" and insert -- N-succinimidyl-4-guanidinomethyl-3-[I-131]iodobenzoate --

At Column 49, Lines 2-3, delete "N-succinimidyl-4-guanidinomethyl-3-[I-131 ]iodobenzbate" and insert -- N-succinimidyl-4-guanidinomethyl-3-[I-131]iodobenzoate --

At Column 49, Lines 6-7, delete "N-succinimidyl-4-guanidinomethyl-3-[I-131 ]iodobenzbate" and insert -- N-succinimidyl-4-guanidinomethyl-3-[I-131]iodobenzoate --

In the Claims

At Column 79, Claim 4, Lines 65-66, delete "N-succinimidyl-4-guanidinomethyl-3-[I-131 ]iodobenzbate" and insert -- N-succinimidyl-4-guanidinomethyl-3-[I-131]iodobenzoate --

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: CDR1 sequence of VHH 2Rs15d

<400> SEQUENCE: 1

Gly Tyr Ile Phe Asn Ser Cys Gly
1               5

<210> SEQ ID NO 2
<211> LENGTH: 7
<212> TYPE: PRT
<213> ORGANISM: Artificial Sequence
<220> FEATURE:
<223> OTHER INFORMATION: CDR2 sequence of VHH 2Rs15d

<400> SEQUENCE: 2

Ile Ser Gly Asp Gly Asp Thr
1               5

<210> SEQ ID NO 3
<211> LENGTH: 9
<212> TYPE: PRT
<213> ORGANISM: Artificial Sequence
<220> FEATURE:
<223> OTHER INFORMATION: CDR3 sequence of VHH 2Rs15d

<400> SEQUENCE: 3

Ala Val Cys Tyr Asn Leu Glu Thr Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: CDR1 sequence of VHH 2Rb17c

<400> SEQUENCE: 4

Gly Phe Ile Phe Ser Asn Asp Ala
1               5
```

```
<210> SEQ ID NO 5
<211> LENGTH: 8
<212> TYPE: PRT
<213> ORGANISM: Artificial Sequence
<220> FEATURE:
<223> OTHER INFORMATION: CDR2 sequence of VHH 2Rb17c

<400> SEQUENCE: 5

Ile Asn Trp Ser Gly Thr His Thr
1               5

<210> SEQ ID NO 6
<211> LENGTH: 10
<212> TYPE: PRT
<213> ORGANISM: Artificial Sequence
<220> FEATURE:
<223> OTHER INFORMATION: CDR3 sequence of VHH 2Rb17c

<400> SEQUENCE: 6

Val Thr Gly Tyr Gly Val Thr Lys Thr Pro
1               5                   10

<210> SEQ ID NO 7
<211> LENGTH: 115
<212> TYPE: PRT
<213> ORGANISM: Artificial Sequence
<220> FEATURE:
<223> OTHER INFORMATION: VHH sequence 2Rs15d

<400> SEQUENCE: 7

Gln Val Gln Leu Gln Glu Ser Gly Gly Gly Ser Val Gln Ala Gly Gly
1               5                   10                  15

Ser Leu Lys Leu Thr Cys Ala Ala Ser Gly Tyr Ile Phe Asn Ser Cys
            20                  25                  30

Gly Met Gly Trp Tyr Arg Gln Ser Pro Gly Arg Glu Arg Glu Leu Val
        35                  40                  45

Ser Arg Ile Ser Gly Asp Gly Asp Thr Trp His Lys Glu Ser Val Lys
    50                  55                  60

Gly Arg Phe Thr Ile Ser Gln Asp Asn Val Lys Lys Thr Leu Tyr Leu
65                  70                  75                  80

Gln Met Asn Ser Leu Lys Pro Glu Asp Thr Ala Val Tyr Phe Cys Ala
                85                  90                  95

Val Cys Tyr Asn Leu Glu Thr Tyr Trp Gly Gln Gly Thr Gln Val Thr
            100                 105                 110

Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: VHH sequence 2Rb17c

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ile Phe Ser Asn Asp
            20                  25                  30

Ala Met Thr Trp Val Arg Gln Ala Pro Gly Lys Gly Leu Glu Trp Val
        35                  40                  45
```

```
Ser Ser Ile Asn Trp Ser Gly Thr His Thr Asn Tyr Ala Asp Ser Val
    50                  55                  60

Lys Gly Arg Phe Thr Ile Ser Arg Asp Asn Ala Lys Arg Thr Leu Tyr
65                  70                  75                  80

Leu Gln Met Asn Ser Leu Lys Asp Glu Asp Thr Ala Leu Tyr Tyr Cys
                85                  90                  95

Val Thr Gly Tyr Gly Val Thr Lys Thr Pro Thr Gly Gln Gly Thr Gln
                100                 105                 110

Val Thr Val Ser Ser
            115

<210> SEQ ID NO 9
<211> LENGTH: 6
<212> TYPE: PRT
<213> ORGANISM: Artificial Sequence
<220> FEATURE:
<223> OTHER INFORMATION: His-tag

<400> SEQUENCE: 9

His His His His His His
1               5

<210> SEQ ID NO 10
<211> LENGTH: 23
<212> TYPE: PRT
<213> ORGANISM: Artificial Sequence
<220> FEATURE:
<223> OTHER INFORMATION: Myc-His-tag

<400> SEQUENCE: 10

Ala Ala Ala Glu Gln Lys Leu Ile Ser Glu Glu Asp Leu Asn Gly Ala
1               5                   10                  15

Ala His His His His His His
            20
```